US012698344B2

(12) United States Patent
Benhar et al.

(10) Patent No.: US 12,698,344 B2
(45) Date of Patent: Aug. 4, 2026

(54) ANTI-IDE ANTIBODIES AND USES OF SAME

(71) Applicant: Ramot at Tel-Aviv University Ltd., Tel-Aviv (IL)

(72) Inventors: Itai Benhar, Tel Aviv (IL); Limor Nahary, Tel Aviv (IL); Dan Frenkel, Tel Aviv (IL); Ofir Fursht, Tel Aviv (IL); Yuval Nash, Tel Aviv (IL); Mirit Liran, Tel Aviv (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 985 days.

(21) Appl. No.: 17/793,943

(22) PCT Filed: Dec. 10, 2020

(86) PCT No.: PCT/IL2020/051279
§ 371 (c)(1),
(2) Date: Jul. 20, 2022

(87) PCT Pub. No.: WO2021/149040
PCT Pub. Date: Jul. 29, 2021

(65) Prior Publication Data
US 2023/0053258 A1　　Feb. 16, 2023

Related U.S. Application Data

(60) Provisional application No. 62/964,139, filed on Jan. 22, 2020.

(51) Int. Cl.
C07K 16/40　　(2006.01)
A61P 25/28　　(2006.01)
G01N 33/564　　(2006.01)
G01N 33/68　　(2006.01)

(52) U.S. Cl.
CPC .............. C07K 16/40 (2013.01); A61P 25/28 (2018.01); G01N 33/564 (2013.01); G01N 33/6893 (2013.01); *C07K 2317/24* (2013.01); *C07K 2317/565* (2013.01); *G01N 2800/042* (2013.01)

(58) Field of Classification Search
CPC ................ C07K 16/40; C07K 2317/24; C07K 2317/565; C07K 2317/64; C07K 2317/92; C07K 2317/94; C07K 2317/622; C07K 2317/76; A61P 25/28; A61P 3/10; G01N 33/564; G01N 33/6893; G01N 2800/042; G01N 2800/164; G01N 2800/28; G01N 2800/347; G01N 33/56994; G01N 2800/52; G01N 33/6896; A61K 2039/505
See application file for complete search history.

(56) References Cited

U.S. PATENT DOCUMENTS

| | | | |
|---|---|---|---|
| 8,632,989 | B1 | 1/2014 | Rodgers et al. |
| 2008/0274096 | A1 | 11/2008 | Andersson et al. |
| 2008/0317732 | A1 | 12/2008 | Hersh |
| 2016/0282364 | A1 | 9/2016 | Maianit et al. |

FOREIGN PATENT DOCUMENTS

| | | |
|---|---|---|
| JP | 2012-510277 | 5/2012 |
| RU | 2353389 | 4/2009 |
| WO | WO 02/093127 | 11/2002 |
| WO | WO 2006/128026 | 11/2006 |
| WO | WO 2010/063288 | 6/2010 |
| WO | WO 2010/086867 | 8/2010 |
| WO | WO 2012/017439 | 2/2012 |
| WO | WO 2021/149040 | 7/2021 |

OTHER PUBLICATIONS

Notice of Reasons for Rejection Dated Nov. 26, 2024 From the Japan Patent Office Re. Application No. 2022-544308 and Its Translation Into English. (8 Pages).
English Translation Dated Sep. 2, 2024 of Request for Examination and Search Report Dated Aug. 6, 2024 From the (Rospatent), The Federal Service for Intellectual Property, Patents and Trademarks of the Russian Federation Re. Application No. 2022122348 and Its Summary in English. (6 Pages).
Badri "Optimization of Radiation Dosing Schedules for Proneural Glioblastoma", Journal of Mathematical Biology, 72:1301-1336, Published Jun. 21, 2015.
Baylot et al. "TCTP Has a Crucial Role in the Different Stages of Prostate Cancer Malignant 4 Progression 5", Results and Problems in Cell Differentiation, TCTP/tpt1—Remodeling Signaling from Stem Cell to Disease, 255-261, Nov. 18, 2017.
Request for Examination and Search Report Dated Aug. 6, 2024 From the (Rospatent), The Federal Service for Intellectual Property, Patents and Trademarks of the Russian Federation Re. Application No. 2022122348 and Its Summary in English. (11 Pages.
Request for Examination and Search Report Dated Apr. 8, 2024 From the (Rospatent), Federal Government Institution of Industrial Property of the Federal Service of Intellectual Property, Patents and Trademark of the Russian Federation Re. Application No. 2022122348 and Its Summary in English. (7 Pages).
Translation Dated Apr. 27, 2024 of Request for Examination and Search Report Dated Apr. 8, 2024 From the (Rospatent), Federal Government Institution of Industrial Property of the Federal Service of Intellectual Property, Patents and Trademark of the Russian Federation Re. Application No. 2022122348. (4 pages).
International Search Report and the Written Opinion Dated Feb. 28, 2021 From the International Searching Authority Re. Application No. PCT/IL2020/051279. (22 Pages).

(Continued)

*Primary Examiner* — Olga N Chernyshev

(57) ABSTRACT

Isolated anti-IDE antibodies are provided. Each of the antibodies comprise an antigen recognition domain comprising the indicated CDR amino acid sequences. Methods of producing same, methods of using same, pharmaceutical compositions comprising same and articles of manufacture are also provided.

11 Claims, 14 Drawing Sheets

Specification includes a Sequence Listing.

(56) References Cited

OTHER PUBLICATIONS

Blomqvist et al. "Sequence Variants of IDE Are Associated With the Extent of Beta-Amyloid Deposition in the Alzheimer's Disease Brain", Neurobiology of Aging, 26(6): 795-802, Jun. 2005.

Delledonne et al. "Development of Monoclonal Antibodies and Quantitative ELISAs Targeting Insulin-Degrading Enzyme", Molecular Neurodegeneration, 4(1): 39-1-39-6, Oct. 16, 2009.

Duckworth et al. "Insulin-Degrading Activity in Wound Fluid", The Journal of Clinical Endocrinology & Metabolism, 89(2): 847-851, Feb. 2004.

Guan et al. "IGF-1 Derived Small Neuropeptides and Analogues: A Novel Strategy for the Development of Pharmaceuticals for Neurological Conditions", British Journal of Pharmacology, 157(6): 881-891, Published Online May 11, 2009.

Hoelscher et al. "New Roles for Insulin-Like Hormones in Neuronal Signalling and Protection: New Hopes for Novel Treatments of Alzheimer's Disease?", Neurobiology of Aging, 31(9): 1495-1502, Published Online Oct. 18, 2008.

Levy et al. "Characterization of Brain Lesions in A Mouse Model of Progressive Multiple Sclerosis", Experimental Neurology, 226(1): 148-158, Published Online Aug. 22, 2010.

Maher et al. "Interaction Between Interferon Gamma and Insulin-Like Growth Factor-1 in Hippocampus Impacts on the Ability of Rats to Sustain Long-Term Potentiation", Journal of Neurochemistry, 96(6): 1560-1571, Published Online Feb. 8, 2006.

Maianti et al. "Anti-Diabetic Activity of Insulin-Degrading Enzyme Inhibitors Mediated by Multiple Hormones", Nature, 511(7507): 94-98, Jul. 3, 2014.

Morelli et al. "Insulin-Degrading Enzyme in Brain Microvessels: Proteolysis of Amyloid Beta Vasculotropic Variants and Reduced Activity in Cerebral Amyloid Angiopathy", The Journal of Biological Chemistry, 279(53): 56004-56013, Published Online Oct. 15, 2004.

Shii et al. "Inhibition of Insulin Degradation by Hepatoma Cells After Microinjection of Monoclonal Antibodies to A Specific Cytosolic Protease", Proc. Natl. Acad. Sci. USA, 83(12): 4147-4151, Jun. 1986.

Sofer et al. "MON-LB031 Higher Insulin Degrading Enzyme Levels in Subjects With Metabolic Syndrome", Journal of the Endocrine Society, 3(Suppl. 1): # MON-LB031, Published Online Apr. 30, 2019.

Tang et al. "Targeting Insulin-Degrading Enzyme to Treat Type 2 Diabetes", Trends in Endocrinology and Metabolism, 27(1): 24-34, Published Online Dec. 2, 2015.

Winer et al. "Type I Diabetes and Multiple Sclerosis Patients Target Islet Plus Central Nervous System Autoantigens; Nonimmunized Nonobese Diabetic Mice Can Develop Autoimmune Encephalitis", The Journal of Immunology, 166(4): 2831-2841, Feb. 15, 2001.

Notification of Office Action and Search Report Dated Jan. 30, 2025 From the State Intellectual Property Office of the People's Republic of China Re. Application No. 202080098336.X and Its Summary and Machine Translation in English. (22 Pages).

NCBI "Low Quality Protein: Insulin-Degrading Enzyme [Pan paniscus]", NCBI Accession XP 008948937, Version XP 008948937. 1: 2P., May 1, 2018.

Xu et al. "Detection of TCF7L2 Binding to IDE Gene Promoters by Chromatin Immunoprecipitation", Life Science Research, 16(1): 54-58, Abstract. Feb. 2012.

Figure 1A
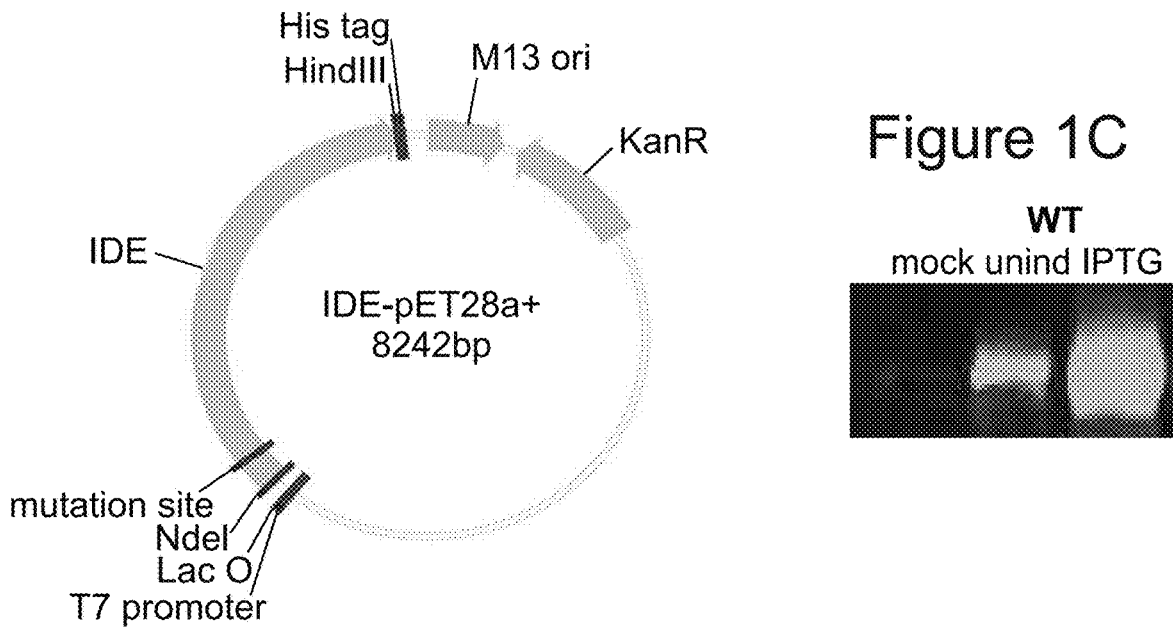
Figure 1C
WT
mock unind IPTG
Figure 1B
Figure 1D
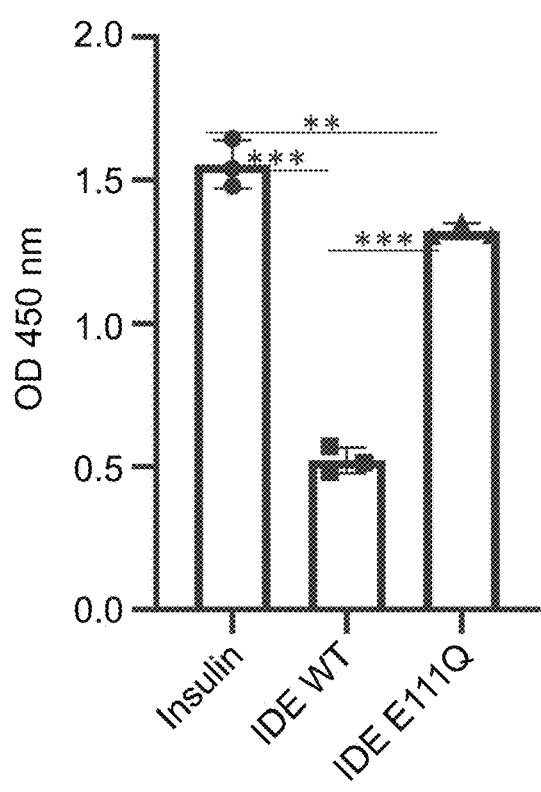

Figure 1E
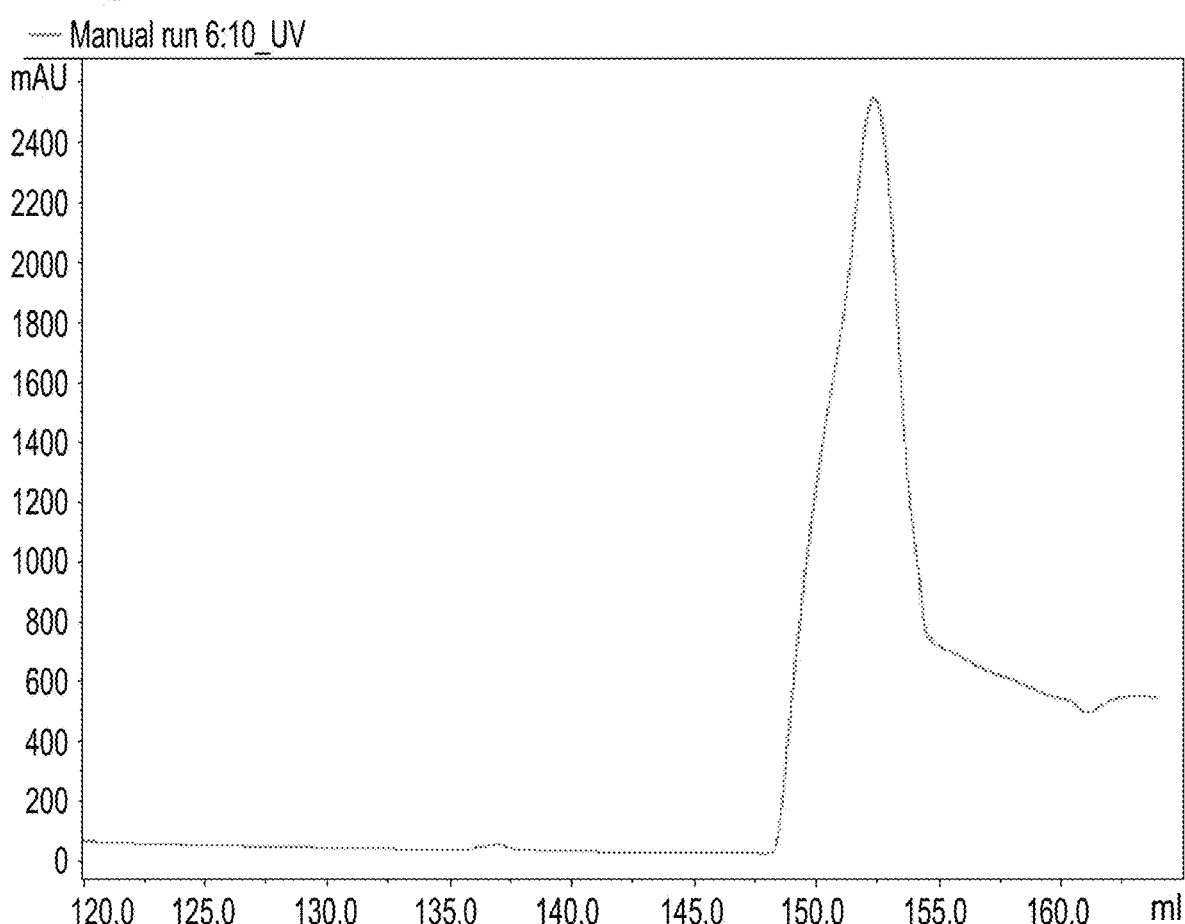
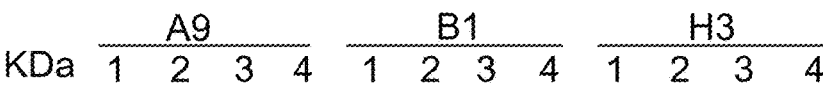
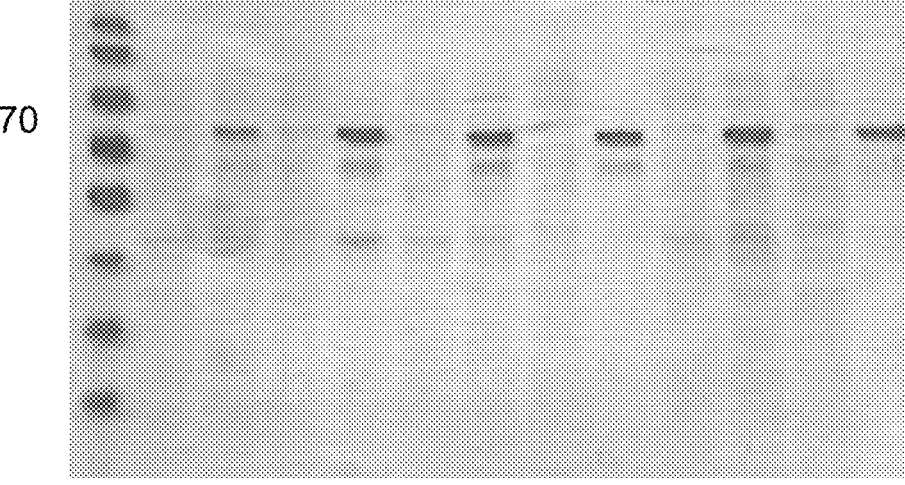

Figure 1F
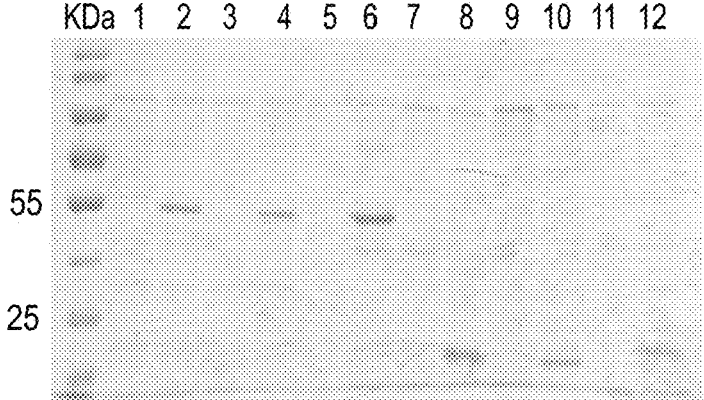
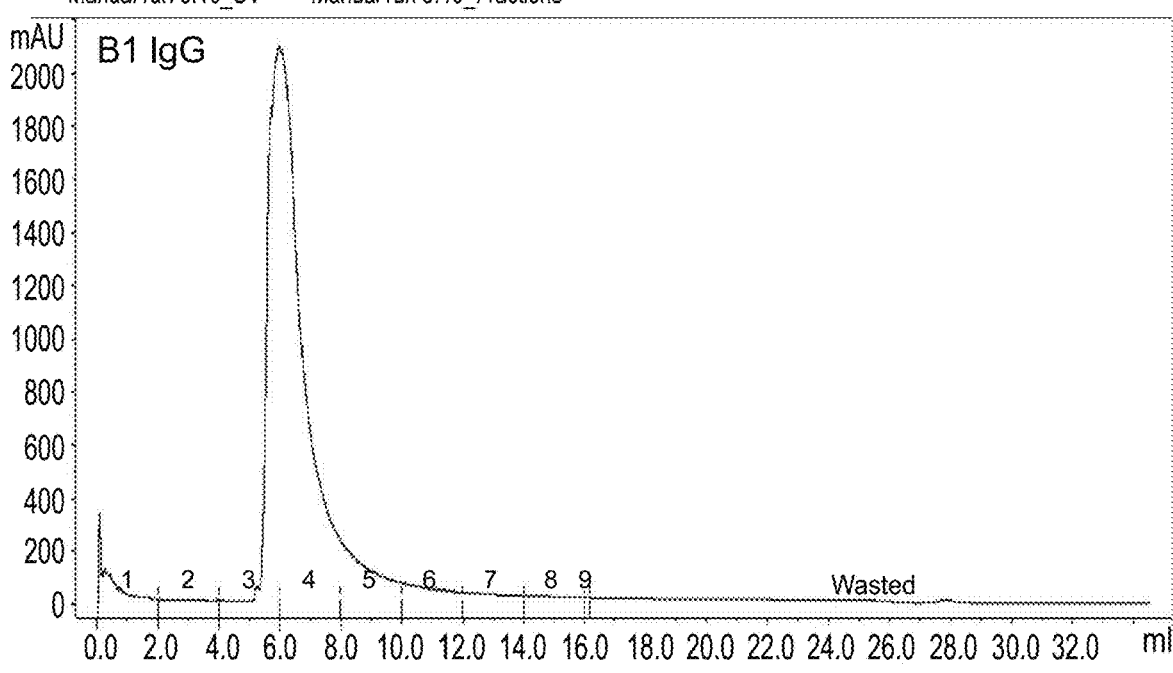
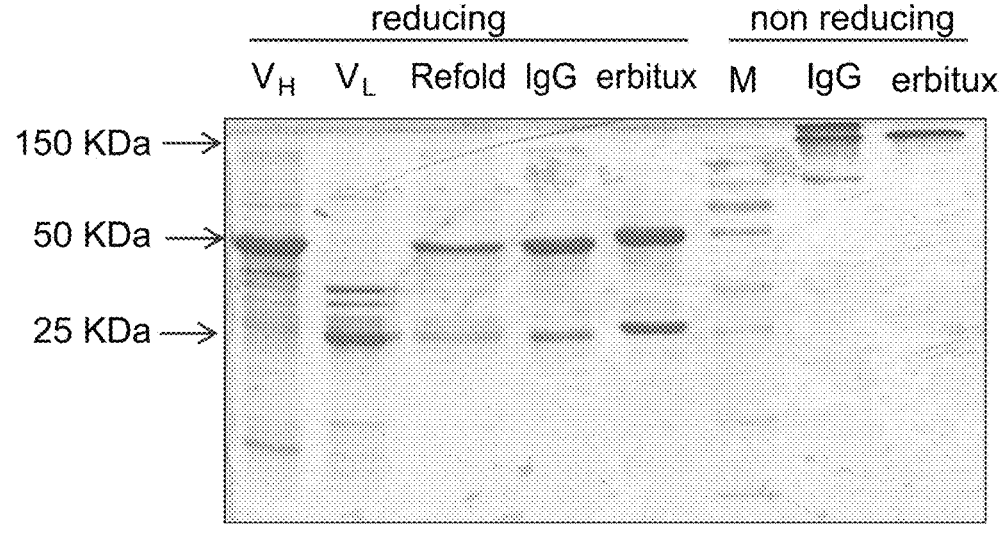

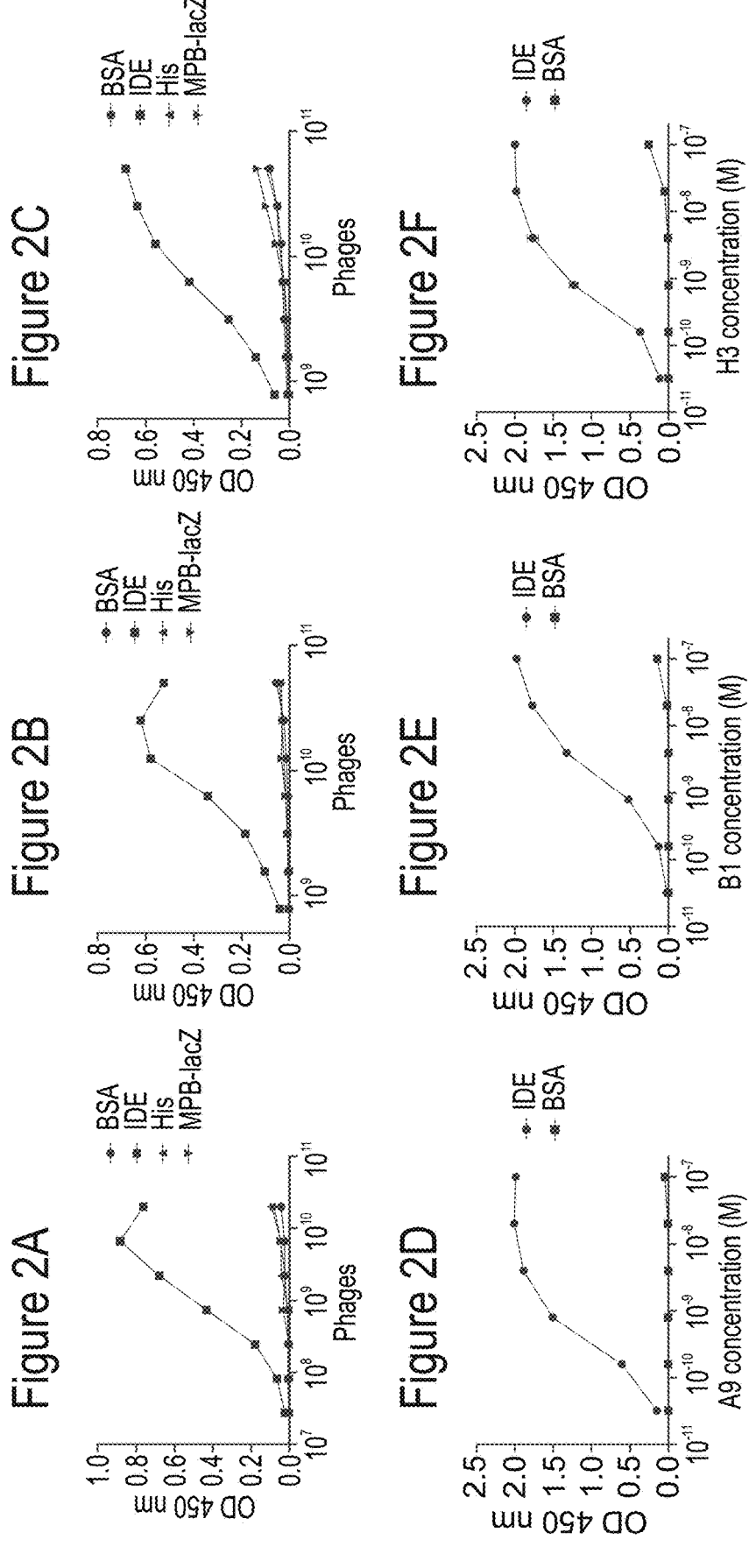

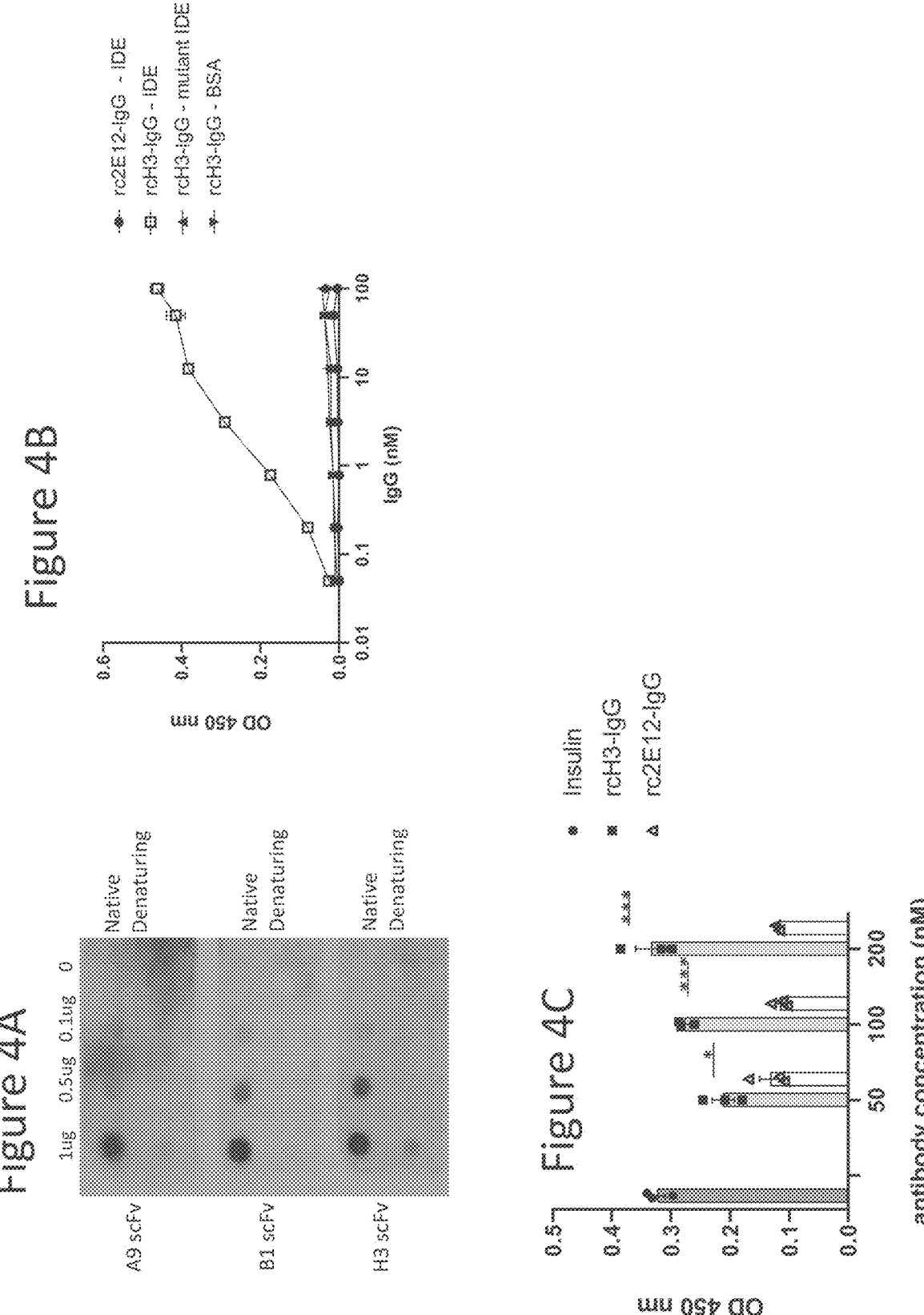

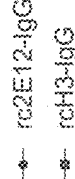
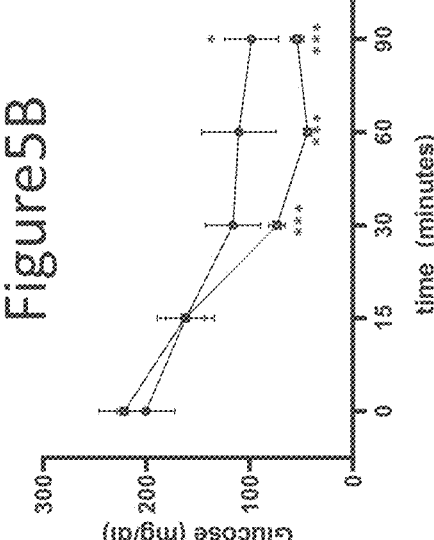
Figure5B
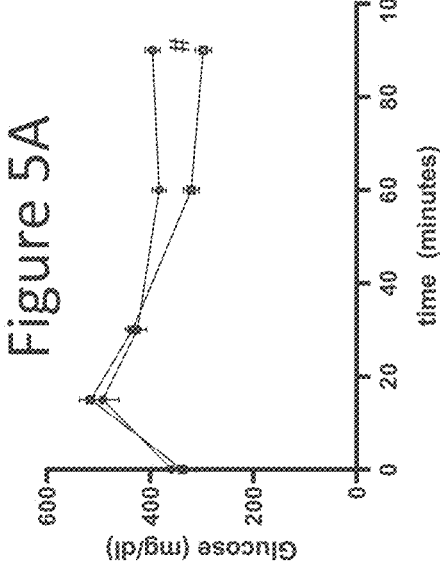
Figure 5A
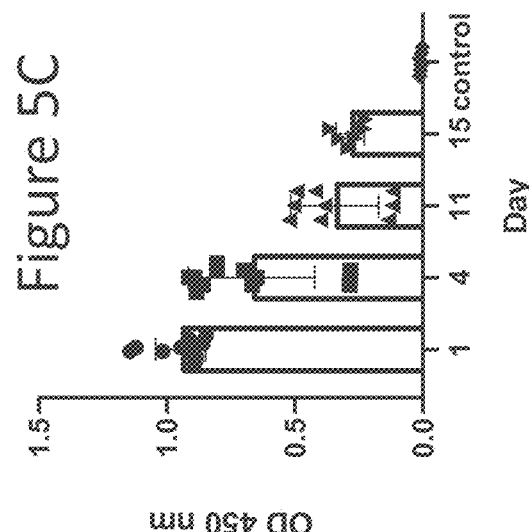
Figure 5C

ANTI-IDE ANTIBODIES AND USES OF SAME

REPLATED APPLICATIONS

This application is a National Phase of PCT Patent Application No. PCT/IL2020/051279 having International filing date of Dec. 10, 2020, which claims the benefit of priority under 35 USC § 119 (e) of U.S. Provisional Patent Application No. 62/964,139 filed on Jan. 22, 2020. The contents of the above applications are all incorporated by reference as if fully set forth herein in their entirety.

SEQUENCE LISTING STATEMENT

The ASCII file, entitled-85636 93028, created on Jul. 20, 2022, comprising 43,786 bytes, submitted concurrently with the filing of this application is incorporated herein by reference.

FIELD AND BACKGROUND OF THE INVENTION

The present invention, in some embodiments thereof, relates to anti-IDE antibodies and uses of same.

Insulin-degrading enzyme (IDE, insulin), is a large zinc-binding protease (approximately 110 kDa thiol zinc-metalloendopeptidase) located in cytosol, peroxisomes, endosomes, and on the cell surface. This enzyme cleaves small proteins of diverse sequences many of which share a propensity to form β-pleated sheet-rich amyloid fibrils, including amyloid β-protein (Aβ), insulin, glucagon, amylin, atrial natriuretic factor and calcitonin. Thus, IDE is known to cleave multiple short polypeptides and plays an important role in degrading different proteins, such as insulin and IGF-1, which were reported to modulate immune response activity.

Since its discovery, IDE inhibitors have been suggested for treatment of several diseases including e.g. diabetes, obesity, autoimmune diseases of the central nervous system, neurodegenerative diseases and varicella-zoster virus (VZV) infection (e.g. Maianti et al. (2014) Nature 511, 94-98; Tang, W.-J. (2016) Trends Endocrinol. etab. 27, 24-34; and International Patent Application Publication Nos. WO 2012/017439 and WO 2010/086867). For example, PCT Publication No. WO 2010/086867 by same Applicant discloses the use of an isolated peptide comprising an amino acid sequence being no more than 25 amino acids in length, the amino acid sequence comprising at least one aspartate or a homolog thereof, the peptide having an Insulin-Degrading Enzyme (IDE) inhibitory activity, for the manufacture of a medicament identified for treating a disease selected from the group consisting of diabetes, obesity, hyperglycemia, retinal damage, renal failure, nerve damage, microvascular damage and varicella-zoster virus (VZV) infection. PCT Publication No. WO 2012/017439 by same Applicant provides an insulin degrading enzyme (IDE) inhibitor (e.g. antibody) for use in the treatment of a disease selected from the group consisting of an autoimmune disease of the central nervous system and a neurodegenerative disease.

Several IDE monoclonal and polyclonal antibodies were described in the art for in-vitro detection of rodent and/or human IDE in various applications, including western blotting, immunoprecipitation, immunocytochemistry, immunohistochemistry and quantitative sandwich ELISAs [see for example Delledonne A. et al. Mol Neurodegener. (2009) 4:39].

SUMMARY OF THE INVENTION

According to an aspect of some embodiments of the present invention there is provided an isolated antibody comprising an antigen recognition region, which specifically binds IDE, wherein the antigen recognition domain comprises complementarity determining region (CDR) amino acid sequences as, set forth in:

(i) SEQ ID NOs: 4 (CDR1), 6 (CDR2) and 8 (CDR3), being sequentially arranged from N to C on a heavy chain of the antibody; and 12 (CDR1), 14 (CDR2) and 16 (CDR3), being sequentially arranged from N to C on a light chain of the antibody;

(ii) SEQ ID NOs: 20 (CDR1), 22 (CDR2) and 24 (CDR3), being sequentially arranged from N to C on a heavy chain of the antibody; and 28 (CDR1), 30 (CDR2) and 32 (CDR3), being sequentially arranged from N to C on a light chain of the antibody; or (iii) SEQ ID NOs: 36 (CDR1), 38 (CDR2) and 40 (CDR3), being sequentially arranged from N to C on a heavy chain of the antibody; and 44 (CDR1), 46 (CDR2) and 48 (CDR3), being sequentially arranged from N to C on a light chain of the antibody.

According to an aspect of some embodiments of the present invention there is provided a pharmaceutical composition comprising as an active ingredient the antibody (ii) or (iii) and a pharmaceutically acceptable carrier.

According to an aspect of some embodiments of the present invention there is provided a method for treating a disease associated with an IDE activity in a subject in need thereof, the method comprising administering to the subject a therapeutically effective amount of the antibody (ii) or (iii) or the pharmaceutical composition, thereby preventing or treating the disease associated with the IDE activity.

According to an aspect of some embodiments of the present invention there is provided the antibody (ii) or (iii) for use in treating a disease associated with an IDE activity in a subject in need thereof.

According to some embodiments of the invention, the method further comprising administering to the subject a therapeutic agent for treating the disease.

According to some embodiments of the invention, the antibody for use further comprising a therapeutic agent for the disease.

According to some embodiments of the invention, the subject has a level of IDE above a predetermined threshold in a biological sample as compared to a control biological sample.

According to some embodiments of the invention, the method comprising determining the level of IDE in the biological sample of the subject using the antibody prior to the administering.

According to an aspect of some embodiments of the present invention there is provided an article of manufacture identified for the treatment of a disease associated with an IDE activity comprising the antibody (ii) or (iii) and a therapeutic agent for treating the disease.

According to some embodiments of the invention, the antibody and the therapeutic agent are in separate containers.

According to some embodiments of the invention, the antibody and the therapeutic agent are in a co-formulation.

According to an aspect of some embodiments of the present invention there is provided a method of diagnosing a disease associated with an IDE activity in a subject, the method comprising determining a level of IDE in a biological sample of the subject using the antibody, wherein when the level of the IDE is above a predetermined threshold as compared to a control biological sample, the subject is diagnosed with the disease.

According to an aspect of some embodiments of the present invention there is provided a method of monitoring efficacy of a therapy for a disease associated with an IDE activity in a subject diagnosed with the disease, the method comprising determining a level of IDE in a biological sample of the subject undergoing or following the therapy using the antibody, wherein when the level of the IDE is decreased from a predetermined threshold following the therapy the therapy is efficacious.

According to an aspect of some embodiments of the present invention there is provided a method of treating a disease associated with an IDE activity in a subject in need thereof, the method comprising:

(a) diagnosing the subject according to the method; and wherein when the level of the IDE is above the predetermined threshold, (b) treating the subject with a therapy for the disease, thereby treating the disease in the subject.

According to an aspect of some embodiments of the present invention there is provided a method of treating a disease associated with an IDE activity in a subject in need thereof, the method comprising:

(a) diagnosing the subject according to the method; and wherein when the level of the IDE is above the predetermined threshold, (b) selecting a therapy based on the level of the IDE, thereby treating the disease in the subject.

According to some embodiments of the invention, the therapy comprises the antibody (ii) or (iii).

According to an aspect of some embodiments of the present invention there is provided a composition of matter comprising a biological sample of a subject diagnosed with a disease associated with an IDE activity, and the antibody.

According to some embodiments of the invention, the disease associated with the IDE activity is selected from the group consisting of an autoimmune disease of the central nervous system, a neurodegenerative disease, a metabolic syndrome, a diabetes, an obesity, a hyperglycemia, a retinal damage, a renal failure, a nerve damage, a microvascular damage, a varicella-zoster virus (VZV) infection and a wound.

According to some embodiments of the invention, the disease associated with the IDE activity is selected from the group consisting of an autoimmune disease of the central nervous system, a neurodegenerative disease, a diabetes, an obesity, a hyperglycemia, a retinal damage, a renal failure, a nerve damage, a microvascular damage, a varicella-zoster virus (VZV) infection and a wound.

According to some embodiments of the invention, the disease associated with the IDE activity is selected from the group consisting of a metabolic syndrome, a diabetes and an obesity.

According to some embodiments of the invention, the disease is diabetes.

According to some embodiments of the invention, the diabetes is type 1 diabetes.

According to some embodiments of the invention, the diabetes is type 2 diabetes.

According to some embodiments of the invention, the disease is metabolic syndrome.

According to some embodiments of the invention, the neurodegenerative disease is Parkinson's disease.

According to some embodiments of the invention, the neurodegenerative disease is Alzheimer's disease.

According to some embodiments of the invention, the autoimmune disease of the central nervous system is selected from the group consisting of multiple sclerosis, Guillain-Barre syndrome, Lambert-Eaton myasthenic syndrome, Myasthenia gravis, transverse myelitis, progressive multifocal leukoencephalopathy, chronic headache and cerebral palsy.

According to some embodiments of the invention, the autoimmune disease of the central nervous system is multiple sclerosis.

According to some embodiments of the invention, the wound is selected from the group consisting of a chronic wound, an acute wound, a diabetic wound, an ischemic wound, an ulcer, a burn and a surgical wound.

According to an aspect of some embodiments of the present invention there is provided an isolated polynucleotide encoding the antibody.

According to some embodiments of the invention, the nucleic acid sequences encoding the CDR amino acid sequences are as set forth in:

(i) SEQ ID NOs: 3, 5, 7, 11, 13 and 15;
(ii) SEQ ID NOs: 19, 21, 23, 27, 29 and 31; or
(iii) SEQ ID NOs: 35, 37, 39, 43, 45 and 47.

According to an aspect of some embodiments of the present invention there is provided a nucleic acid construct comprising the polynucleotide and a cis-acting regulatory element for directing expression of the polynucleotide.

According to an aspect of some embodiments of the present invention there is provided a host cell expressing the antibody, the polynucleotide or the nucleic acid construct.

According to an aspect of some embodiments of the present invention there is provided a method of producing an anti-IDE antibody, the method comprising expressing in a host cell the polynucleotide or the nucleic acid construct.

According to some embodiments of the invention, the method comprising isolating the antibody.

According to an aspect of some embodiments of the present invention there is provided a method of producing an anti-IDE antibody, the method comprising:

(a) providing a plurality of antibodies;
(b) screening the antibodies to select antibodies, which bind wild type IDE and not mutated IDE having a reduced catalytic activity compared to the wild type IDE.

According to some embodiments of the invention, the wild type IDE is as set forth in SEQ ID NO: 50.

According to some embodiments of the invention, the mutated IDE comprises an E111Q conversion corresponding to SEQ ID NO: 50.

According to some embodiments of the invention, the method further comprising screening the antibodies to select antibodies, which inhibit an insulin degrading activity of the IDE.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-G demonstrate generation of anti-IDE antibodies. FIGS. 1A-D demonstrate expression and purification of recombinant human wild type (WT) IDE and inactive IDE mutant (E111Q). FIG. 1A is a graphic map of a pET28a+ plasmid containing the recombinant IDE: The recombinant construct was ordered from Genewiz Company and inserted to the vector between NdeI and HindIII. His tag and Single nucleotide mutation site for catalytic inactive IDE (E111Q) are also marked. FIG. 1B illustrated SDS-PAGE of total cell extract (15 µg) from Rosetta BL21 E. coli cells carrying pET28a-IDE vector prior to and following induction with 0.5 mM IPTG (depicted as "unind" and "IPTG", respectively); purified protein (3 µg) eluted from GE HisTrap columns using imidazole (depicted as "pure"); protein (15 µg) washed away from GE His trap columns (depicted as "FT"). FIG. 1C illustrates western blot analysis of total cell extract (15 µg) from Rosetta BL21 E. coli cells carrying pET28a+ vector: empty vector (depicted as "mock"); Vector with rhIDE wildtype (WT) prior to and following induction (depicted as "unind" and "IPTG", respectively). IDE was detected using an anti-IDE polyclonal antibody followed by (IR)-dye secondary antibody. Fluorescent signal was detected by scanning the membrane in Oddisey scanner (Licor, pixel size 21 µm, 0.5 mm offset, intensity—6 and average quality). FIG. 1D is a bar graph demonstrating IDE activity assay. 1.5 µg/L human insulin was incubated with PBS, 12 µg/ml rhIDE WT or E111Q for 2 hours at 37° C. Residual insulin was later analyzed using Mercodia ultrasensitive mouse insulin ELISA. Detection was effected by an ELISA plate reader at 450 nm. The results are presented as mean±SEM (n=3).  p<0.01; * p<0.001, One way ANOVA with Bonferroni correction. FIG. 1E demonstrate expression and purification of anti-IDE MBP-scFv. A representative FPLC evaluation of A9 MBP-scFv is shown in the left image. Soluble fraction of bacterial lysate was applied to a GE HisTrap column. Elution was performed with 0.5 M imidazole at a flow rate of 2 ml/min (peak). A SDS-PAGE analysis of the three selected clones of MBP-scFv (A9, B1 and H3) is shown in the right image. Lanes 1 and 2: 15 µg of total cell extract from Rosetta BL21 E. coli cells carrying pMALc-NHNN-scFv vector prior to and following induction with 0.5 mM IPTG, respectively; Lane 4: 3 µg of purified protein eluted from GE HisTrap columns using imidazole; Lane 3: 15 µg of protein washed away from GE His trap columns. FIG. 1F demonstrates expression and purification of anti-IDE Inclonal IgGs. A SDS-PAGE analysis of light and heavy chains from the insoluble fraction of cell lysates of Rosetta pUBS500 E. coli cells carrying anti-IDE antibody chains in pHAK vectors is shown in the upper image. 10 µg of cell lysate prior to and following induction with IPTG (uneven and even number lanes, respectively) were loaded in each lane. Lanes 1-2: A9 $V_H$; Lanes 3-4: B1 $V_H$; Lanes 5-6: H3 $V_H$; Lanes 7-8: A9 $V_L$; Lanes 9-10: B1 $V_L$; Lanes 11-12 H3 $V_L$. A representative FPLC evaluation of B1 Inclonal IgG is shown in the middle image. Refolding solution of B1 light and heavy chains was applied to a GE MabSelect column. Elution was performed with citrate buffer pH=3.0 at a flow rate of 2 ml/min (peak). The lower image is a representative SDS-PAGE analysis of inclusion bodies of light and heavy chains purified from Rosetta pUBS500 E. coli cells carrying anti-IDE light and heavy chains in pHAK vector after induction with IPTG (depicted as "VL" and "VH", respectively); $V_L$ and $V_H$ following incubation in refolding solution (depicted as "refold"); Inclonal IgG following purification using Mab-Select columns (depicted as "IgG"); commercial IgG as positive control (erbitux), in reducing and non-reducing states. FIG. 1G demonstrates purification of reverse chimeric H3 antibody (rcH3-IgG). Shown is a SDS-PAGE (12% gel) analysis of the production and purification of rcH3-IgG as a mouse IgG1. Lane 1: conditioned medium 7 days post transfection (10 µg loaded); Lane M: molecular weight marker; Lane 2: protein-G purified rcH3-IgG (5 µg loaded).

FIGS. 2A-F demonstrate binding of anti-IDE phage displayed antibodies and corresponding "Inclonal" IgGs. FIGS. 2A-C are graphs demonstrating IDE binding by scFv displaying phages, clones A9 (FIG. 2A), B1 (FIG. 2B) and H3 (FIG. 2C), as determined by phage-ELISA. The analyzed scFv displaying phages were added in serial dilutions to ELISA plate wells coated with 2.5 µg/ml WT rhIDE IDE (depicted as "IDE") or non-relevant proteins: BSA, a His-Trap-purified recombinant protein (depicted as "His") and MBP-LacZ. Bound phages were detected with a mouse anti-M13 antibody followed by a HRP-conjugated goat anti-mouse secondary antibody. The results are presented as mean±SEM (n=3). FIGS. 2D-F are graphs demonstrating IDE binding by purified Inclonal IgGs, clones A9 (FIG. 2D), B1 (FIG. 2E) and H3 (FIG. 2F), as determined by ELISA. The analyzed antibodies were added in serial dilutions to ELISA plate wells coated with 2 µg/ml WT rhIDE IDE (depicted as "IDE") or BSA. Bound antibodies were detected with a HRP-conjugated goat anti-human secondary antibody. The results are presented as mean±SEM (n=4).

FIGS. 4A-C demonstrate characterization of conformational specificity of the generated anti-IDE antibodies. FIG. 4A is a representative dot blot image demonstrating binding of the generated MBP-scFv to native IDE. WT rhIDE in serial dilutions (0.1-1 µg) and 20 µg of mouse splenocytes cell lysate were spotted into the membrane in native or denatured state (following 5 minutes boiling at 95° C.). Next, anti-IDE MBP-scFvs (clone A9, B1 or H3) were added, followed by a mouse anti-MBP antibody and later HRP-conjugated goat anti-mouse secondary antibody. Detection was effected by an ECL reaction. FIG. 4B is a graph demonstrating binding of reverse-chimeric rcH3-IgG to WT or to mutated rhIDE, as determined by ELISA. 5 µg/ml of WT rhIDE, inactive IDE mutant (E111Q, depicted as "mutant IDE") or BSA were incubated with serial dilutions of rcH3-IgG or with the negative control antibody rc2E12-IgG (starting from 100 nM). Antibodies were detected using an HRP-conjugated goat anti-mouse secondary antibody. The results are presented as mean±SEM (n=3). FIG. 4C is a bar graph demonstrating inhibition of IDE activity as determined by residual insulin levels following incubation with rcH3-IgG or a negative control rc2E12-IgG. 0.1 µg/ml IDE was incubated with rcH3-IgG or rc2E12-IgG for 1 hour at room temperature, followed by incubation of 1.5 µg/L human insulin for 1 hour at 37° C. Residual insulin was later analyzed using Mercodia ultrasensitive mouse insulin ELISA. Detection was effected by an ELISA plate reader at 450 nm. The results are presented as mean±SEM (n=3).

FIGS. 5A-C demonstrate the therapeutic effect of the reverse-chimeric anti-IDE H3 antibody in a STZ-induced diabetes mouse model. FIGS. 5A-B show graphs demonstrating insulin levels following intraperitoneal administration of rcH3-IgG or a negative control rc2E12-IgG 2 days following STZ injection, as determined by an oGTT assay (n=5 mice in each group; # p<0.01 between groups; FIG. 5A) or an ITT assay (n=5 mice in each group; * p<0.05, * p<0.001 within group, FIG. 5B). FIG. 5**C is a graph demonstrating levels of rcH3-IgG at different days following intraperitoneal administration to STZ treated mice (n=2-4 mice in each group). The results are presented as mean±SEM.

FIG. 7A is a schematic presentation of the ELISA procedure: (I) well ELISA plates were coated overnight with recombinant A9 IgG that serves as the capture antibody; (II) wells were washed once with PBS and blocked with 3% skim milk; III) Serum was added to plate and known concentrations of recombinant human IDE used as control; (IV) wells were incubated with polyclonal rabbit anti IDE antibody that serves as the detection antibody; (V) wells were washed and incubated with HRP-conjugated goat anti-rabbit antibody and then developed as described in the methods. FIG. 7B shows sensitivity curve of the ELISA assay. FIG. 7C demonstrates that IgG A9 recognizes a conformational epitope on rhIDE. A solution of 5 µg/ml rhIDE in PBS was prepared and either used directly to coat half of an ELISA plate or denatured by heating at 80° C. for 20 minutes followed by chilling on ice before using it to coat the other half of the ELISA plate. Following coating, blocking and washing steps, IgG A9 at a concentrations of 100, 33.3, 11.1, or 3.7 nM was applied in triplicates to wells coated with native or with heat-denatured rhIDE. The results are presented as mean±SEM (n=3).

(FIG. 8B) To quantify total rhIDE coated onto the wells, the other half of the plate was incubated with HRP-conjugated goat anti His-tag antibody, diluted ×2000, ×4000, ×8000, ×16000 in PBST. The plate was left for 1 h at room temperature, and then washed three times with 300 µl/well of PBST. Finally, 50 µl/well of the HRP substrate TMB were added until color appeared. The reaction was stopped after 2 min by adding 50 µl/well 1 M H$_2$SO$_4$, and analyzed using a BioTek Epoch microplate reader. The optical density was measured at 450 and 620 nanometer wavelengths. The results are presented as mean±SEM (n=3).

DESCRIPTION OF SPECIFIC EMBODIMENTS OF THE INVENTION

Figure 1G:
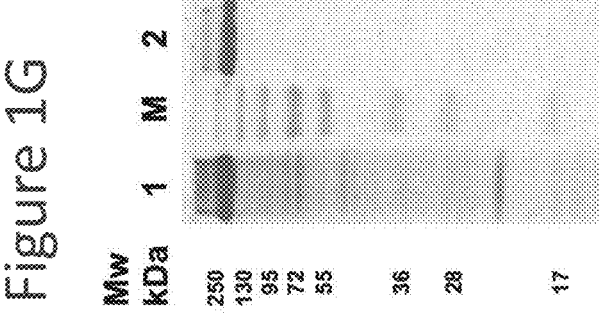

The present invention, in some embodiments thereof, relates to anti-IDE antibodies and uses of same.

The principles and operation of the present invention may be better understood with reference to the drawings and accompanying descriptions.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Insulin-degrading enzyme (IDE) is a large zinc-binding protease known to cleave multiple short polypeptides and plays an important role in degrading insulin. Several IDE monoclonal and polyclonal antibodies were described in the art for in-vitro [see for example Delledonne A. et al. Mol Neurodegener. (2009) 4:39] and in-vivo (see PCT Publication No. WO 2012/017439) applications. Furthermore, IDE inhibitors, including peptide inhibitors, have been previously described (see PCT Publication No. WO 2010/086867) for various therapeutic applications.

While reducing specific embodiments of the present invention to practice, the present inventors have generated novel monoclonal anti-IDE antibodies, which specifically target and inhibit insulin-degrading activity of the IDE. Consequently, specific embodiments of the present invention suggest using these anti-IDE antibodies as diagnostics and therapeutics of IDE related diseases and conditions.

As is shown in the Examples section which follows, the present inventors produced plasmids for expression of human insulin degrading enzyme (IDE) and mutated IDE (E111Q) in *E. coli* bacteria (Example 1, FIG. 1A). The mutated IDE (E111Q) comprises a site-specific mutation, which impairs catalytic activity due to inability to perform nucleophilic attack on the substrate. Thus, both peptides were used in order to isolate specific antibody clones, which bind with high affinity to the catalytic active IDE (i.e. wild type IDE). Thus, IDE proteins were expressed and purified from *E. coli* and protein purification and identity were verified (see FIGS. 1B-D). Using the phage display technique, the purified IDE was used as bait to isolate specific single-chain variable fragment (scFv) clones, which recognize and bind with high affinity epitopes of the recombinant human wild type IDE. Three clones of phages were selected, namely, A9, H3 and B1 (Example 1, FIGS. 2-C). Following, the scFvs were reformatted for production as soluble antibodies and tested in three formats: MBP-scFv, Human IgG1 produced as "Inclonals" and reverse-chimeric IgGs produced in mammalian cells culture. The specificity and IDE inhibitory properties of these antibodies were further verified in-vitro (Examples 1-2, FIGS. 1E-4C). In addition, a reverse-chimeric H3 IgG antibody improved glucose levels and insulin activity in a STZ-induced mouse diabetic model (Example 2, FIGS. 5A-C). Furthermore, Fab$_2$ fragments of the reverse-chimeric H3 IgG antibody reduced in-vitro production of reactive oxygen species in microglial cells having a phenotype of Parkinson's disease (Example 3, FIGS. 6A-B). Following, the present inventors have developed a highly sensitive ELISA using the generated antibodies (Example 4, FIGS. 7A-C). Using this ELISA the inventors were able to demonstrate a strong correlation between human serum IDE levels and presence and/or severity of metabolic syndrome (Example 4, FIGS. 9-10C).

Hence, according to an aspect of the present invention there is provided an isolated antibody comprising an antigen recognition region, which specifically binds IDE, wherein said antigen recognition domain comprises complementarity determining region (CDR) amino acid sequences as set forth in:

(i) SEQ ID NOs: 4 (CDR1), 6 (CDR2) and 8 (CDR3), being sequentially arranged from N to C on a heavy chain of said antibody; and 12 (CDR1), 14 (CDR2) and 16 (CDR3), being sequentially arranged from N to C on a light chain of said antibody;

(ii) SEQ ID NOs: 20 (CDR1), 22 (CDR2) and 24 (CDR3), being sequentially arranged from N to C on a heavy chain of said antibody; and 28 (CDR1), 30 (CDR2) and 32 (CDR3), being sequentially arranged from N to C on a light chain of said antibody; or (iii) SEQ ID NOs: 36 (CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody.

As used herein, the term "Insulin-Degrading Enzyme (IDE)" refers to the insulysin or insulin protease, a large zinc-binding protease of the M16A metalloprotease subfamily which is involved in the cellular processing of multiple short polypeptides including amyloid β-protein (Aβ), insulin, glucagon, amylin, atrial natriuretic factor and calcitonin (e.g., as set forth in GenBank Accession Nos. NM_004969 and NP_004960). According to specific embodiments, IDE is human IDE. An exemplary IDE of the present invention is set forth in EC 3.4.24.56.

As used herein, the term "wild type human insulin degrading enzyme", also referred to as WT IDE, refers to the expression product of the IDE gene of functional human IDE which has an affinity to insulin of 100 nM and degrades insulin at a rate of 36.6 μmole of human recombinant IDE degrades 1 μmole human Insulin/min. An exemplary WT IDE is set forth in SEQ ID NO: 50.

As used herein, the term "mutated IDE type E111Q" refers to the altered form with reduced catalytic activity of human IDE in which at least one catalytic site mutation (glutamic acid 111 to glutamine corresponding to SEQ ID NO: 50) occurs. An exemplary mutated IDE type E111Q is set forth in SEQ ID NO: 52.

The term "isolated" refers to at least partially separated from the natural environment e.g., from serum or being a predominant form of an antibody in a sample which comprises a plurality of antibodies or being the only antibody in a biological sample.

The term "antibody" as used in this invention includes intact molecules as well as functional fragments thereof (that are capable of binding to an epitope of an antigen).

As used herein, the term "epitope" refers to any antigenic determinant on an antigen to which the paratope of an antibody binds. Epitopic determinants usually consist of chemically active surface groupings of molecules such as amino acids or carbohydrate side chains and usually have specific three-dimensional structural characteristics, as well as specific charge characteristics.

According to a specific embodiment, the antibody fragments include, but are not limited to, single chain, Fab, Fab' and F(ab')$_2$ fragments, Fd, Fcab, Fv, dsFv, scFvs, MBP-scFvs, diabodies, minibodies, nanobodies, Fab expression library or single domain molecules such as VH and VL that are capable of binding to an epitope of the antigen in an HLA restricted manner.

According to specific embodiments, the antibody is a whole or intact antibody.

According to specific embodiments, the antibody is an antibody fragment.

Suitable antibody fragments for practicing some embodiments of the invention include a complementarity-determining region (CDR) of an immunoglobulin light chain (referred to herein as "light chain"), a complementarity-determining region of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single chain Fv (scFv), a disulfide-stabilized Fv (dsFv), an Fab, an Fab', and an F(ab')2, or antibody fragments comprising the Fc region of an antibody.

As used herein, the terms "complementarity-determining region" or "CDR" are used interchangeably to refer to the antigen binding regions found within the variable region of the heavy and light chain polypeptides. Generally, antibodies comprise three CDRs in each of the VH (CDR HI or HI; CDR H2 or H2; and CDR H3 or H3) and three in each of the VL (CDR LI or LI; CDR L2 or L2; and CDR L3 or L3).

The identity of the amino acid residues in a particular antibody that make up a variable region or a CDR can be determined using methods well known in the art and include methods such as sequence variability as defined by Kabat et al. (See, e.g., Kabat et al., 1992, Sequences of Proteins of Immunological Interest, 5th ed., Public Health Service, NIH, Washington D.C.), location of the structural loop regions as defined by Chothia et al. (see, e.g., Chothia et al., Nature 342:877-883, 1989.), a compromise between Kabat and Chothia using Oxford Molecular's AbM antibody modeling software (now Accelrys®, see, Martin et al., 1989, Proc. Natl Acad Sci USA. 86:9268; and world wide web site www(dot)bioinf-org(dot)uk/abs), available complex crystal structures as defined by the contact definition (see MacCallum et al., J. Mol. Biol. 262:732-745, 1996) and the "conformational definition" (see, e.g., Makabe et al., Journal of Biological Chemistry, 283:1156-1166, 2008).

As used herein, the "variable regions" and "CDRs" may refer to variable regions and CDRs defined by any approach known in the art, including combinations of approaches.

According to specific embodiments, the identity of the amino acid residues in the antibody that make up the variable region and/or the CDRs is determined by the deduced amino acid sequence of the translated coding gene.

Functional antibody fragments comprising whole or essentially whole variable regions of both light and heavy chains are defined as follows:

(i) Fv, defined as a genetically engineered fragment consisting of the variable region of the light chain (VL) and the variable region of the heavy chain (VH) expressed as two chains;

(ii) single chain Fv ("scFv"), a genetically engineered single chain molecule including the variable region of the light chain and the variable region of the heavy chain, linked by a suitable polypeptide linker as a genetically fused single chain molecule.

(iii) disulfide-stabilized Fv ("dsFv"), a genetically engineered antibody including the variable region of the light chain and the variable region of the heavy chain, linked by a genetically engineered disulfide bond.

(iv) Fab, a fragment of an antibody molecule containing a monovalent antigen-binding portion of an antibody molecule which can be obtained by treating whole antibody with the enzyme papain to yield the intact light chain and the Fd fragment of the heavy chain which consists of the variable and CH1 domains thereof;

(v) Fab', a fragment of an antibody molecule containing a monovalent antigen-binding portion of an antibody molecule which can be obtained by treating whole antibody with the enzyme pepsin, followed by reduction (two Fab' fragments are obtained per antibody molecule);

(vi) F(ab')2, a fragment of an antibody molecule containing a monovalent antigen-binding portion of an antibody molecule which can be obtained by treating whole antibody with the enzyme pepsin (i.e., a dimer of Fab' fragments held together by two disulfide bonds);

(vii) Single domain antibodies or nanobodies are composed of a single VH or VL domains which exhibit sufficient affinity to the antigen; and (viii) Fcab, a fragment of an antibody molecule containing the Fc portion of an antibody developed as an antigen-binding domain by introducing antigen-binding ability into the Fc region of the antibody.

According to specific embodiment, the antibody is a scFv.

According to specific embodiments, the antibody is a scFv stabilized by fusion to the E. coli maltose-binding protein, also known as MBP-scFv, as described for example by Bach H1, et al. J Mol Biol. (2001) Sep. 7; 312(1):79-93 and also in the Examples section which follows.

According to specific embodiments, the antibody is an IgG1, IgG2, IgG3, IgG4, IgM, IgA1, IgA2, IgD or IgE antibody.

According to specific embodiments, the antibody is an IgG antibody.

According to a specific embodiment, the antibody isotype is IgG1 or IgG4.

The antibody may be mono-specific (capable of recognizing one epitope or protein), bi-specific (capable of binding two epitopes or proteins) or multi-specific (capable of recognizing multiple epitopes or proteins).

According to specific embodiments, the antibody is a mono-specific antibody.

According to specific embodiments, the antibody is a multi-specific e.g. bi-specific, tri-specific, tetra-specific.

According to specific embodiments, the antibody is bi-specific antibody.

Bispecific antibodies, also known as bifunctional antibodies, have at least one antigen recognition site for a first antigen and at least one antigen recognition site for a second antigen. Such antibodies can be produced by recombinant DNA methods or chemically by methods known in the art. Chemically created bispecific antibodies include but are not limited to antibodies that have been reduced and reformed so as to retain their bivalent characteristics and antibodies that have been chemically coupled so that they have at least two antigen recognition sites for each antigen. Bispecific antibodies include all antibodies or conjugates of antibodies, or polymeric forms of antibodies, which are capable of recognizing two different antigens.

According to specific embodiments, the antibody is a monoclonal antibody.

Methods of producing antibodies as well as fragments thereof are well known in the art (See for example, Harlow and Lane, Antibodies: A Laboratory Manual, Cold Spring Harbor Laboratory, New York, 1988, incorporated herein by reference).

According to specific embodiments, the antibody is recombinant produced in mammalian cells.

According to specific embodiments, the antibody is recombinantly produced in bacteria.

Antibody fragments according to some embodiments of the invention can be prepared by proteolytic hydrolysis of the antibody or by expression in E. coli or mammalian cells (e.g. Chinese hamster ovary cell culture or other protein expression systems) of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')2. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly. These methods are described, for example, by Goldenberg, U.S. Pat. Nos. 4,036,945 and 4,331,647, and references contained therein, which patents are hereby incorporated by reference in their entirety. See also Porter, R. R. [Biochem. J. 73: 119-126 (1959)]. Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

Fv fragments comprise an association of VH and VL chains. This association may be noncovalent, as described in Inbar et al. [Proc. Nat'l Acad. Sci. USA 69:2659-62 (19720]. Alternatively, the variable chains can be linked by an intermolecular disulfide bond or cross-linked by chemicals such as glutaraldehyde. Preferably, the Fv fragments comprise VH and VL chains connected by a peptide linker. These single-chain antigen-binding proteins (sFv) are prepared by constructing a structural gene comprising DNA sequences encoding the VH and VL domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by [Whitlow and Filpula, Methods 2: 97-105 (1991); Bird et al., Science 242:423-426 (1988); Pack et al., Bio/Technology 11:1271-77 (1993); and U.S. Pat. No. 4,946,778, which is hereby incorporated by reference in its entirety.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See, for example, Larrick and Fry [Methods, 2: 106-10 (1991)].

According to specific embodiments, the antibody is a chimeric antibody.

According to specific embodiments, the antibody is a humanized antibody. Humanized forms of non-human (e.g., murine) antibodies are chimeric molecules of immunoglobulins, immunoglobulin chains or fragments thereof (such as Fv, Fab, Fab', F(ab').sub.2 or other antigen-binding subsequences of antibodies) which contain minimal sequence derived from non-human immunoglobulin. Humanized antibodies include human immunoglobulins (recipient antibody) in which residues form a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues, which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin [Jones et al., Nature, 321:522-525 (1986); Riechmann et al., Nature, 332:323-329 (1988); and Presta, Curr. Op. Struct. Biol., 2:593-596 (1992)].

Methods for humanizing non-human antibodies are well known in the art. Generally, a humanized antibody has one or more amino acid residues introduced into it from a source, which is non-human. These non-human amino acid residues are often referred to as import residues, which are typically taken from an import variable domain. Humanization can be essentially performed following the method of Winter and co-workers [Jones et al., Nature, 321:522-525 (1986); Riechmann et al., Nature 332:323-327 (1988); Verhoeyen et al., Science, 239:1534-1536 (1988)], by substituting rodent CDRs or CDR sequences for the corresponding sequences of a human antibody. Accordingly, such humanized antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

According to specific embodiments, the antibody is a human antibody.

Human antibodies can also be produced using various techniques known in the art, including phage display libraries [Hoogenboom and Winter, J. Mol. Biol., 227:381 (1991); Marks et al., J. Mol. Biol., 222:581 (1991); Bitton A, Nahary L, Benhar I. Methods Mol Biol. 1701:349-363 (2018)]. The techniques of Cole et al. and Boerner et al. are also available for the preparation of human monoclonal antibodies (Cole et al., Monoclonal Antibodies and Cancer Therapy, Alan R. Liss, p. 77 (1985) and Boerner et al., J. Immunol., 147(1): 86-95 (1991)]. Similarly, human antibodies can be made by introduction of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633, 425; 5,661,016, and in the following scientific publications: Marks et al., Bio/Technology 10: 779-783 (1992); Lonberg et al., Nature 368: 856-859 (1994); Morrison, Nature 368 812-13 (1994); Fishwild et al., Nature Biotechnology 14, 845-51 (1996); Neuberger, Nature Biotechnology 14: 826 (1996); and Lonberg and Huszar, Intern. Rev. Immunol. 13, 65-93 (1995).

It will be appreciated that targeting of particular compartment within the cell can be achieved using intracellular antibodies (also known as "intrabodies"). These are essentially SCA to which intracellular localization signals have been added (e.g., ER, mitochondrial, nuclear, cytoplasmic). This technology has been successfully applied in the art (for review, see Richardson and Marasco, 1995, TIBTECH vol. 13). Intrabodies have been shown to virtually eliminate the expression of otherwise abundant cell surface receptors and to inhibit a protein function within a cell (See, for example, Richardson et al., 1995, Proc. Natl. Acad. Sci. USA 92: 3137-3141; Deshane et al., 1994, Gene Ther. 1: 332-337; Marasco et al., 1998 Human Gene Ther 9: 1627-42; Shaheen et al., 1996 J. Virol. 70: 3392-400; Werge, T. M. et al., 1990, FEBS Letters 274:193-198; Carlson, J. R. 1993 Proc. Natl. Acad. Sci. USA 90:7427-7428; Biocca, S. et al., 1994, Bio/Technology 12: 396-399; Chen, S-Y. et al., 1994, Human Gene Therapy 5:595-601; Duan, L et al., 1994, Proc. Natl. Acad. Sci. USA 91:5075-5079; Chen, S-Y. et al., 1994, Proc. Natl. Acad. Sci. USA 91:5932-5936; Beerli, R. R. et al., 1994, J. Biol. Chem. 269:23931-23936; Mhashilkar, A. M. et al., 1995, EMBO J. 14:1542-1551; PCT Publication No. WO 94/02610 by Marasco et al.; and PCT Publication No. WO 95/03832 by Duan et al.).

According to specific embodiments, the antibody is an intracellular antibody, since IDE is expressed on the cell surface but also in the cytosol, peroxisomes and endosomes.

In this respect, it has been shown that intracellular antibodies can block translocation of proteins to the proper compartment thereby inhibiting their activities (see e.g. Böldicke J. Cell. Mol. Med. Vol 11, No 1, 2007 pp. 54-70; Persic et al. Gene 187 (1997) 1-8; and Shaki-Loewenstein et al. Journal of Immunological Methods 303 (2005) 19-39).

Thus, the intracellular antibody of some embodiments of the present invention does not necessarily need to inhibit the intrinsic catalytic activity of IDE per-se.

To prepare an intracellular antibody expression vector, the cDNA encoding the antibody light and heavy chains specific for the target protein of interest are isolated, typically from a hybridoma that secretes a monoclonal antibody specific for APLP1. Hybridomas secreting anti-APLP1 monoclonal antibodies, or recombinant monoclonal antibodies, can be prepared using methods known in the art. Once a monoclonal antibody specific for the APLP1 protein is identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma-derived antibodies, light and heavy chain cDNAs can be obtained, for example, by PCR amplification or cDNA library screening. For recombinant antibodies, such as from a phage display library, cDNA encoding the light and heavy chains can be recovered from the display package (e.g., phage) isolated during the library screening process and the nucleotide sequences of antibody light and heavy chain genes are determined. For example, many such sequences are disclosed in Kabat, E. A., et al. (1991) Sequences of Proteins of Immunological Interest, Fifth Edition, U.S. Department of Health and Human Services, NIH Publication No. 91-3242 and in the "Vbase" human germline sequence database. Once obtained, the antibody light and heavy chain sequences are cloned into a recombinant expression vector using standard methods.

For cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In another embodiment, the vector encodes a single chain antibody (scFv) wherein the variable regions of the light and heavy chains are linked by a flexible peptide linker [e.g., $(Gly_4Ser)_3$ and expressed as a single chain molecule. To inhibit APLP1 activity in a cell, the expression vector encoding the intracellular antibody is introduced into the cell by standard transfection methods, as discussed hereinbefore.

In some embodiments, the antibody provided herein can be functionally associated with a cell-penetrating agent. As used herein the phrase "cell penetrating agent" refers to an agent, which enhances translocation of the antibody across a cell membrane.

An exemplary cell-penetrating agent is a cell-penetrating peptide.

As used herein, a "cell-penetrating peptide" is a peptide that comprises a short (about 12-30 residues) amino acid sequence or functional motif that confers the energy-independent (i.e., non-endocytotic) translocation properties associated with transport of the membrane-permeable complex across the plasma and/or nuclear membranes of a cell. The cell-penetrating peptide used in the membrane-permeable complex of some embodiments of the invention preferably comprises at least one non-functional cysteine residue, which is either free or derivatized to form a disulfide link with a double-stranded ribonucleic acid that has been modified for such linkage. Representative amino acid motifs conferring such properties are listed in U.S. Pat. No. 6,348,185, the contents of which are expressly incorporated herein by reference. The cell-penetrating peptides of some embodiments of the invention may include, but are not limited to, penetratin, transportan, pIsl, TAT(48-60), pVEC, MTS, and MAP.

Additionally or alternatively, lipid particles such as liposomes may be used as cell penetrating agents.

Liposomes include any synthetic (i.e., not naturally occurring) structure composed of lipid bilayers, which enclose a volume. Liposomes include emulsions, foams, micelles, insoluble monolayers, liquid crystals, phospholipid dispersions, lamellar layers and the like. The liposomes may be prepared by any of the known methods in the art [Monkkonen, J. et al., 1994, J. Drug Target, 2:299-308; Monkkonen, J. et al., 1993, Calcif. Tissue Int., 53:139-145; Lasic D D., Liposomes Technology Inc., Elsevier, 1993, 63-105. (chapter 3); Winterhalter M, Lasic D D, Chem Phys Lipids, 1993 September; 64(1-3):35-43]. The liposomes may be positively charged, neutral or negatively charged.

Any method known in the art can be used to incorporate an antibody into a liposome as described e.g. by Alfonso et al., [The science and practice of pharmacy, Mack Publishing, Easton Pa. 19$^{th}$ ed., (1995)] and those described by Kulkarni et al., [J. Microencapsul. 1995, 12 (3) 229-46].

In order to determine liposomes that are especially suitable in accordance with the present invention a screening assay can be performed such as the assays described in U.S. Pat. Appl. No. 20040266734 and U.S. Pat. Appl. No. 20040266734; and in Danenberg et al., Journal of cardiovascular pharmacology 2003, 42:671-9; Circulation 2002, 106:599-605; Circulation 2003, 108:2798-804.

According to one embodiment, antibodies of some embodiments of the present invention are produced as follows. Purified IDE is used to isolate specific single-chain variable fragment (scFv) clones that recognize epitopes of the human IDE. Phage display technique is utilized using a human synthetic antibody phage display library. Specifically, a human scFv library, e.g., the Ronit 1 library [described in Azriel-Rosenfeld et al. J Mol Biol. (2004) 335 (1):177-192, fully incorporated herein by reference], is screened. The library is subjected to depletion of non-specific proteins and proteins purified from bacteria using affinity columns, and selection is made using the recombinant human wild type (WT) IDE (SEQ ID NO: 50). In several cycles (e.g. two cycles) the enriched phage are depleted (i.e. negative selection) on mutated IDE (e.g. E111Q) in order to enrich positive phages which recognize the WT IDE or according to a specific embodiment better than the mutated IDE. Each of these depletion steps are followed by a selection step (i.e. positive selection) on WT IDE. After the affinity selection cycles, individual clones of infected bacteria are picked and grown. Phages from each clone are then tested (e.g. by ELISA) for IDE binding versus non-specific proteins as negative controls. Positive clones are analyzed by PCR amplification followed by fingerprinting in order to detect different clones, and are further sequenced to verify integrity and difference between clones.

An important feature of the isolation of the antibodies of some embodiments of the invention is the selection step. Thus according to one embodiment, the method of producing an antibody comprises (a) providing a plurality of antibodies (e.g. as described above); and (b) screening the antibodies to select antibodies which bind wild type IDE and not mutated IDE having a reduced catalytic activity compared to the wild type IDE.

Once antibodies are obtained, they may be tested for activity. Methods of testing antibody activity include e.g. enzyme-linked immunosorbent assay (ELISA) and in-vitro insulin degradation assay.

According to specific embodiments, the antibodies are tested for IDE inhibitory activity. IDE inhibitory activity refers to specifically down-regulating the enzymatic activity of IDE. For instance, the $IC_{50}$ of IDE is in the range of 10-200 nM (e.g. 1-100 nM, 1-50 nM, 1-20 nM or 1-10 nM) as assayed for the IDE inhibitory peptide ADT-21.

According to exemplary embodiments, the antibody is capable of down-regulating by at least 5%, at least 10%, at least 15%, at least 20%, at least 30%, at least 40%, at least 50%, at least 60%, at least 70%, at least 80%, at least 90% or at least 100% the enzymatic activity of IDE.

According to exemplary embodiments, the antibody is capable of down-regulating by at least 5%, at least 10%, at least 15%, at least 20%, at least 30%, at least 40%, at least 50%, at least 60%, at least 70%, at least 80%, at least 90% or at least 100% the insulin degrading activity of IDE.

According to a specific embodiment, the antibody is capable of down-regulating by at least 50% the insulin degrading activity of IDE.

According to exemplary embodiments, the antibody is capable of down-regulating the insulin degrading activity of IDE by 5-10%, by 10-20%, by 20-30%, by 30-40%, by 40-50%, by 50-60%, by 60-70%, by 70-80%, by 80-90%, by 90-100%, by 10-50%, 50-100% or by 10-100%.

According to exemplary embodiments, the antibody is capable of down-regulating the activity of IDE such that IDE degrades insulin at a rate of 25-50 μmole, 25-75 μmole, 25-100 μmole, 50-75 μmole, 50-100 μmole or 75-100 μmole of human recombinant IDE degrades 1 μmole human Insulin/min.

As mentioned hereinabove, according to specific embodiments, the antibodies (e.g. Single chain Fv's) may be produced by recombinant DNA technology whereby a nucleic acid of the antibody is ligated into an expression vector, which is subsequently introduced into a host cell.

Thus, according to an aspect of the present invention there is provided an isolated polynucleotide comprising a nucleic acid sequence encoding the antibody of some embodiments of the invention.

According to one embodiment of the present invention, the nucleic acid sequence of the antibody comprises SEQ ID NOs: 3, 5, 7, 11, 13 and 15.

According to another embodiment of the present invention, the nucleic acid sequence of the antibody comprises SEQ ID NOs: 19, 21, 23, 27, 29 and 31.

According to yet another embodiment of the present invention, the nucleic acid sequence of the antibody comprises SEQ ID NOs: 35, 37, 39, 43, 45 and 47.

Non-limiting Examples of nucleic acid sequences encoding the light chain, the heavy chain, the CDRs and variable regions that make up an antibody that can be used with some embodiments of the present invention are provided in SEQ ID NO: 1, 9, 17, 25, 33 and 41.

Thus, according to specific embodiments, the polynucleotide comprises a nucleic acid sequence having at least 80%, at least 85%, at least 90%, at least 95%, at least 97%, at least 98%, at least 99% or 100% identity to a nucleic acid sequence selected from the group consisting of SEQ ID NO: 1, 9, 17, 25, 33 and 41, each possibility represents a separate embodiment of the present invention.

As used herein the term "polynucleotide" or "nucleic acid sequence" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

To express exogenous antibody in mammalian cells, a polynucleotide sequence encoding the antibody is preferably ligated into a nucleic acid construct suitable for mammalian cell expression.

Thus, according to an aspect of the present invention there is provided a nucleic acid construct comprising the isolated polynucleotide.

Such a nucleic acid construct or system includes at least one cis-acting regulatory element for directing expression of the nucleic acid sequence. Cis-acting regulatory sequences include those that direct constitutive expression of a nucleotide sequence as well as those that direct inducible expression of the nucleotide sequence only under certain conditions. Thus, for example, a promoter sequence for directing transcription of the polynucleotide sequence in the cell in a constitutive or inducible manner is included in the nucleic acid construct. Of note the nucleic acid sequences of the present invention may also be used for in-vivo use where they are administered to a subject in need thereof (e.g., diabetic subject) as a naked DNA or ligated into a nucleic acid construct useful for gene therapy e.g., viral vector.

Also provided are host cells which comprise the polynucleotides/expression vectors as described herein.

Such cells are typically selected for high expression of recombinant proteins (e.g., bacterial, plant or eukaryotic cells e.g., CHO, HEK-293 cells), but may also be an immune cell (e.g., macrophages, dendritic cells, T cells, B cells or NK cells) when for instance the CDRs of the agent are implanted in a T Cell Receptor or CAR transduced in said cells which are used in adoptive cell therapy.

Hence, according to an aspect of the present invention there is provided a method of producing an anti-IDE antibody, the method comprising expressing in a host cell the polynucleotide/expression construct.

Yet still when the antibody is produced in vitro, according to specific embodiments, recovery or isolation of the recombinant antibody is effected following an appropriate time in culture. The phrase "recovering the recombinant antibody" or "isolating the recombinant antibody" refers to collecting the whole fermentation medium containing the antibody and need not imply additional steps of separation or purification. Alternatively, "recovering the recombinant antibody" or "isolating the recombinant antibody" refers to recovering the product from a lysate of the producing cells. Notwithstanding the above, antibodies of some embodiments of the invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. According to a specific embodiment the antibody is at least 80%, 85%, 90%, 95%, 97% purified. As used herein, purified means that the composition comprising the purified antibody is free of other proteinaceous substances, which are not the antibody of interest.

As described in the Examples section which follows, using the methodology described herein a number of anti-IDE antibodies were produced.

Thus, according to an aspect of the present invention, there is provided an isolated antibody comprising an antigen recognition region, which comprises the complementarity determining region (CDR) amino acid sequences as set forth in SEQ ID NOs: 4, 6, 8, 12, 14, and 16. According to one embodiment, SEQ ID NO: 4, SEQ ID NO: 6 and SEQ ID NO: 8 are arranged in a sequential order (N>C, as CDRs 1-3, respectively) on a heavy chain of the antibody, while SEQ ID NO: 12, SEQ ID NO: 14 and SEQ ID NO: 16 are arranged in a sequential order (N>C, as CDRs 1-3, respectively) on a light chain of the antibody.

According to some embodiments of the invention, the heavy chain of the antibody comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, e.g., 100% sequence homology or identity to the amino acid sequence set forth in SEQ ID NO: 2.

Thus, according to an aspect of the present invention, there is provided an isolated antibody comprising an antigen recognition region, which comprises the complementarity determining region (CDR) amino acid sequences as set forth in SEQ ID NOs: 20, 22, 24, 28, 30 and 32.

According to a specific embodiment, SEQ ID NO: 20, SEQ ID NO: 22 and SEQ ID NO: 24 are arranged in a sequential order (N>C, as CDRs 1-3, respectively) on a heavy chain of the antibody, while SEQ ID NO: 28, SEQ ID NO: 30 and SEQ ID NO: 32 are arranged in a sequential order (N>C, as CDRs 1-3, respectively) on a light chain of the antibody.

According to some embodiments of the invention, the heavy chain of the antibody comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, e.g., 100% sequence homology or identity to the amino acid sequence set forth in SEQ ID NO: 18.

Thus, according to an aspect of the present invention, there is provided an isolated antibody comprising an antigen recognition region, which comprises the complementarity determining region (CDR) amino acid sequences as set forth in SEQ ID NOs: 36, 38, 40, 44, 46 and 48.

According to a specific embodiment, SEQ ID NO: 36, SEQ ID NO: 38 and SEQ ID NO: 40 are arranged in a sequential order (N>C, as CDRs 1-3, respectively) on a heavy chain of the antibody, while SEQ ID NO: 44, SEQ ID NO: 46 and SEQ ID NO: 48 are arranged in a sequential order (N>C, as CDRs 1-3, respectively) on a light chain of the antibody.

According to some embodiments of the invention, the heavy chain of the antibody comprises an amino acid sequence having at least 80%, at least 81%, 82%, 83%, 84%, 85%, 86%, 87%, 88%, 89%, 90%, 91%, 92%, 93%, 94%, 95%, 96%, 97%, 98%, 99%, e.g., 100% sequence homology or identity to the amino acid sequence set forth in SEQ ID NO: 34.

Homology (e.g., percent homology, identity+similarity) can be determined using any homology comparison software, including for example, the BlastP or TBLASTN software of the National Center of Biotechnology Information (NCBI) such as by using default parameters, when starting from a polypeptide sequence; or the tBLASTX algorithm (available via the NCBI) such as by using default parameters, which compares the six-frame conceptual translation products of a nucleotide query sequence (both strands) against a protein sequence database.

For example, default parameters for tBLASTX include: Max target sequences: 100; Expected threshold: 10; Word size: 3; Max matches in a query range: 0; Scoring parameters: Matrix—BLOSUM62; filters and masking: Filter—low complexity regions.

The antibodies of some embodiments of the present invention may be used for treating a disease associated with an IDE activity in a subject in need thereof.

Thus, according to an aspect of the present invention, there is provided a method for treating a disease associated with an IDE activity in a subject in need thereof, the method comprising administering to the subject a therapeutically effective amount of the antibody (ii) or (iii) described herein, thereby preventing or treating the disease associated with the IDE activity.

According to an additional or an alternative aspect of the present invention, there is provided the antibody (ii) or (iii) disclosed herein for use in treating a disease associated with an IDE activity in a subject in need thereof.

In this respect, as noted hereinabove, since IDE is expressed on the cell surface but also in the cytosol, peroxisomes and endosomes, an antibody of some embodiments capable of penetrating into cells (either an intracellular antibody or an antibody functionally associated with a cell penetrating agent) can inhibit IDE activity by blocking its translocation to the proper compartment; and thus does not necessarily need to inhibit the intrinsic catalytic activity of IDE per-se in order to treat a disease associated with an IDE activity.

Thus, according to an aspect of the present invention, there is provided a method of treating a disease associated with an IDE activity in a subject in need thereof, the method comprising administering to the subject a therapeutically effective amount of an antibody comprising an antigen recognition region which specifically binds IDE, wherein said antigen recognition domain comprises CDR amino acid sequences as set forth in:

(i) SEQ ID NOs: 4 (CDR1), 6 (CDR2) and 8 (CDR3), being sequentially arranged from N to C on a heavy chain of said antibody; and 12 (CDR1), 14 (CDR2) and 16 (CDR3), being sequentially arranged from N to C on a light chain of said antibody;

(ii) SEQ ID NOs: 20 (CDR1), 22 (CDR2) and 24 (CDR3), being sequentially arranged from N to C on a heavy chain of said antibody; and 28 (CDR1), 30 (CDR2) and 32 (CDR3), being sequentially arranged from N to C on a light chain of said antibody; or (iii) SEQ ID NOs: 36 (CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody, wherein when said antibody is said antibody (iii) said antibody is an intracellular antibody or is functionally associated to a cell penetrating agent, thereby preventing or treating the disease associated with the IDE activity.

According to an additional or an alternative aspect of the present invention, there is provided an antibody comprising an antigen recognition region which specifically binds IDE, wherein said antigen recognition domain comprises CDR amino acid sequences as set forth in:

(i) SEQ ID NOs: 4 (CDR1), 6 (CDR2) and 8 (CDR3), being sequentially arranged from N to C on a heavy chain of said antibody; and 12 (CDR1), 14 (CDR2) and 16 (CDR3), being sequentially arranged from N to C on a light chain of said antibody;

(ii) SEQ ID NOs: 20 (CDR1), 22 (CDR2) and 24 (CDR3), being sequentially arranged from N to C on a heavy chain of said antibody; and 28 (CDR1), 30 (CDR2) and 32 (CDR3), being sequentially arranged from N to C on a light chain of said antibody; or (iii) SEQ ID NOs: 36 (CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody, wherein when said antibody is said antibody (iii) said antibody is an intracellular antibody or is functionally associated to a cell penetrating agent, for use in treating a disease associated with an IDE activity in a subject in need thereof.

As used herein a "disease associated with IDE activity" refers to a medical condition, disease or syndrome in which IDE activity contributes to onset or progression.

As previously mentioned, IDE is an enzyme which cleaves multiple small proteins of diverse sequences including insulin, amyloid β-protein (Aβ), glucagon, amylin, atrial natriuretic factor and calcitonin. Thus, in situations in which increased levels of these substrates may aid in symptom alleviation and even cure the disease, the antibodies of some embodiments of the present invention may be employed.

According to a specific embodiment, an increase in the levels of insulin is warranted for the treatment of a disease or disorder.

Such diseases and disorders include, but are not limited to, autoimmune diseases of the central nervous system, neurodegenerative diseases, metabolic syndrome, diabetes, obesity, hyperglycemia, retinal damage, renal failure, nerve damage, microvascular damage, varicella-zoster virus (VZV) infection and wounds. As used herein "an autoimmune disease of the central nervous system" refers to a disease where the body's immune system attacks its own nervous system (preferably CNS).

Examples of autoimmune diseases of the CNS include, but are not limited to, multiple sclerosis, Guillain-Barre syndrome, Lambert-Eaton myasthenic syndrome, Myasthenia gravis, transverse myelitis, progressive multifocal leukoencephalopathy, chronic headache, cerebral palsy, lupus, immune dysfunction muscular central nervous system breakdown, primary CNS vasculitis, autoimmune cerebellar degeneration, gait ataxia with late age onset polyneuropathy (GALOP), neuromyelitis optica, Stiff Person Syndrome and HTLV-1-associated myelopathy (HAM)/tropical spastic paraparesis (TSP).

According to specific embodiments, the autoimmune disease of the central nervous system is selected from the group consisting of multiple sclerosis, Guillain-Barre syndrome, Lambert-Eaton myasthenic syndrome, Myasthenia gravis, transverse myelitis, progressive multifocal leukoencephalopathy, chronic headache and cerebral palsy.

According to a specific embodiment, the autoimmune disease of the central nervous system comprises multiple sclerosis (MS).

As used herein "a neurodegenerative disease" refers to a disorder, disease or condition of the nervous system (preferably CNS) which is characterized by gradual and progressive loss of neural tissue, neurotransmitter, or neural functions.

Examples of neurodegenerative disorder include, but are not limited to, amyotrophic lateral sclerosis (ALS or Lou Gehrig's Disease), autoimmune encephalomyelitis, degenerative nerve diseases, encephalitis (e.g. Rasmussen's encephalitis), Alzheimer's disease, epilepsy, genetic brain disorders, stroke, Parkinson's disease and Huntington's disease.

According to a specific embodiment, the neurodegenerative disease is Parkinson's disease.

According to a specific embodiment, the neurodegenerative disease is Alzheimer's disease.

According to specific embodiments, the disease is selected from the group consisting of a metabolic syndrome, a diabetes and an obesity.

According to specific embodiments, the disease is metabolic syndrome.

As used herein, the term "metabolic syndrome", refers to a group or clustering of metabolic conditions [abdominal obesity, elevated fasting glucose, "dyslipidemia" (i.e., elevated lipid levels) and elevated blood pressure (HBP)] which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of atherosclerotic disease due to the pressure of the component risk factors.

According to specific embodiments, the disease is diabetes.

As used herein "diabetes" refers to a disease resulting either from an absolute deficiency of insulin (type 1 diabetes) due to a defect in the biosynthesis or production of insulin, or a relative deficiency of insulin in the presence of insulin resistance (type 2 diabetes), i.e., impaired insulin action, in an organism. The diabetic patient thus has absolute or relative insulin deficiency, and may display, among other symptoms and signs, elevated blood glucose concentration, presence of glucose in the urine, excessive discharge of urine (polyuria), increased thirst (polydipsia) and increased hunger (polyphagia). Symptoms may develop quite rapidly (e.g. within weeks or months) in type 1 diabetes, particularly in children. However, in type 2 diabetes symptoms may develop much more slowly and may be subtle or completely absent. Diabetes (both types) may also cause a rapid yet significant weight loss (despite normal or even increased eating) and irreducible mental fatigue. Diabetes as used herein encompasses any stage or type of diabetes, including, but not limited to, overt diabetes, pre diabetes and Latent autoimmune diabetes of adults (LADA).

According to specific embodiments, the diabetes if type 1 diabetes.

According to other specific embodiments, the diabetes if type 2 diabetes.

Examples of diabetes related diseases include, but are not limited to, diabetes type I, diabetes type II, gestational diabetes, insulin resistance, obesity, hyperglycemia, eye disorders (e.g. glaucoma, cataract), skin infections, hypertension, gastroparesis, ketoacidosis (DKA), neuropathy (e.g. diabetic neuropathy), hyperosmolar hyperglycemic nonketotic syndrome (HHNS), kidney disease (nephropathy) and peripheral arterial disease (PAD). According to other specific embodiments, the disease is a wound.

The term "wound" as used herein refers broadly to injuries to the skin and subcutaneous tissue as well as internal organs initiated in any one of a variety of ways (e.g., pressure sores from extended bed rest, wounds induced by trauma, wounds received during or following a surgical procedure and the like) and with varying characteristics. Exemplary examples include, but are not limited to, bruises, scrapes, burn wounds, sunburn wounds, incisional wounds, excisional wounds, surgical wounds, necrotizing fascitis, ulcers, venous stasis ulcers, diabetic ulcers, decubitus ulcers, aphthous ulcers, pressure ulcers, scars, alopecia areata, dermatitis, allergic contact dermatitis, atopic dermatitis, berloque dermatitis, diaper dermatitis, dyshidrotic dermatitis, psoriasis, eczema, erythema, warts, anal warts, angioma, cherry angioma, athlete's foot, atypical moles, basal cell carcinoma, Bateman's purpura, bullous pemphigoid, candida, chondrodermatitis helicis, Clark's nevus, cold sores, condylomata, cysts, Darier's disease, dermatofibroma, Discoid Lupus Erythematosus, nummular eczema, atopic eczema, dyshidrotic eczema, hand eczema, Multiforme Erythema Nodosum, Fordyce's Condition, Folliculitis Keloidalis Nuchae, Folliculitis, Granuloma Annulare, Grover's Disease, heat rash, herpes simplex, herpes zoster (shingles), Hidradenitis Suppurativa, Hives, Hyperhidrosis, Ichthyosis, Impetigo, Keratosis Pilaris, Keloids, Keratoacanthoma, Lichen Planus, Lichen Planus Like Keratosis, Lichen Simplex Chronicus, Lichen Sclerosus, Lymphomatoid Papulosis, Lupus of the Skin, Lyme Disease, Lichen Striatus, Myxoid Cysts, Mycosis Fungoides, Molluscum Contagiosum, Moles, Nail Fungus, Necrobiosis Lipoidica Diabeticorum, Nummular Dermatitis, Onychoschizia, Onychomycosis, Pityriasis Lichenoides, Pityriasis Rosea, Pityriasis Rubra Pilaris, Plantar Warts, Poison Ivy, Poison Oak, Pompholyx, Pseudofolliculitis Barbae, Pruritus Ani and Pityriasis Alba. Wounds are typically classified into one of four grades depending on the depth of the wound: (i) Grade I: wounds limited to the epithelium; (ii) Grade II: wounds extending into the dermis; (iii) Grade III: wounds extending into the subcutaneous tissue; and (iv) Grade IV (or full-thickness wounds): wounds wherein bones are exposed (e.g., a bony pressure point such as the greater trochanter or the sacrum).

The term "partial thickness wound" used herein refers to wounds that encompass Grades I-III; examples of partial thickness wounds include burn wounds, pressure sores, venous stasis ulcers, and diabetic ulcers.

The term "deep wound" used herein is meant to include both Grade III and Grade IV wounds.

The term "chronic wound" used herein refers to a wound that has not healed within thirty days.

The term "healing" in respect to a wound refers to the process of repairing a wound such as by scar formation (in exemplary embodiments healing is devoid of fibrotic tissue formation).

In a specific embodiment, compositions of some embodiments of the present invention promote i.e., accelerate the healing process.

The phrase "inducing or accelerating a healing process of a skin wound" refers to either the induction of the formation of granulation tissue of wound contraction and/or the induction of epithelialization (i.e., the generation of new cells in the epithelium). Wound healing is conveniently measured by decreasing wound area.

Specific embodiments of the present invention contemplates treating all wound types, including deep wounds, acute wounds, chronic wounds, diabetic-relates wounds, ischemic wounds, ulcers, burns and surgical wounds.

According to specific embodiments, the wound is selected from the group consisting of a chronic wound, an acute wound, a diabetic wound, an ischemic wound, an ulcer, a burn and a surgical wound.

Additional diseases and disorders which may be treated according to specific embodiments include, but are not limited to, nonketotic hyperosmolar coma, viral infection [e.g. varicella-zoster virus (VZV)], atherosclerosis, hypertension, cardiovascular diseases such as congenital heart defects, cardiomyopathy, aortic stenosis, atrial septal defect (ASD), atrioventricular (A-V) canal defect, ductus arteriosus, pulmonary stenosis, subaortic stenosis, ventricular septal defect (VSD), valve diseases, myocardial infarction, tuberous sclerosis, scleroderma, transplantation, endometriosis, fertility, Von Hippel-Lindau (VHL) syndrome, cirrhosis, transplantation, hemophilia, hypercoagulation, idiopathic thrombocytopenic purpura, immunodeficiencies, retinitis pigmentosa, autosomal dominant; retinitis pigmentosa, autosomal recessive; SEMD, Pakistani type; urofacial syndrome; cholesteryl ester storage disease; corneal dystrophy, Thiel-Behnke type; Dubin-Johnson syndrome; leukemia, T-cell acute lymphocytic; Leukemia, T-cell acute lymphocytic; Spinocerebellar ataxia, infantile-onset, with sensory neuropathy; Split hand/foot malformation, type 3; Tolbutamide poor metabolizer; Warfarin sensitivity; Wolman disease; anterior segment mesenchymal dysgenesis and cataract; cataract, congenital; neurofibrosarcoma, retinal damage such as nonproliferative diabetic retinopathy (NPDR) and proliferative diabetic retinopathy (PDR), chronic renal failure, diabetic nephropathy, nerve damage such as diabetic neuropathy, microvascular damage, diabetes related foot ulcers and graft versus host disease.

The term "treating" refers to inhibiting, preventing or arresting the development of a pathology (disease, disorder or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. It will be appreciated that the treating may be performed alone or in conjunction with other therapies.

As used herein, the term "preventing" refers to keeping a disease, disorder or condition from occurring in a subject who may be at risk for the disease, but has not yet been diagnosed as having the disease.

As used herein, the term "subject" refers to a mammalian subject (e.g., human being) of any gender and any age including neonatal, infant, juvenile, adolescent, adult and elderly adult.

According to specific embodiments, the subject is diagnosed, suffers or predisposed to the above-mentioned medical conditions.

According to specific embodiments, the subject has a level of IDE above a predetermined threshold in a biological sample as compared to a control biological sample, as further described hereinbelow.

Hence, according to specific embodiments, the method disclosed herein comprises determining the level of IDE in a biological sample of the subject using the antibody disclosed herein prior to the administering.

The antibodies of some embodiments of the present invention can be administered to the subject per se or as part of a pharmaceutical composition.

According to an aspect of the present invention, there is provided a pharmaceutical composition comprising as an active ingredient antibody (ii) or (iii) disclosed herein and a pharmaceutically acceptable carrier.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the antibody accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, PA, latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into a tissue region of a patient.

According to a specific embodiment of the present invention, the antibody is administered via nasal administration.

According to a specific embodiment of the present invention, the antibody is administered via subcutaneous administration.

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations, which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions, which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents, which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (i.e., antibody) effective to prevent, alleviate or ameliorate symptoms of a disorder (e.g., IDE related disease) or prolong the survival of the subject being treated.

According to an embodiment of the present invention, a therapeutically effective amount results in an increase in blood insulin levels of the subject following administration.

According to another embodiment of the present invention, a therapeutically effective amount results in reduction in pancreatic beta cell destruction in the subject following administration.

According to another embodiment of the present invention, a therapeutically effective amount results in an increase in blood Insulin growth factor 1 (IGF1) levels of the subject following administration.

According to another embodiment of the present invention, a therapeutically effective amount results in reduction in secretion of IL-17 from T lymphocytes of the subject following administration.

According to another embodiment of the present invention, a therapeutically effective amount results in reduction in secretion of IFN-γ from T lymphocytes of the subject following administration.

Assessing the levels of insulin, IGF1, IL-17 or IFN-γ may be carried out using any method known to one of skill in the art, including for example, by ELISA.

Assessing destruction of pancreatic beta cells may be carried out using any method known to one of skill in the art, including for example, by measuring β cell function (e.g. by measuring the levels of metabolic markers such as C-peptide) or by imaging β cell mass [e.g. by emission tomography (PET) or by single-photon emission computed tomography (SPECT)], as taught by Lebastchi J. and Herold K. C., Cold Spring Harb Perspect Med. June 2012; 2(6): a007708, incorporated herein by reference.

According to another embodiment of the present invention, a therapeutically effective amount results in inhibition or reduction of IDE activity. Reduction or inhibition of IDE activity may comprise at least about 10%, 20%, 30%, 40%, 50%, 60%, 70%, 80%, 90% or 100% reduction in IDE activity. Assessing the reduction of IDE activity may be carried out using any method known to one of skill in the art, including for example, by Fluorometric IDE activity assay or by In-vitro Insulin and IGF-1 degradation assays, as described in detail in the Examples section, which follows.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide sufficient plasma levels of the active ingredient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

For example, according to one embodiment, an antibody of the present invention may be administered intravenously (i.v.) at a dose between 0.1 mg/kg to 10 mg/kg, 0.1 mg/kg to 5 mg/kg, 0.1 mg/kg to 1 mg/kg, at a dose between 1 mg/kg to 10 mg/kg, at a dose between 1 mg/kg to 5 mg/kg, at a dose between 2.5 mg/kg to 5 mg/kg, at a dose between 0.5 mg/kg to 5 mg/kg or at a dose between 5 mg/kg to 10 mg/kg. According to another embodiment, the antibody of the present invention may be administered i.v. at a dose of 10 mg/kg to 100 mg/kg, at a dose of 10 mg/kg to 50 mg/kg, at a dose of 25 mg/kg to 50 mg/kg or at a dose of 50 mg/kg to 100 mg/kg. According to yet another embodiment, the antibody of the present invention may be administered i.v. at a dose of 100 mg/kg to 1000 mg/kg, at a dose of 100 mg/kg to 500 mg/kg, at a dose of 250 mg/kg to 500 mg/kg or at a dose of 500 mg/kg to 1000 mg/kg.

It will be appreciated that animal models exist by which the antibodies of the present invention may be tested prior to human treatment. For example, a STZ-induce or a non-obese diabetic (NOD) mouse model of diabetes may be utilized as a model for diabetes. Multiple sclerosis animal models include e.g. the murine EAE model (e.g. induction of disease in NOD mice by immunization with MOG (35-55) in CFA). Alzheimer's disease animal models include e.g. APP/PSI mice and Samaritan Alzheimer's Rat Model (available from Samaritan Pharmaceuticals). For wound healing, a diabetic mouse wound model may be utilized as previously taught by Galeano et al., Diabetes. (2004) 53(9):2509-17 (incorporated herein by reference) or a diabetic rat model may be utilized as previously taught by Qiu et al., J Surg Res. (2007) 138(1):64-70 (incorporated herein by reference). Parkinson's disease animal models include e.g. the A53T Tg mice expressing human mutated alpha-synuclein in CNS neurons (Giasson et al. 2002), and the C57BL/6-Tg(Thy1-SNCA*E35K*E46K*E61K)3798Nuber/J (Nuber et al., 2018).

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary adminis-tration. Such notice, for example, may be of labeling approved by the U.S. Food and Drug Administration for prescription drugs or of an approved product insert. Com-positions comprising a preparation of the invention formu-lated in a compatible pharmaceutical carrier may also be prepared, placed in an appropriate container, and labeled for treatment of an indicated condition, as is further detailed above.

It will be appreciated that the therapeutic compositions of the invention may comprise, in addition to the antibodies, other known medications or therapeutic agents for the treatment of IDE related diseases (e.g. diabetes, autoimmune diseases of the CNS, neurodegenerative diseases) such as, but not limited to, steroids, corticosteroids, immunosuppres-sant drugs, antihistamine drugs and the like. These medica-tions may be included in an article of manufacture in a single or in separate packagings.

Hence, according to an aspect of the present invention, there is provided an article of manufacture identified for the treatment of a disease associated with an IDE activity comprising antibody (ii) or (iii) disclosed herein and a therapeutic agent for treating said disease.

According to specific embodiments, the antibody and the therapeutic agent are in separate containers.

According to other specific embodiments, the antibody and the therapeutic agent are in a co-formulation.

Further, according to specific embodiments, the methods and uses disclosed herein further comprise administering to the subject a therapeutic agent (other than the antibodies disclosed herein) for treating the disease.

As shown in the Examples section which follows, the present inventors have developed a highly sensitive ELISA using the generated antibodies and used this ELISA to demonstrate a strong correlation between human serum IDE levels and presence and/or severity of metabolic syndrome, hence specific embodiments of the present invention further propose analyzing for the level of IDE for the purpose of diagnosing, monitoring treatment efficacy and/or determin-ing treatment.

Hence, according to an aspect of the present invention, there is provided a method of diagnosing a disease associ-ated with an IDE activity in a subject, the method compris-ing determining a level of IDE in a biological sample of the subject using the antibody disclosed herein, wherein when said level of said IDE is above a predetermined threshold as compared to a control biological sample, the subject is diagnosed with the disease.

As used herein the term "diagnosing" refers to determin-ing presence or absence of a pathology (i.e. cancer belong-ing to the Ewing family of tumors), classifying a pathology or a symptom, determining a severity of the pathology (e.g. grade or stage), monitoring pathology progression, forecast-ing an outcome of a pathology and/or prospects of recovery and screening of a subject for a specific disease.

Hence, according to an aspect of the present invention, there is provided a method of prognosing a disease associ-ated with an IDE activity in a subject, the method compris-ing determining a level of IDE in a biological sample of a subject diagnosed with the disease using the antibody dis-closed, wherein when said level of said IDE is above a predetermined threshold as compared to a control biological sample the prognosis is poor prognosis.

According to specific embodiments, the method (e.g. the determining, the contacting) is effected in-vitro or ex-vivo.

According to specific embodiments, the method disclosed herein comprises obtaining the biological sample prior to the determining.

Non-limiting examples of biological samples that can be used with some embodiments of the invention include, a cell or cells obtained from any tissue biopsy, a tissue, an organ, a blood cell, a bone marrow cell, body fluids such as blood, serum, plasma and rinse fluid that may have been in contact with the diseased cells/tissue.

The biological sample can be obtained using methods known in the art such as using a syringe with a needle, a scalpel, fine needle biopsy, needle biopsy, core needle biopsy, fine needle aspiration (FNA), surgical biopsy, buccal smear, lavage and the like.

According to specific embodiments, the protein molecules are extracted from the biological sample of the subject. Thus, according to specific embodiments, the method further comprises extracting a protein from the biological sample prior to the determining. Methods of extracting protein molecules from biological samples are well known in the art.

As used herein the phrase "predetermined threshold" refers to a level of IDE that characterizes a healthy sample or a sample with a known disease prognosis of the same origin assayed under the same conditions. Such a level can be experimentally determined by comparing samples with known levels of IDE (e.g., samples obtained from healthy subjects or from subject with a known disease prognosis) to samples derived from subjects diagnosed with the disease associated with IDE activity. Alternatively, such a level can be obtained from the scientific literature and from databases.

According to specific embodiments, the predetermined threshold is derived from a control sample.

Several control samples can be used with specific embodi-ments of the present invention.

Since biological characteristics depend on, amongst other things, species and age, it is preferable that the control sample is obtained from a subject of the same species, age, gender and from the same sub-population (e.g. smoker/ nonsmoker).

According to specific embodiments, the control sample comprises a biological sample of the same type as the biological sample of the subject.

According to specific embodiments, the control sample is a healthy control sample.

According to specific embodiments, the control sample is a sample of a subject having a mild disease or a disease with goo prognosis.

According to specific embodiments, the control sample is obtained from the scientific literature or from a database.

According to specific embodiments, the increase/decrease above or below a predetermined threshold is statistically significant.

According to specific embodiments, the predetermined threshold is at least 1.5 fold, at least 2 fold, at least 3 fold, at least 5 fold, at least 10 fold, or at least 20 fold as compared the level IDE in a control sample as measured using the same assay such as western blot, ELISA, IP.

According to specific embodiments, the predetermined threshold is at least 1.5 fold as compared the level of IDE in a control sample.

According to specific embodiments, the predetermined threshold is at least 2%, at least 5%, at least 10%, at least 20%, at least 30%, at least 40%, at least 50%, at least 60%, at least 70%, at least 80%, at least 90%, e.g., 100%, at least 200%, at least 300%, at least 400%, at least 500%, at least 600% as compared the level of IDE in a control sample.

According to specific embodiments, the level of IDE can be determined in the biological sample using any method known in the art which utilizes the antibodies disclosed herein, such as, but not limited to ELISA, western blot, IP.

Thus, according to some embodiments, detection of the level of IDE is performed by contacting the biological sample, the tissue, the cell, or fractions or extracts thereof with the antibody disclosed herein.

According to specific embodiments, the contacting is effected under conditions which allow the formation of a complex comprising IDE present in the biological sample and the antibody (i.e. immunocomplex).

The immunocomplex can be formed at a variety of temperatures, salt concentration and pH values which may vary depending on the method and the biological sample used and those of skills in the art are capable of adjusting the conditions suitable for the formation of each immunocomplex.

Thus, according to an aspect of the present invention there is provided a composition of matter comprising a biological sample of a subject (or a lysate of a biological sample of a subject) diagnosed with a disease associated with an IDE activity, and the antibody disclosed herein.

According to an additional or an alternative aspect of the present invention there is provided an article of manufacture comprising a biological sample of a subject (or a lysate of a biological sample of a subject) diagnosed with a disease associated with an IDE activity, and in a separate container the antibody disclosed herein.

According to specific embodiments, the composition or the article of manufacture further comprises a protease inhibitor.

According to a specific embodiment, the composition or the article of manufacture further comprises a secondary antibody capable of binding the antibody.

According to specific embodiments, the antibody disclosed herein is bound to a detectable moiety.

Examples of detectable moieties that can be used in the present invention include but are not limited to radioactive isotopes, phosphorescent chemicals, chemiluminescent chemicals, fluorescent chemicals, enzymes, fluorescent polypeptides, a radioactive isotope (such as $^{[125]}$iodine) and epitope tags. The detectable moiety can be a member of a binding pair, which is identifiable via its interaction with an additional member of the binding pair, and a label which is directly visualized. In one example, the label is a fluorescent protein or an enzyme producing a colorimetric reaction.

Examples of suitable fluorophores include, but are not limited to, phycoerythrin (PE), fluorescein isothiocyanate (FITC), Cy-chrome, rhodamine, green fluorescent protein (GFP), blue fluorescent protein (BFP), Texas red, PE-Cy5, and the like. For additional guidance regarding fluorophore selection, methods of linking fluorophores to various types of molecules see Richard P. Haugland, "Molecular Probes: Handbook of Fluorescent Probes and Research Chemicals 1992-1994", 5th ed., Molecular Probes, Inc. (1994); U.S. Pat. No. 6,037,137 to Oncoimmunin Inc.; Hermanson, "Bioconjugate Techniques", Academic Press New York, N.Y. (1995); Kay M. et al., 1995. Biochemistry 34:293; Stubbs et al., 1996. Biochemistry 35:937; Gakamsky D. et al., "Evaluating Receptor Stoichiometry by Fluorescence Resonance Energy Transfer," in "Receptors: A Practical Approach," 2nd ed., Stanford C. and Horton R. (eds.), Oxford University Press, UK. (2001); U.S. Pat. No. 6,350,466 to Targesome, Inc.].

Numerous types of enzymes may be attached to the antibody e.g., horseradish peroxidase (HPR), beta-galactosidase, and alkaline phosphatase (AP).

Exemplary identifiable moieties include, but are not limited to green fluorescent protein, alkaline phosphatase, peroxidase, histidine tag, biotin, orange fluorescent protein and streptavidin.

Further examples of detectable moieties, include those detectable by Positron Emission Tomagraphy (PET) and Magnetic Resonance Imaging (MRI), all of which are well known to those of skill in the art.

According to some embodiments, the detectable moiety is conjugated by translationally fusing the polynucleotide encoding the antibody disclosed herein with the nucleic acid sequence encoding the detectable moiety.

Additionally or alternatively, the detectable moiety can be chemically conjugated (coupled) to the antibody disclosed herein, using any conjugation method known to one skilled in the art.

According to specific embodiments, the methods disclosed herein comprise corroborating the diagnosis using a state of the art technique. Such methods are known in the art and depend on the type of the disease and include, as a non-limiting example, fasting sugar blood tests or A1c blood tests for diabetes.

According to specific embodiments the diagnostic method further comprises treating the diagnosed subject with an effective amount of a therapy for the disease.

Thus, according to an aspect of the present invention, there is provided a method of treating a disease associated with an IDE activity in a subject in need thereof, the method comprising:

(a) diagnosing the subject according to the method; and wherein when said level of said IDE is above said predetermined threshold, (b) treating said subject with a therapy for the disease, thereby treating the disease in the subject.

As IDE was shown by the present inventors as a prognosis marker for metabolic syndrome, the level of IDE may be used to selecting treatment regime (e.g. type, dose) suitable for the subject. That is, a disease with poor prognosis is treated with a treatment regime suitable for poor prognosis; while a disease with good prognosis is treated with a treatment regime suitable for good prognosis. According to specific embodiments, the level of IDE can indicate the likelihood that the subject will respond to the given therapy.

Hence, according to an additional or an alternative aspect of the present invention, there is provided a method of treating a disease associated with an IDE activity in a subject in need thereof, the method comprising:

(a) diagnosing the subject according to the method; and wherein when said level of said IDE is above said predetermined threshold, (b) selecting a therapy based on the level of said IDE, thereby treating the disease in the subject.

According to an additional or an alternative aspect of the present invention, there is provided a method of treating a disease associated with an IDE activity in a subject in need thereof, the method comprising:

(a) prognosing the subject according to the method; and (b) treating said subject with a therapy according to the prognosis.

According to an additional or an alternative aspect of the present invention, there is provided a method of treating a disease associated with an IDE activity in a subject in need thereof, the method comprising:

(a) prognosing the subject according to the method; and (b) selecting a therapy according to the prognosis.

According to specific embodiments, the therapy comprises antibody (ii) or (iii) disclosed herein.

According to an additional or an alternative aspect of the present invention there is provided a method of monitoring efficacy of a therapy for a disease associated with an IDE activity in a subject diagnosed with the disease, the method comprising determining a level of IDE in a biological sample of the subject undergoing or following the therapy using the antibody disclosed herein, wherein when said level of said IDE is decreased from a predetermined threshold following the therapy the therapy is efficacious.

Thus, a decrease in the level of IDE is indicative of the therapy being efficient.

On the other hand, if there is no change in the level of IDE, or in case there is an increase in the level of IDE, then the therapy is not efficient in treating the disease and additional and/or alternative therapies (e.g., treatment regimens) may be used.

According to specific embodiments of the monitoring aspects disclosed herein, the predetermined threshold is in comparison to the level in the subject prior to the therapy.

According to specific embodiments of the monitoring aspects disclosed herein, the predetermined threshold is at least 1.5 fold, at least 2 fold, at least 3 fold, at least 5 fold, at least 10 fold, or at least 20 fold as compared the level of IDE in a control sample or in the subject prior to the therapy as measured using the same assay such as ELISA, western blot or IP.

According to a specific embodiment, the predetermined threshold is at least 1.5 fold as compared the level of IDE in a control sample or in the subject prior to the therapy.

According to specific embodiments, the predetermined threshold is at least 2%, at least 5%, at least 10%, at least 20%, at least 30%, at least 40%, at least 50%, at least 60%, at least 70%, at least 80%, at least 90%, e.g., 100%, at least 200%, at least 300%, at least 400%, at least 500%, at least 600% as compared the level of IDE in a control sample or in the subject prior to the therapy.

According to other specific embodiments of this aspect of the present invention, the predetermined threshold can be determined in a subset of subjects with a known therapy outcome.

According to yet additional aspect of the present invention, there is provided an article of manufacture comprising the antibody disclosed herein and in a separate container a reagent suitable for ELISA, western blot or IP, an ELISA plate and/or a positive control sample comprising IDE. As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first, indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S.

Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839, 153; 3,850,752; 3,850,578; 3,853,987; 3,867,517; 3,879, 262; 3,901,654; 3,935,074; 3,984,533; 3,996,345; 4,034, 074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, CA (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Materials and Methods

Mice—C57BL/6 male mice (Jackson Laboratory) were kept in a specific pathogen-free facility at Tel Aviv University. All experiments were in accordance with Tel Aviv University guidelines and approved by the TAU animal care committee for animal research.

Generation and expression IDE vectors—Sequences for wild type (WT) and E111Q recombinant human IDE (rhIDE) optimized for bacterial expression were ordered from Genewiz (South Plainfield, New Jersey, USA) and received in pUC57 vector between NdeI and HindIII restriction sites. The vector encodes for rhIDE fused to the Ni-NTA binding tag His tag at its C-terminus. Rosetta BL21 *E. coli* cells were transformed with pET28a-rhIDE expression vector (WT and E111Q) and grown to $OD_{600nm}$=0.6-0.8 in 0.5 L LB medium supplemented with 25 μg/ml Kanamycin. Following, the culture was induced for protein expression with 0.5 mM IPTG overnight at 30° C. The cells were collected by centrifugation at 9000 rpm for 15 minutes. The pellet was suspended in 35 ml PBS with 0.1% Triton X-100 and lysed by 5 repetitive cycles of 30 seconds sonication and 2 minutes rest on ice. The soluble fraction was clarified by centrifugation at 12000 rpm for 30 minutes at 4° C. and then loaded onto a GE HisTrap 5 ml column. Columns were washed with 5 mM imidazole in PBS, and eluted with 0.5 M imidazole in PBS. The purified IDE protein was dialyzed against PBS, diluted to 2 mg/ml in PBS and 5% glycerol and stored at −80° C.

Bio panning—Phage display technique was utilized using the "Ronit 1" human synthetic antibody phage display library as previously described in Azriel-Rosenfeld et al. J Mol Biol (2004) 335(1):177-192. The library was subjected to four affinity-selection cycles on 10 μg/ml WT rhIDE that was used to coat wells of 24-well plates for 2 hours at room temperature wherein WT IDE was used as bait. During two of the cycles (cycle 1 and cycle 3), depletion was carried out using as bait the mutated E111Q IDE with an intention to isolate antibodies that bind in high affinity to the catalytic site of the WT enzyme. 10 μg/ml of mutated IDE was used to coat wells of 24-well plates for 2 hours at room temperature. The wells were washed once with 3 ml of PBS and blocked for 1 hour at 37° C. with sterile 3% skim milk in PBS. The wells were washed once with 3 ml of PBS and the phages were applied into the blocked, mutated IDE-coated well for 1 hour at 25° C. Following, the well coated with WT rhIDE and blocked similarly with 3% skim milk in PBS was washed once with 3 ml of PBS and the phages from the mutated IDE well (depleted phages) were transferred to the WT rhIDE well for another hour at 25° C. At the end of each affinity-selection cycle, the bound phages were eluted with 100 mM TEA pH=13 and immediately neutralized with 1 M Tris-HCl pH=7.4. Eluted phages were used to infect XL1-blue *E. coli* and grown to logarithmic phase for clonal amplification. Phage titer for input and output of selection allowed determining copies of each phage clone. 20-100 copies of each phage clone were later rescued by incubation of infected *E. coli* with $10^{10}$ CFU/ml M13KO7 helper phage overnight at 37° C. at 250 RPM. Virions from bacterial growth supernatant were precipitated in 20% PEG/NaCl and suspended in PBS prior being used in the next affinity-selection (panning) cycle. Following four cycles of affinity-selection, IDE-specific scFv-displaying phages were identified by monoclonal phage ELISA. In the phage ELISA, HRP-Anti-m13 monoclonal antibody conjugate: GE Healthcare, CAT 27-9421-01, was used to detect bound phages. Binders were verified for specificity by testing their binding to several control antigens, all purchased from SIGMA (now Merck) [BSA Merck CAT A7030-500G; lysozyme (Lysozyme from chicken egg white), Merck CAT L6876; Streptavidin (Streptavidin from *Streptomyces avidinii*) Merck CAT S0677]. The validated binders were reformatted for production as soluble antibodies and tested in three formats: MBP-scFv (FIG. 1E), Human IgG1 produced as "Inclonals" (FIG. 1F), and reverse-chimeric IgGs (FIG. 1G) produced in mammalian cells culture.

Sequencing—The nucleotide sequences of cloned genes were determined using the ABI 3500xl Genetic analyzer (Applied Biosystems, USA) according to the supplier's recommendations. DNA sequences of the cloned DNA fragments were analyzed using the program ApE—a plasmid Editor v2.0.47 (Wayne Davis, University of Utah). Analysis of antibody variable domain sequences and assignment to framework and CDR regions was done using the IgBlast tool of NCBI (www(dot)ncbi(dot)nlm(dot)nih(dot) gov/igblast)

Expression and purification of IDE-specific "Inclonal" IgG—expression and refolding of full length "Inclonal" IgG was effected using a protocol previously described in [Hakim, R. and Benhar, I. (2009) MAbs 1, 281-287; Buchner, J. et al. (1992) Anal. Biochem. 205, 263-270; and Benhar, I. and Pastan, I. (1994) Protein Eng. Des. Sel. 7, 1509-1515].

Dot-blot—Dot-blot was performed as previously described [Mazor, Y. et al/(2007) J. Immunol. Methods 321, 41-59]. Briefly, protein samples containing 0.1-1 μg purified protein in a total volume of 50 μl, in native form or following 5 minutes boiling at 95° C. (denaturing condition), were applied via a vacuum manifold onto a nitrocellulose membrane, using a Slot blot PR648 filtration manifold (Hoefer Scientific Instruments, San Francisco, CA, USA). Following, the membrane was blocked with 5% BSA in TBS for 1 hour at room temperature, and incubated overnight with 3 μg/ml MBP (Maltose-binding protein)-fused scFvs (prepared as described hereinbelow), diluted in the blocking solution at 4° C. After 3 washes with TBST, samples were incubated with mouse anti-MBP (1:5000 in TBST) for 1 hour at room temperature and following a wash were incubated with HRP-conjugated goat anti-mouse antibody (Jackson Immunoresearch Labs 115-035-003; 1:5,000 in TBST) for 1 hour at room temperature. Following 3 additional washes with TBST, the membrane was developed with an ECL reagent (WBLUR0500, Millipore, Milford, MA, USA) as recommended by the vendor, imaged using Amersham imager 600 (GE Healthcare Biosciences; Pittsburgh PA) and analyzed using the ImageJ v1.5i.

Production of IDE-specific MBP-scFvs—An expression vector was designed for the cytoplasmic expression in *E. coli* of MBP-scFv IDE-specific fusion proteins. Sequences for all scFv were taken from the corresponding pCC16 phagemid vector that were identified as specific IDE binders at the end of the phage display affinity selection process. The pMALc-NHNN vector [Birnboim-Perach, R. et al. (2019) Production of Stabilized Antibody Fragments in the *E. coli* Bacterial Cytoplasm and in Transiently Transfected Mammalian Cells. pp. 455-480, Humana Press, New York, NY]. Each scFv coding sequence was recovered by from the pCC16 phagemid following digestion by NcoI and NotI restriction enzymes and the sequences were ligated into the pMALc-NHNN vector between the NcoI and NotI restriction sites. The vector is encoding IDE-specific scFv fused to the Ni-NTA binding tag His tag and maltose binding protein (MBP) at its N-terminus.

For MBP-scFv production, Rosetta BL21 *E. coli* cells were transformed with pMALc-NHNN-MBP-IDE-specific scFv expression vectors and grown to OD600 nm=0.8 in 0.5 L LB medium supplemented with 100 µg/ml Ampicillin. Following, the culture was induced for protein expression with 0.5 mM IPTG overnight at 30° C. The cells were collected by centrifugation at 9000 rpm for 15 minutes. The pellet was suspended in 35 ml PBS with 0.1% Triton X-100 and lysed by 5 repetitive cycles of 30 seconds sonication and 2 minutes rest on ice. The soluble fraction was clarified by centrifugation at 12000 RPM for 30 minutes at 4° C. and then loaded onto a GE hisTrap 5 ml column. Columns were washed with 5 CV of 5 mM imidazole in PBS, 5 CV 20 mM imidazole in PBS and eluted from the columns with 250 mM imidazole in PBS. The purified MBP-scFv fusion protein was dialyzed against PBS, diluted to 2 mg/ml in PBS and stored at −80° C.

Splenocytes preparation—spleens harvested from C57BL/6 mice were homogenized on ice in RIPA lysis buffer ×1 supplemented with 0.1 mM DTT, 0.1 µM sodium vanadate, 0.5 mM PMSF and proteinase inhibitor cocktail (PIC) 1:100 and incubated for 20 minutes at 25° C. The supernatant was collected by centrifugation at 12000 RPM for 10 minutes at 4° C. and stored in 100 µl aliquots at −80° C.

Production of reverses chimeric anti mouse IDE antibodies—To convert the antibodies to full-size reverse-chimeric IgGs, polynucleotides encoding the generated antibodies were cloned into pcDNA 3.4 plasmid backbone. These plasmids are based on the CMV promoter-controlled pcDNA3.4 vectors that are provided as the "Antibody Expressing Positive Control Vector" part of the Expi293™ kit for transient transfection based expression. The kit also provides the Expi293F™ cells (ThermoFisher, #A14635). A detailed description of cloning antibody variable domains into IgG expression vectors was previously described [Birnboim-Perach, R et al. (2019) Production of Stabilized Antibody Fragments in the *E. coli* Bacterial Cytoplasm and in Transiently Transfected Mammalian Cells. pp. 455-480, Humana Press, New York, NY]. Briefly, the vector was expressed in *E. coli* Rosetta BL21 cells and purified using a HisTrap column (17-5248-01 GE Healthcare, Uppsala, Sweden). Antibodies were initially produced as fully human IgGs (with constant domains of human gamma1 heavy chain and of human kappa or lambda light chains) and subsequently, they were expressed with mouse constant domain of mouse gamma 1 heavy chain and mouse kappa light chain. Cloning was carried out by PCR amplification of the antibodies Heavy and Light variable domains followed by cloning into pcDNA 3.4 plasmids already carrying the corresponding constant domains by Gibson assembly [Gibson, D. G. et al. (2009) Nat. Methods 6, 343-345]. Transfection of Expi293F™ cells with the different pcDNA3.4 vectors was performed by ExpiFectamine™ transfection kit (Gibco, #A14524), according to manufacturer recommendations (Life Technologies, USA). For each transfection, a total amount of 30 µg plasmid DNA comprised of 3:1 molar ratio of the IgL and IgH respectively. Transfection, cell growth and collection of conditioned medium were carried out as recommended by the vendor (Life Technologies Expi293™ kit for transient transfection based expression). The antibodies-containing conditioned medium was harvested by centrifugation (Sorvall GSA rotor) for 10 minutes, at 4° C. at 8000 rpm, 6 to 7 days following transfection. Reverse chimeric mouse IgG1 mAbs were purified on Protein G columns, according to the manufacturer recommendations (GE Healthcare, Chicago, IL, USA). Prior to purification, antibody-containing media were buffered with 20 mM phosphate buffer, pH 7, and filtered. mAbs were eluted in 1 ml fractions and the pH was neutralized by 0.25 ml of 1.5 M Tris-HCl pH 8.8. Buffer-exchange to sterile DPBS (Sigma) was performed on 10-kDa Amicon® Ultra Centrifugal Filters (MilliporeSigma, Burlington, MA, USA; FIG. 1G) or PD-10 desalting columns (GE Healthcare, Chicago, IL, USA).

The antibodies were collected by centrifugation and concentrated to a final concentration of 1-2 mg/ml using a centrifugal filter concentrator. Purified antibodies were stored at −80° C. in small aliquots. Protein concentration was determined by measuring the absorbance of the protein at O.D. 280 nm in the Thermo Scientific NanoDrop™ 2000c spectrophotometer and dividing the absorbance value by the extinction coefficient factor of the protein (extinction coefficient was calculated by www(dot)expasy(dot)org/tools/protparam(dot)html).

IDE-binding assay—96-wells ELISA plates (Nunc, Roskilde, Denmark) were coated overnight at 4° C. with 2.5-5 µg/ml in PBS of WT rhIDE, mutant IDE, and non-relevant proteins: bovine serum albumin (BSA), His trap-purified protein (His) and/or MBP-LacZ (made in-house recombinantly). Following 3 washes with PBST, wells were blocked for 1 hour at room temperature with 3% w/v skim milk (232100, Difco, Sparks, MD, USA) in PBS. Following, wells were incubated for 2 hours at room temperature with the IDE specific generated antibodies in different formats: as phage clones—with serial dilutions, as MBP-scFv (data not shown), and as hIgG or as rcIgG in different concentrations. Bound phages were detected with mouse anti-M13 antibody (1 hour at room temperature) followed by incubation with HRP-conjugated goat anti-mouse secondary antibody (115-035-003, Jackson ImmunoResearch Laboratories, ME; 1:5, 000 in PBS) for 1 hour at room temperature. Human IDE-specific IgG antibodies were incubated with HRP-conjugated Goat anti Human (109-035-088, Jackson ImmunoResearch Laboratories, ME; 1:5,000 in PBS) or anti Mouse (115-035-062, Jackson ImmunoResearch Laboratories, ME; 1:5,000 in PBS) for 2 hours in room temperature. Following 3 washes with PBST, 3,3',5,5'-tetramethylbenzidine (TMB; eBioscience, San Diego, CA, USA) was added until color appeared. The reaction was stopped by adding 1 M $H_2SO_4$, and analyzed using a Spectrafluor plus microplate reader at 450 nm.

IDE Insulin digestion assay—Various concentrations of IDE inhibitors were incubated with 1.5 µg/ml rhIDE for 1 hour at room temperature. Following, recombinant human insulin (41-975-100, Biological Industries, Kibbutz Beit Haemek, Israel) diluted in Mercodia ultrasensitive Mouse Insulin ELISA (10-1249-01) calibrator 0 were added to the tubes and incubated for 2 hours at 37° C. 25 µl from each tube were taken and evaluated for residual insulin concentration using the Mercodia ultrasensitive Mouse Insulin ELISA kit. Absorbance at 450 nm was recorded by Spectrafluor plus microplate reader (Tecan, Mannedorf, Switzerland).

Streptozotocin (STZ) diabetes mouse model—10 weeks old C57BL/6 mice were fasted overnight, after which they were intraperitoneally injected with 150 mg/kg STZ diluted in 100 nM citrate buffer at pH 4.5. All mice developed hyperglycemia within two days from STZ injection. At day three following STZ injection, each mouse was intraperitoneal injected with 10 mg/kg of the generated reverse chimeric mAbs (rcH3 or the rc2E12 isotype control).

Oral glucose tolerance test (oGTT)—Mice were fasted for 2 hours after which they received a single intraperitoneal injection of the generated reverse chimeric mAbs (10 mg/kg), followed by additional 4 hours of fasting (6 in total). At the end of this time period, mice were given glucose orally, using a gavage needle, at a dose of 2 g/kg. Blood glucose was measured prior to glucose administration (time 0) and 15, 30, 60, 90 and 120 minutes following glucose administration using the Contour blood glucose meter (Bayer, Elkhart, IN, USA).

Insulin tolerance test (ITT)—Mice were fasted for 2 hours after which they received a single intraperitoneal injection of the generated reverse chimeric mAbs (10 mg/kg), followed by additional 4 hours of fasting (6 hours in total). At the end of this time period, the mice were given an intraperitoneal injection of insulin (0.5 U/Kg, dissolved in PBS). Blood glucose was measured prior to glucose administration (time 0) and 15, 30, 60, and 90 minutes following glucose administration. Blood glucose levels were measured using the Contour blood glucose meter (Bayer, Elkhart, IN, USA).

Serum collection—Following the ITT and the injection of reverse chimeric mAbs, mice were bled every 3 days from the facial vein using, a 27 G needle. Blood samples (no more than 120 µl each time) were put in 1.5 ml Eppendorf tube at room temperature for 1 hour. The clots were removed from the tubes using a needle, and the tubes were put on ice for 40 minutes. Following, the tubes were centrifuged for 10 minutes at 4° C. at 2300 RPM; the clear supernatant was then taken to a new tube for a second cleaning cycle. The supernatant was taken into a new tube, and kept at −20° C.

Detection of anti-IDE reverse-chimeric antibodies in serum samples—96-wells ELISA plates were coated over night with 5 µg/ml IDE in PBS, at 4° C. Following 3 washes in PBST, wells were blocked with 5% (w/v) skim milk in PBS, for 1 hour in room temperature. For the detection of the reverse-chimeric IDE-specific antibody (rcH3-IgG), serum samples were diluted 1:2700 in PBS, whereas control rc2E12 antibody-injected samples served as a positive control. Known concentrations of the rcH3-IgG antibody diluted in a 1:2700-diluted sample of control mice served as a reference for the measurement of IDE concentrations. Samples were incubated for 2 hours at room temperature. Following 3 washes, wells were incubated with 50 µl of HRP-conjugated goat anti mouse antibody (1:5,000 in PBS) for 1 hour at room temperature. Following 3 washes with PBST, TMB was added until color appeared. The reaction was stopped by adding 1 M $H_2SO_4$, and analyzed using a Spectrafluor plus microplate reader at 450 nm.

Production of reverse-chimeric anti-IDE H3 $Fab_2$ segments—10 milligrams of IgG were digested with 200 micrograms of IDES (Fabricator) enzyme (www(dot)genovis(dot)com/products/igg-proteases/fabricator/) at 37° C. for 20 hours. The $Fab_2$ fragment was separated from undigested IgG and the Fc fragments on a MAbSelect™ affinity column. The Fab2 was stored at −80° C. until use.

Determination of ROS levels in microglia—In order to measure intracellular ROS levels, N9 microglia were seeded on a clear-base black-framed 24 wells plate (#4TI-0241, BIOKÉ, Leiden, the Netherlands), at a concentration of $0.5×10^5$ cells/ml in RPMI medium containing 10% FCS. After 24 hours, the medium was replaced and the cells were incubated for 24 hours with RPMI medium without serum, with or without 0.1 µg/ml LPS. For the detection of ROS in DJ-1-KD cells, DJ-1-KD microglia were grown as previously described (Nash et al. 2017). Control and DJ-1-KD microglia were seeded at a concentration of $0.8×10^5$ cells/ml in RPMI medium containing 10% FCS. The following day, the medium was replaced with an RPMI medium without serum containing 1 µM Rotenone (#R8875; Sigma) for 2 hours. The medium was then removed and the wells were washed once in RPMI medium without serum, cells were incubated with Fab fragments of anti-IDE antibodies (100 nM) for 2 hours. Next, insulin was added to the wells over-night to a final concentration of 100 nM. At the end of the experiment, the medium was replaced to RPMI medium containing 10 µM $H_2DCFDA$ (#D6883; Sigma) for 30 minutes at 37° C. in the dark, as previously described (Trudler et al. 2014). Following the oxidation of $H_2DCFDA$ to DCF the fluorescence of the cells was measured by the Synergy HT spectrofluorometer (BioTek, Winooski, VT, USA) using excitation wavelength of 485 nm and emission wavelength of 528 nm. Normalization of ROS levels to cell numbers was achieved by subsequent MB staining of the cells (as described above), and division of the ROS levels by the MB signal in each well.

Subjects—A total of 24 healthy volunteers and 51 metabolic syndrome (MS) patients from a previously described cohort (Marcus Y, et al. J Clin Hypertens (Greenwich). 2016; 18(1): 19-24) were recruited (Table 1 hereinbelow). To qualify for inclusion as an MS patient, subjects aged 18 to 75 years had to fulfill the criteria from the Third Report of the Adult Treatment Panel (ATP III) (Circulation. 2002; 106(25): 3143-421). Impaired fasting glucose was considered a glucose level ≥100 mg %. None of the subjects were treated with anti-diabetic drugs. The study was approved by the Tel Aviv-Sourasky Medical center institutional Helsinki's committee. Consent has been obtained from each patient after full explanation of the purpose and nature of all procedures used.

Biochemical Analysis of Human serum samples—Serum chemistry was measured by routine commercial automated assays (Centaur, Roche, Indianapolis, IN). HbA1c levels were measured using HPLC (Tosoh Bioscience, San Francisco, CA).

Generation of polyclonal anti IDE antibodies—Animal immunization: Eight weeks old female NZW rabbits that weighed 2.5 kg were purchased from Harlan (Israel). Polyclonal antisera was produced in each animal by subcutaneous immunization with 100 μg of rhIDE emulsified at 1:1 ratio in an emulsion of 400 μg of *M. tuberculosis* extract H37 in incomplete Freund's adjuvant (CFA). Each animal was given weekly boosts of rhIDE emulsified in the same manner in incomplete Freund's adjuvant without *M. tuberculosis* extract (IFA) every week. Rabbit arterial blood was collected prior to the first vaccination and each one week after each boost, and as a final (terminal) bleed. A total of three boost immunizations were required to reach a plateau of serum antibody titer (>20000). Analysis of anti-IDE serum polyclonal antibody titer: Blood collected from each animal was incubated at room temperature for 1 hour and at 4° C. for an additional 1 hour in order to coagulate. Serum supernatant was separated from the clotted blood by centrifugation at 3000 g for 20 minutes at 4° C. Anti-IDE antibody titer was measured by direct ELISA as follows: A 96-well ELISA plate (Nunc, Roskilde, Denmark) was coated overnight at 4° C. with 50 μl/well of rhIDE diluted in PBS to a final concentration of 2.5 μg/ml. On the following day, the plate was washed once with 300 μl/well of 0.05% Tween 20 in PBS (PBST) and was blocked with 300 μl/well of 3% skim-milk (w/v; Difco™ Skim Milk, BD) in PBS for 1 hour at 37° C. Next, the plate was washed three times with 300 μl/well PBST and serial ×3 serum samples diluted in PBST were applied and left to bind for 1 hour at room temperature. Following, the plate was washed three times with 300 μl/well PBST. Bound anti-IDE polyclonal antibodies were detected by applying HRP-conjugated goat-anti-rabbit IgG (#111-035-004, Jackson Immunoresearch Laboratories) diluted ×2000 in PBS and the plate was incubated for 1 hour at room temperature, followed by washing three times with 300 μl/well PBST. Finally, 50 μl/well of the HRP substrate 3,3',5,5'-tetramethylbenzidine (TMB; eBioscience, San Diego, CA, USA) were added until color appeared. The reaction was stopped by adding 50 μl/well 1 M $H_2SO_4$, and analyzed using a Spectrafluor plus microplate reader (Tecan, Männedorf, Switzerland). The optical density was measured at 450 and 570 nanometer wavelengths, and analyzed using the Magellan software version 2.22 (Tecan). Upon the development of sufficient titer levels, animals were terminally bled and serum was separated by letting the blood clot for 1 hour at 4° C. and separating the serum from the blood clot by centrifugation an 14000 g in an Eppendorf microfuge at 4° C. The serum was divided into 100 μl aliquots and stored at −80° C.

Figures 7A, 7B, 7C:
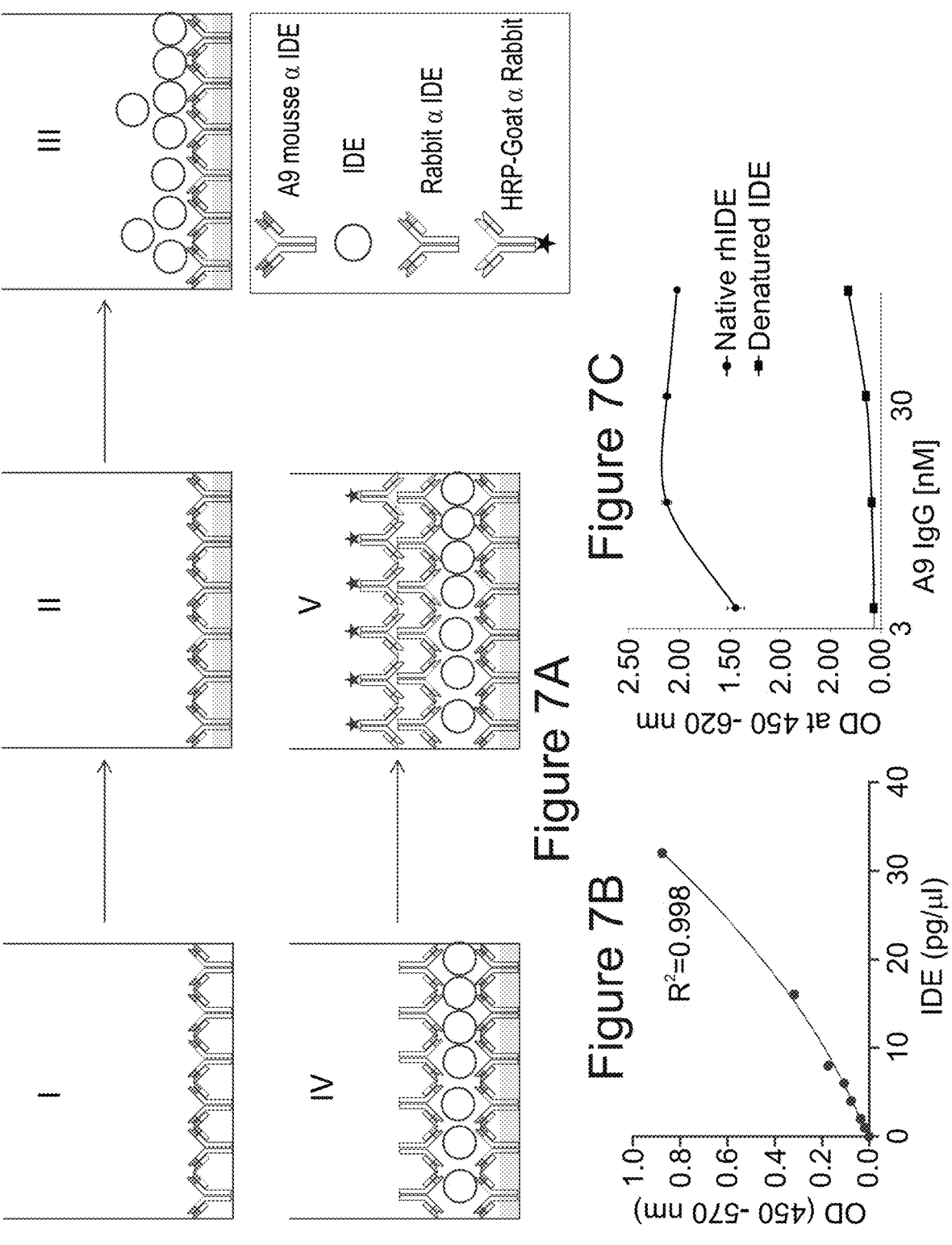
FIGS. 7A-C demonstrate an ELISA assay for detection of IDE in human serum.

Determination of IDE serum concentration by ELISA—For measuring IDE in bodily fluids, a highly sensitive sandwich ELISA suitable for quantifying IDE in human and in mouse sera, was developed. 96-wells ELISA plates (Nuns, Roskilde, Denmark) were coated overnight at 4° C. with 50 μl/well of anti-IDE antibody A9 diluted in PBS to a final concentration of 0.5 μg/ml. On the following day, the plate was washed once with 300 μl/well PBST and was blocked with 300 μl/well of 3% skim-milk (w/v; Difco™ Skim Milk, BD) in PBS for 1 hour at 37° C. Next, the plate was washed three times with 300 μl/well PBST; and 50 μl/well of serum samples diluted ×3 or ×9 in PBS were applied and left to bind overnight (ON) at 37° C. A concentration curve was prepared by spiking a control serum (un-detectable IDE concentration) with serial ×2 dilutions of rhIDE starting at 500 ng/ml in PBS (FIG. 7A). The plate was left for 2 hours at room temperature (about 25° C.), and then washed three times with 300 μl/well PBST. Bound IDE was detected by applying 300 μl/well of rabbit polyclonal anti-IDE serum diluted ×2000 in PBS and incubation for 1 hour at room temperature, followed by washing three times with 300 μl/well PBST. Next, 50 μl/well of HRP-conjugated goat-anti-rabbit IgG (#111-035-004, Jackson Immunoresearch Laboratories) diluted ×2000 in PBS were applied and incubated for 1 hour at room temperature followed by washing three times with 300 μl/well PBST. Finally, 50 μl/well of the HRP substrate TMB were added until color appeared. The reaction was stopped by adding 50 μl well 1 M $H_2SO_4$, and analyzed using a Spectrafluor plus microplate reader (Tecan, Männedorf, Switzerland). The optical density was measured at 450 and 570 nanometer wavelengths, and analyzed using the Magellan software version 2.22 (Tecan).

Statistical analysis—GraphPad software (GraphPad Prism v8) was utilized for all statistical analyses described in Examples 1-3 hereinbelow. Data comparisons were carried out using either an unpaired two-tailed Student's t test when two groups were compared or one-way ANOVA (with Bonferroni's post-hoc test) when three or more groups were analyzed. Each experiment was repeated at least three times. P<0.05 was considered significant. For Example 4 hereinbelow, the collected data were analyzed with IBM SPSS, version 25.0. The normal distribution of the data was verified by comparing the mean to the median, comparing the mean to the 5% trimmed mean, the values of skewness and kurtosis and the result of the Shapiro-Wilk's test. The results showed that some of the variables in MS group didn't follow a normal distribution. Differences between the two groups (MS patients and controls) were analyzed by both independent samples t-test and Mann-Whitney tests for continuous variables, and by Chi-square test for categorical variables. Since the results from the t-test and Mann-Whitney tests were the same, the t-tests results are the ones reported. Descriptive statistics are given as means and standard deviations or frequency with percentage according to the scale of the variable. Since the difference in age was significant, this factor was controlled for and differences were tested by General linear models (GLMs). A p-value <0.05 was considered statistically significant. All reported P-values are two-tailed.

Example 1

Generation of Anti-IDE Antibodies and Evaluation of their Inhibitory Effect on Ide Activity In-Vitro
Generation of Anti-IDE Antibodies Recombinant human IDE (rhIDE) to be used as the antigen for both screening and immunization were purified. To this end, both the wild type (WT) form of the protein and the E111Q mutated form of the enzyme, in which a point-mutation at the catalytic site markedly reduces the enzyme's catalytic activity (35), were expressed. The genes encoding the two forms of IDE were cloned into a pET28a+ plasmid backbone, with a His tag at their C-terminus. The vector expressing recombinant human IDE (rhIDE) with His tag at its C-terminus is presented in FIG. 1A.

Following induction of expression of the vector, a marked increase in the expression of a 110 kDa protein was visible by SDS-PAGE (FIG. 1B), and protein's identity was verified by an immunoblot assay using IDE-specific antibodies (FIG. 1C). In the next step, an insulin degradation assay with the purified proteins was performed which showed observed that the WT IDE protein effectively degraded insulin (~60% degradation following 2 hours at 37° C.), whereas the mutated IDE degraded only 15% of the insulin under the same conditions (FIG. 1D).

The purified IDE was used to isolate specific scFv clones that recognize epitopes of the recombinant human IDE. Phage display technique was utilized using a human synthetic antibody phage display library. Specifically, a human scFv library, the Ronit 1 library [described in Azriel-Rosenfeld et al. J Mol Biol. (2004) 335(1):177-192], was screened. The library was subjected to four affinity-selection cycles on recombinant human wild type (wt) IDE (rhIDE). During two of the cycles, depletion was carried out against E111Q IDE with an intention to isolate antibodies that bind in high affinity to the catalytic site of the WT enzyme. Following four cycles of affinity-selection, three IDE-specific scFv-displaying phages were identified by monoclonal phage ELISA, referred to herein as A9, B1 and H3. As shown in FIGS. 2A-F, serial dilutions of phages displaying the A9, B1 and H3 (FIG. 2A-C, respectively) bind IDE well, and show little to no binding to BSA, MBP, or other purified recombinant proteins that were used as negative controls.

The nucleic acid and amino acid sequences of the heavy and light chains, as well as the CDRs, of the three anti-human IDE antibodies were determined. These are set forth in SEQ ID NOs: 1-2 and 9-10 (for A9 heavy and light chains, respectively), SEQ ID NOs: 3-8 (for A9 heavy chain CDRs), SEQ ID NOs: 11-16 (for A9 light chain CDRs), SEQ ID NOs: 17-18 and 25-26 (for B1 heavy and light chains, respectively), SEQ ID NOs: 19-24 (for B1 heavy chain CDRs), SEQ ID NOs: 27-32 (for B1 light chain CDRs), SEQ ID NOs: 33-34 and 41-42 (for H3 heavy and light chains, respectively), SEQ ID NOs: 35-40 (for H3 heavy chain CDRs) and SEQ ID NOs: 43-48 (for H3 light chain CDRs).

For initial evaluation of full-size IgGs, the antibodies were produced as "Inclonals", i.e. IgGs expressed in an *E. coli* expression system (29) (FIG. 1F). The isolated Inclonal antibodies showed a marked binding to IDE, and an $EC_{50}$ of about 1 nM (FIGS. 2D-F). The Inclonal antibodies showed very little binding to BSA, evident only at saturating concentrations. Together, these results suggest that the three "Inclonal" antibodies bind IDE with high affinity and specificity.

The Generated Anti-IDE Antibodies Inhibit Insulin Degradation In Vitro

Figure 3A:
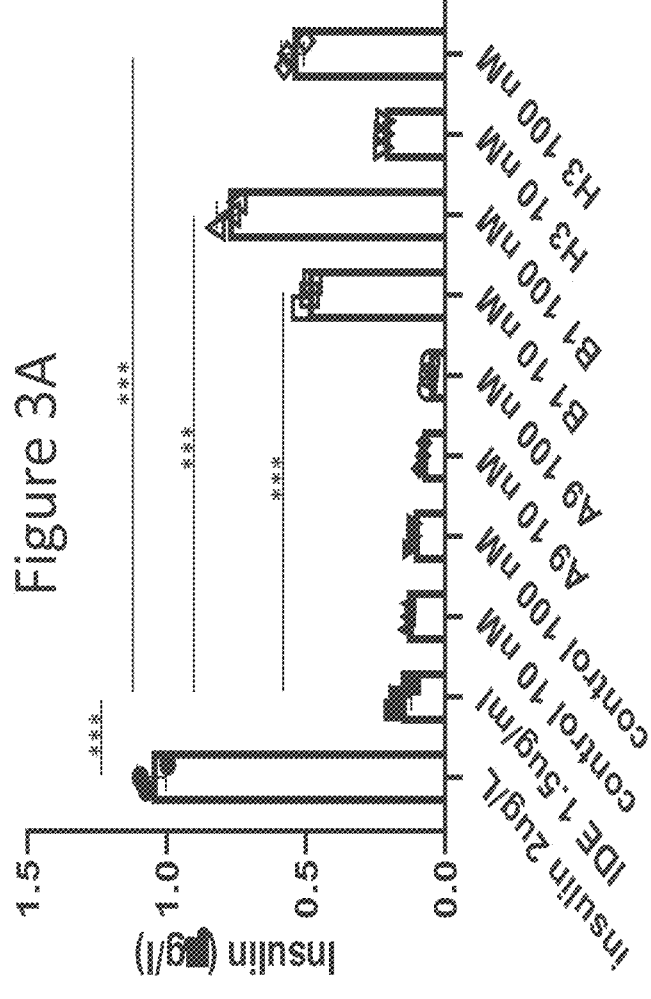
FIGS. 3A-B demonstrate IDE inhibition assay using anti-IDE MBP-scFvs or inclonal IgGs. The Figures show inhibition of IDE activity as determined by residual insulin levels following incubation with the generated antibodies. 1.5 µg/ml IDE was incubated with the indicated concentrations of anti-IDE scFv clones A9, B1 or H3 or a control scFv (FIG. 3A); or with anti-IDE Inclonal IgGs clone A9 or H3 or a non-relevant Inclonal IgG (depicted as "AF") (FIG. 3B) and with an IDE inhibitor peptide ADT21 for 1 hour at room temperature, followed by incubation with 2 µg/L human insulin for 2 hours at 37° C. Residual insulin was later analyzed using Mercodia ultrasensitive mouse insulin ELISA. Detection was effected by an ELISA plate reader at 450 nm. The results are presented as mean±SEM (n=3). ***—P<0.001, One way ANOVA with Bonferroni correction.
Figure 3B:
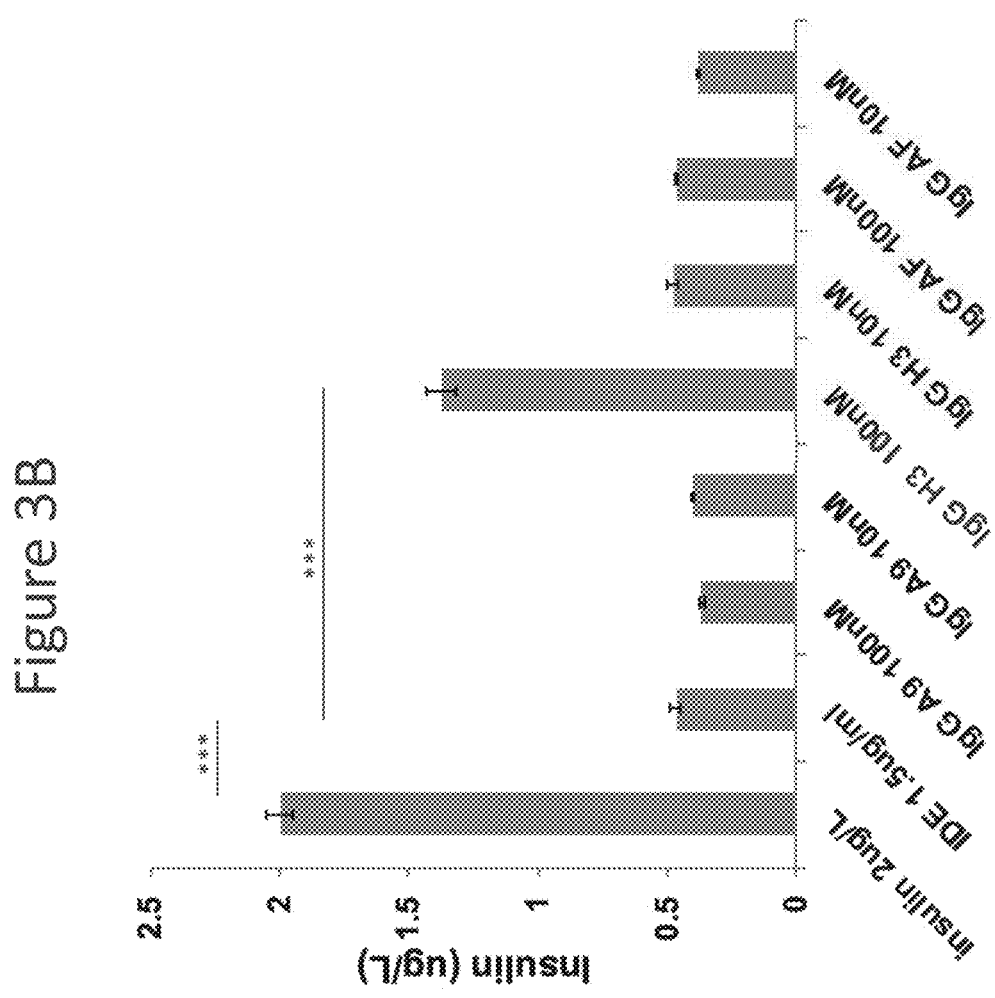

To test the ability of the generated anti-IDE scFvs and IgGs to inhibit IDE-mediated insulin degradation, rhIDE was incubated for 1 hour at room temperature with each antibody in the form of MBP-scFv or with a control MBP-scFv that does not bind rhIDE. Following, insulin was added for 2 hours at 37° C. Activity was measured as residual insulin using Mercodia ultrasensitive mouse insulin ELISA kit. A dose dependent inhibition of IDE activity was observed in the presence of B1 and H3 scFvs: B1 inhibited insulin degradation by 64% (P<0.001) and 35% (P<0.001) using 100 nM and 10 nM scFv, respectively; H3 inhibited insulin degradation by 40% (P<0.001) using 100 nM and no significant inhibition was observed using 10 nM (FIG. 3A). There was no apparent IDE activity inhibition using A9 and the control MBP-scFvs. After re-formatting the antibodies to full-size human IgGs, their ability to inhibit IDE activity was re-evaluated. In the IgG format the H3 antibody showed marked efficacy in inhibiting IDE activity while A9 and the negative control antibodies failed to do so (p<0.001, FIG. 3B).

The Generated Anti-IDE Antibodies Recognize Conformational IDE Epitopes

To assess the binding epitope on IDE to which the generated antibodies bind, dot-blot analysis was effected. Specifically, rhIDE in serial dilutions and a mouse spleen lysate as control, were spotted onto a nitrocellulose membrane in both native state and denaturing conditions. The native rhIDE protein samples were detected by all the antibody clones, with B1 MBP-scFv giving the highest signal. All the denatured protein samples yielded weaker signals than the native samples, or failed to give any visible dot (FIG. 4A). These results suggest that the selected scFv clones recognize conformational epitopes of the rhIDE that are destroyed under denaturing conditions, rather than linear epitopes.

Example 2

The Therapeutic Effect of the Generated Anti-Ide Antibodies in a Diabetes Animal Model
Conversion of the Anti-IDE H3 Antibody to Reverse-Chimeric IgG Chimeric antibodies were a critical milestone in the history of therapeutic antibody development. Chimeric antibodies are recombinant IgGs where the variable domains are from a mouse antibody while the constant domains are human sequences. Compared to mouse monoclonal antibodies (mAbs), chimeric antibodies are far less immunogenic, limiting the elicitation of human-anti-mouse antibodies upon administration to human patients (36). Conversely, Reverse-chimeric are antibodies with human variable domains and murine constant domains (37). In addition to being useful for antibody discovery in transgenic mice, reverse-chimeric antibodies can be very useful for treating mouse models, to avoid eliciting a mouse-anti-human immune response. In order to evaluate the efficacy of the generated anti-IDE antibodies in mouse models, the human H3 IgG antibody was converted to reverse-chimeric IgGs (rcIgGs) (mouse IgG1 isotype) and its ability to bind IDE, BSA, and the E111Q IDE mutant was evaluated. Antibody rc2E12 that does not bind IDE served as an isotype control. As shown in FIG. 4B, rcH3-IgG binds IDE with high affinity ($EC_{50}$ of 1.62 nM). Furthermore, the rcH3-IgG showed specificity to the active IDE and did not bind to the mutant IDE or BSA. Further, the ability of rcH3-IgG antibody to inhibit IDE activity was tested. rcH3-IgG antibody inhibited IDE in a dose dependent manner (FIG. 4C). Taken together, these results suggest that a reverse-chimeric H3 IgG retains similar properties to the human H3 IgG version.
rcH3-IgG Antibody Improves Insulin Signaling in a Diabetes Mouse Model It was previously suggested that inhibition of IDE may improve insulin activity in a diabetes mouse model (38). Thus, the ability of rcH3-IgG to reduce glucose levels (oGTT) and improve insulin activity (iTT) in STZ treated mice was assessed. To this end, rcH3-IgG or an isotype control antibody was administered intraperitoneally to STZ-treated mice, 1 hour prior to testing oGTT and iTT. Following a glucose challenge (oGTT), both control and rcH3-IgG-treated mice exhibited a rise in blood glucose levels. However, rcH3-IgG-treated mice exhibited lower levels of glucose through time, compared to the control-treated mice (p<0.05). Post-hoc analysis revealed that rcH3-IgG-treated mice had significantly lower glucose levels 90 minutes following glucose administration, compared to the isotype control-treated mice (p<0.05; FIG. 5A). Further, the ability of rcH3-IgG to improve insulin activity (ITT) was evaluated. While the rcH3-IgG-treated mice exhibited a significant reduction in glucose levels starting from 30 minutes following insulin administration (p<0.001), the isotype control-treated mice exhibited a significant reduction in glucose levels only after 90 minutes (p<0.05). Finally, the half-life of the rcH3-IgG antibody in the sera of administrated mice was determined, and was found to be about 11 days. Taken together, these results suggest that treatment with rcH3-IgG improves glucose levels and insulin activity in a diabetes mouse model.

Example 3

The Effect of the Generated Anti-IDE Antibodies on Microglia Having a Parkinson's Disease Phenotype In order to evaluate the therapeutic effect of the generated antibodies on Parkinson's disease, DJ-1 knockdown (KD) microglia which present the neurotoxic phenotype of microglia as appears in Parkinson's disease (Nash et al. J Neurochem. 2017 143(5):584-594; and Trudler et al. J Neurochem. 2014 129(3):434-47) were used. Previous studies have shown that DJ-1 KD microglia generate higher levels of reactive oxygen species (ROS) under basal and inflammatory stimulation conditions (Trudler et al. 2014). In order to avoid possible binding of the generated anti-IDE antibodies to microglia by Fc receptors expressed on the microglia membrane (Teeling et al. 2012), the $Fab_2$ segments of the rcH3-IgG antibody (referred to herein as "H3 Fab") were tested in these setting.

Figure 6B:
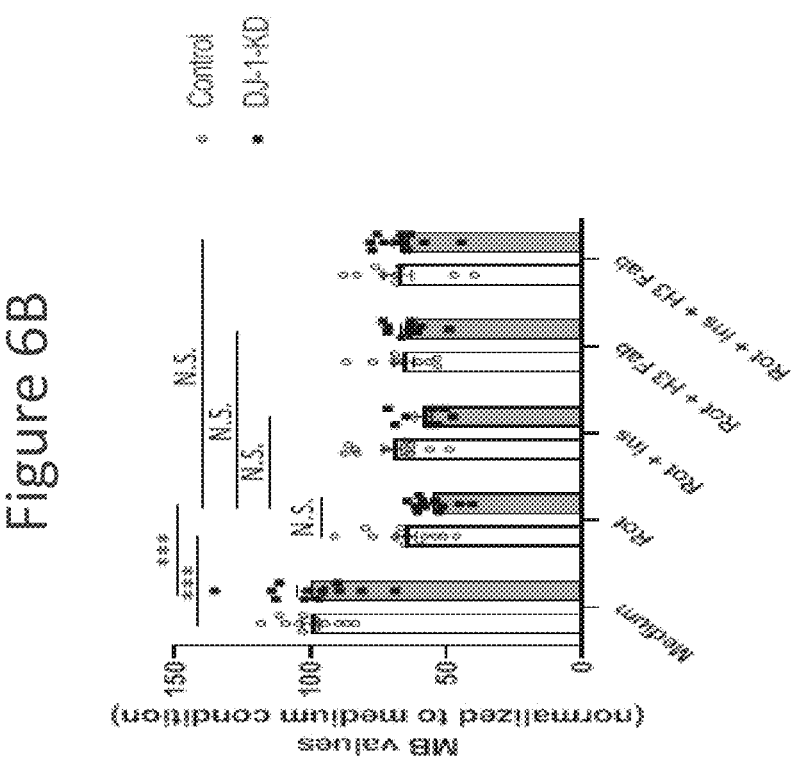
FIGS. 6A-B demonstrate the in-vitro effect of Fab$_2$ segments of the reverse-chimeric anti-IDE H3 antibody (referred to herein as "H3 Fab") on reduction of reactive oxidative species (ROS) in DJ-1 knock down (KD) microglia, which present the neurotoxic phenotype of microglia in Parkinson's disease. In addition, the cells were treated with Rotenone where indicated (marked as "Rot"), to increase production of ROS. Shown are ROS levels per methylene blue (MB) (FIG. 6A) and MB values following incubation with the H3 Fab antibody as compared to medium control. DJ-1-KD microglia exhibit higher levels of ROS compared to control microglia, and Rotenone-induced increase can be mitigated using anti-IDE H3 Fab. Furthermore, the result using MB test shows that insulin or H3 Fab treatments do not significantly affect cell survival after Rotenone challenge. (N=3, 2-4 repeats in each experiments; total n=6-12). Rot=Rotenone; ins=insulin. Results are represented as mean±SEM. *** p<0.001, N.S. not significant.
Figure 6A:
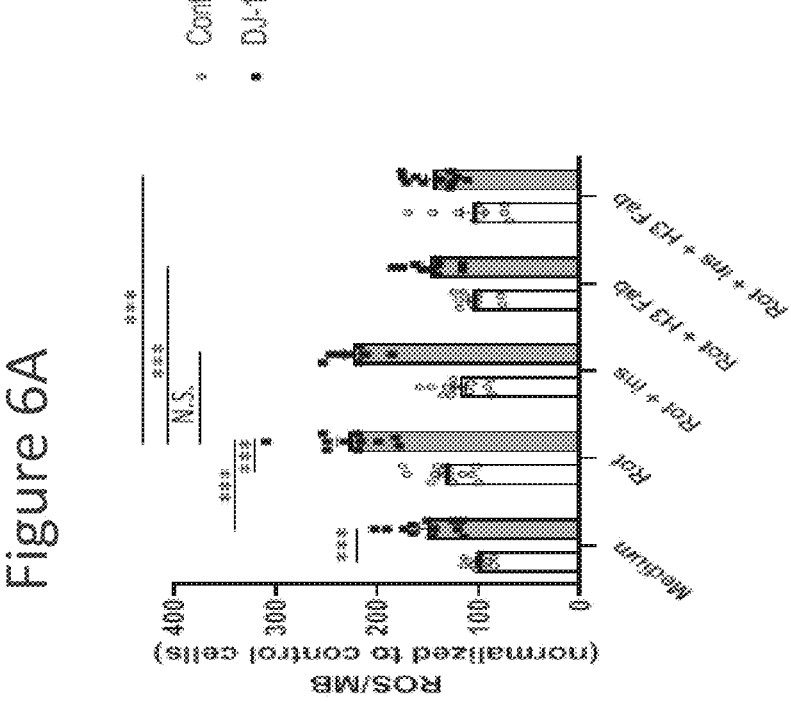

As shown in FIG. 6A, DJ-1 KD microglia exhibit a 51% increase in ROS levels compared to control microglia, in agreement with previous reported findings (Trudler et al. 2014). Furthermore, a short stimulation of the cells with Rotenone, a known inhibitor of the mitochondrial complex I which serves as an experimental model for Parkinson's disease (Xiong et al. 2012), significantly increased the production of ROS in DJ-1-KD microglia (227% compared to control cells at baseline, p<0.001). While 100 nM insulin stimulation following the Rotenone insult did not reduce ROS production, incubation of the cells with 100 nM H3 Fab significantly reduced ROS production in DJ-1 KD cells (p<0.001) to levels comparable to the basal levels of the cells (151% of control cells at baseline, vs. 148% for H3 Fab-treated cells following Rotenone challenge). Notably, as shown in FIG. 6B, using a MB assay to measure the effect of the treatment on total cell number indicated that insulin or H3 treatments do not significantly affect cell survival after Rotenone challenge. This is an important control to assess the protective and non-toxic effect.

Taken together, these results suggest that an rcH3 antibody may serve as a therapeutic approach in Parkinson's disease.

Example 4

Figures 8A, 8B:
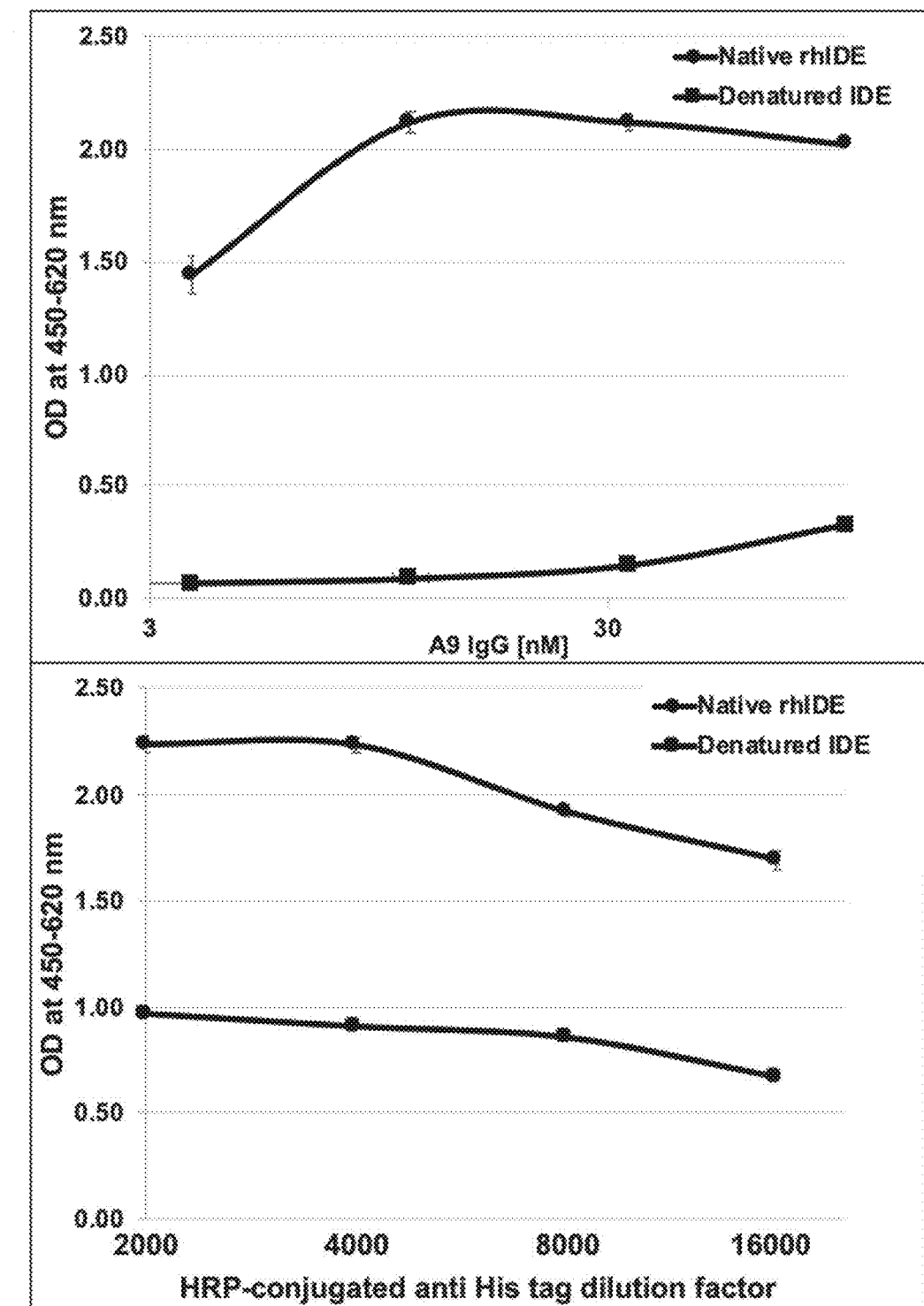
FIGS. 8A-B shows that IgG A9 recognizes a conformational epitope on rhIDE. A solution of 5 µg/ml rhIDE in PBS was prepared and either used directly to coat half of an ELISA plate or denatured by heating at 80° C. for 20 min followed by chilling on ice before using it to coat the other half of the ELISA plate. The plate was coated overnight at 4° C. with 50 µl/well. On the following day, the plate was washed once with 300 µl/well of PBST and was blocked with 300 µl/well of 3% skim-milk solution in PBS for 1 h at 37° C. Next, the plate was washed three times with 300 of PBST and (FIG. 8A) IgG A9 at concentrations of 100, 33.3, 11.1, 3.7 nM was applied to the wells of three columns of wells coated with native or with heat-denatured rhIDE. This was followed by washing these wells three times with 300 µl/well of PBST/well followed by adding 50 µl/well of HRP-conjugated goat anti human IgG diluted ×5000 in PBST.

Diagnosing and Prognosing Metabolic Syndrome Using the Generated Anti-IDE Antibodies Using the generated anti-IDE antibodies, a sandwich ELISA for the detection and quantification of IDE was developed (FIG. 7A). As shown in FIG. 7B, this ELISA assay readily detects rhIDE with high sensitivity, from 5 pg/µl up to concentrations of 500 pg/µl. Human and mouse IDE share >95% sequence identity, hence it was reasoned and verified that the polyclonal and monoclonal antibodies generated will also bind mouse IDE. In order to define whether antibody A9 recognized the conformation of active rhIDE, the difference in binding to the denaturation form of rhIDE was evaluaed. As shown in FIG. 7C, thermal denaturation of rhIDE resulted in a very significant reduction in the ELISA signal resulting from detection with A9 IgG (down to almost negligible signal). Of note, thermal denaturation of rhIDE also resulted in about ×2-3 lowering of the ELISA signal shown in FIGS. 8A-B, where rhIDE was detected using serial ×2 dilutions of an anti His-tag antibody (that recognizes a linear epitope), suggesting that denatured rhIDE might also bind less efficiently to the wells of the ELISA plate. Combined, these results suggest that that A9 IgG recognizes specifically a conformational epitope of the active rhIDE.

Figure 9:
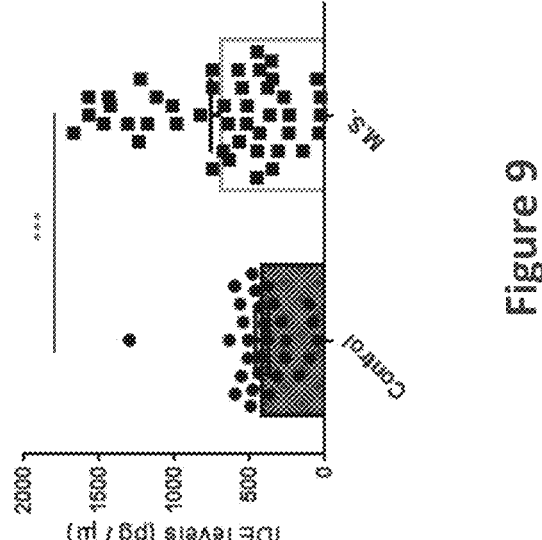
FIG. 9 demonstrates higher levels of IDE in the serum of MS patients (n=51) compared to control healthy subjects (n=24). Results are represented as mean±SEM; *** p<0.001.
Figure 10A:
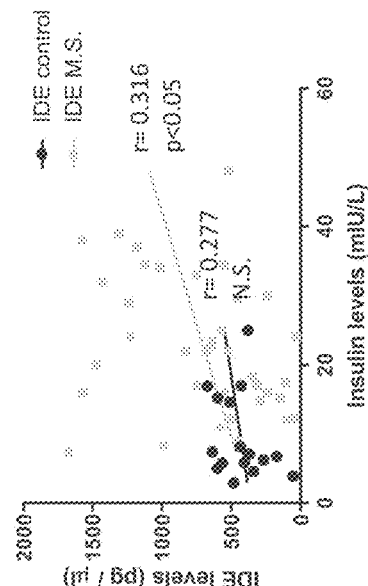
FIGS. 10A-C demonstrate correlation between serum IDE levels and components of MS: Triglycerides; r=0.423, p<0.01 (FIG. 10A), Insulin; r=0.294, p<0.05 (FIG. 10B); and HDLc; r=−0.366, p<0.05 (FIG. 10C).
Figure 10C:
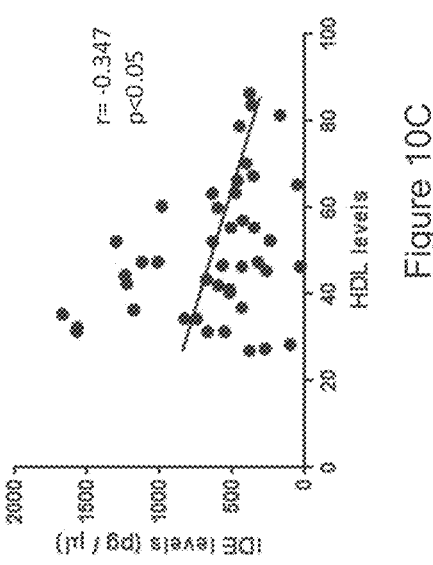
Figure 10B:
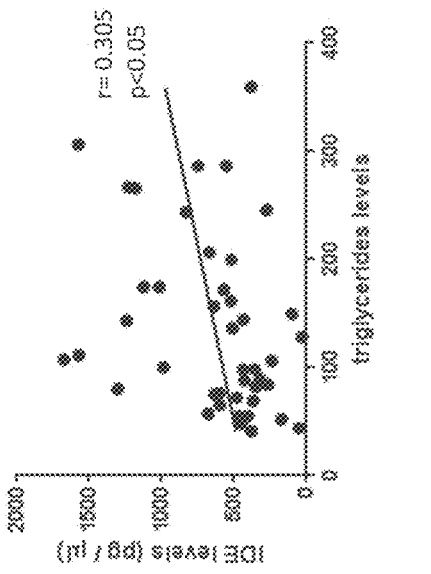

Following, the developed ELISA assay was used to determine IDE levels in serum samples of metabolic syndrome (MS) human patients and control healthy subjects. Compared to controls, MS subjects had higher BMI, glucose, triglycerides and insulin levels, with lower HDLc levels (Table 1 hereinbelow). The results demonstrate that IDE levels were higher in MS subjects (mean 637.4+/−469.5 vs 470.5+/−221.8 pg/µL; p<0.05) (FIG. 9). Since the MS group was older than the control group, IDE in the two groups was also compared following adjustment for age and again. Following this adjustment as well, IDE were higher in MS subjects compared with controls (F(1,68)=6.675, p=0.012, partial Eta-squared=0.089). Furthermore, a positive correlation between IDE levels and serum triglyceride (r=0.423; p<0.05, FIG. 10A) and insulin (r=0.294, p<0.05, FIG. 10B) and borderline correlation with serum c-peptide were detected (not shown). IDE was also negatively related to HDLc levels (r=−0.366; p<0.05, FIG. 10C). These findings suggest that higher IDE levels are quantitatively linked with MS components.

Moreover, IDE levels in MS subjects were clearly segregated into two different subgroups, subjects with low IDE, with value distribution and mean (n=25; 272.1+/−157.9 pg/µl) which were indistinguishable from the normal control group, and subjects with high IDE (n=25; 1002.6+/−383.7 pg/µl, p<0.001 for difference). The low IDE MS group were older (age 54+/−10 vs 45+/−13 years; p<0.05) and had higher glucose levels than the high IDE MS group (95+/−20 vs 80+/−9 mg/dl, p<0.01) (FIG. 9). Of note, insulin levels were found to be similar in both groups, as were triglycerides, HDLc, systolic and diastolic blood pressure and heart rate.

TABLE 1

| Subjects Characteristics [BP = Blood Pressure, HR-E ear Rate, Trig = triglycerides] | | | | | | | | | | | | |
|---|---|---|---|---|---|---|---|---|---|---|---|---|
| Group | N | Age years | Weight kg | Height (meter) | BMI kg/m² | Systolic BP | Diastolic BP | HR per min | Glucose mg/dl | Insulin µg/ml | HbA1c % | Trig mg/dl | HDL-c mg/dl |
| control | 24 | 38 +/− 12 | 73 +/− 16 | 1.66 +/− 0.08 | 26 +/− 5 | 115 +/− 11 | 71 +/− 10 | 66 +/− 17 | 73 +/− 10 | 9.5 +/− 6.2 | 5.4 +/− 0.2 | 79 +/− 40 | 61 +/− 16 |
| MS | 51 | 49 +/− 12 | 96 +/− 10 | 1.69 +/− 0.09 | 33 +/− 5 | 125 +/− 14 | 77 +/− 8 | 72 +/− 13 | 87 +/− 17 | 25 +/− 16 | 5.9 +/− 0.5 | 177 +/− 80 | 41 +/− 10 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited Throughout the Application

1. Alberti, K. G. M. M. and Zimmet, P. Z. (1998) Definition, diagnosis and classification of diabetes mellitus and its complications. Part 1: diagnosis and classification of diabetes mellitus. Provisional report of a WHO Consultation. *Diabet. Med.* 15, 539-553
2. Kahn, C. R. (1986) Insulin Resistance: A Common Feature of Diabetes Mellitus. *N. Engl. J. Med.*
3. Roglic, G. (2016) WHO Global report on diabetes: A summary. *Int. J. Noncommunicable Dis.* 1, 3-8
4. Vinik, A. I., Fishwick, D. T., and Pittenger, G. (2004) Advances in diabetes for the millennium: toward a cure for diabetes. *Medscape Gen. Med.* 6
5. Mortel, K. F., Meyer, J. S., Sims, P. A., and McClintic, K. (1990) Diabetes mellitus as a risk factor for stroke. *South. Med. J.* 83, 904-911
6. Falanga, V. (2005) Wound healing and its impairment in the diabetic foot. *Lancet* 366, 1736-1743
7. McCrimmon, R. J., Ryan, C. M., and Frier, B. M. (2012) Diabetes and cognitive dysfunction. *Lancet* 379, 2291-2299
8. Kleinridders, A., Ferris, H. A., Cai, W., and Kahn, C. R. (2014) Insulin action in brain regulates systemic metabolism and brain function.
9. Cheung, B. M. Y., Ong, K. L., Cherny, S. S., Sham, P.-C., Tso, A. W. K., and Lam, K. S. L. (2009) Diabetes Prevalence and Therapeutic Target Achievement in the United States, 1999 to 2006. *Am. J. Med.* 122, 443-453
10. Rines, A. K., Sharabi, K., Tavares, C. D. J., and Puigserver, P. (2016) Targeting hepatic glucose metabolism in the treatment of type 2 diabetes. *Nat. Rev. Drug Discov.* 15, 786-804
11. Binder, C., Lauritzen, T., Faber, O., and Pramming, S. (1984) *Insulin pharmacokinetics. Diabetes Care* 7, 188-199
12. Williams, G., Pickup, J. C., and Keen, H. (1987) Massive insulin resistance apparently due to rapid clearance of circulating insulin. *Am. J. Med.* 82, 1247-1252
13. Brunton, S. A., Davis, S. N., and Renda, S. M. (2006) Overcoming psychological barriers to insulin use in type 2 diabetes. *Clin. Cornerstone* 8, S19-S26
14. Porter, S. (2001) Human Immune Response to Recombinant Human Proteins. *J. Pharm. Sci.* 90, 1-11
15. Fernandez-Gamba, A., Leal, M., Morelli, L., and Castano, E. (2009) Insulin-Degrading Enzyme: Structure-Function Relationship and its Possible Roles in Health and Disease. *Curr. Pharm. Des.* 15, 3644-3655
16. M16: Pitrilysin: insulin degrading enzyme. *IUPHAR/BPS Guid. to Pharmacol.*
17. Guo, Q., Manolopoulou, M., Bian, Y., Schilling, A. B., and Tang, W.-J. (2010) Molecular Basis for the Recognition and Cleavages of IGF-II, TGF-α, and Amylin by Human Insulin-Degrading Enzyme. *J. Mol. Biol.* 395, 430-443
18. Duckworth, W. C. and Kitabchi, A. E. (1974) Insulin and glucagon degradation by the same enzyme. *Diabetes* 23, 536-543
19. Duckworth, W. C., Bennett, R. G., and Hamel, F. G. (1998) Insulin Degradation: Progress and Potential. *Endocr. Rev.* 19, 608-624
20. Hulse, R. E., Ralat, L. A., and Wei-Jen, T. (2009) Structure, Function, and Regulation of Insulin-Degrading Enzyme. *Vitam. Horm.* 80, 635-648
21. Glebov, K., Schiitze, S., and Walter, J. (2011) Functional relevance of a novel SlyX motif in non-conventional secretion of insulin-degrading enzyme. *J. Biol. Chem.* 286, 22711-22715
22. Maianti, J. P., McFedries, A., Foda, Z. H., Kleiner, R. E., Du, X. Q., Leissring, M. A., Tang, W.-J., Charron, M. J., Seeliger, M. A., Saghatelian, A., and Liu, D. R. (2014) Anti-diabetic activity of insulin-degrading enzyme inhibitors mediated by multiple hormones. *Nature* 511, 94-98
23. Yang, D., Qin, W., Shi, X., Zhu, B., Xie, M., Zhao, H., Teng, B., Wu, Y., Zhao, R., Yin, F., Ren, P., Liu, L., and Li, Z. (2018) Stabilized β-Hairpin Peptide Inhibits Insulin Degrading Enzyme. *J. Med. Chem.* 61, 8174-8185
24. Tang, W.-J. (2016) Targeting Insulin-Degrading Enzyme to Treat Type 2 Diabetes Mellitus. *Trends Endocrinol. Metab.* 27, 24-34
25. Deprez-Poulain, R., Hennuyer, N., Bosc, D., Liang, W. G., Enée, E., Marechal, X., Charton, J., Totobenazara, J., Berte, G., Jahklal, J., Verdelet, T., Dumont, J., Dassonneville, S., Woitrain, E., Gauriot, M., Paquet, C., Duplan, I., Hermant, P., Cantrelle, F.-X., Sevin, E., Culot, M., Landry, V., Herledan, A., Piveteau, C., Lippens, G., Leroux, F., Tang, W.-J., van Endert, P., Staels, B., and Deprez, B. (2015) Catalytic site inhibition of insulin-degrading enzyme by a small molecule induces glucose intolerance in mice. *Nat. Commun.* 6, 8250
26. Brekke, O. H. and Sandlie, I. (2003) Therapeutic antibodies for human diseases at the dawn of the twenty-first century. *Nat. Rev. Drug Discov.* 2, 52-62
27. Maynard, J. and Georgiou, G. (2000) Antibody Engineering. *Annu. Rev. Biomed. Eng.* 2, 339-376
28. Azriel-Rosenfeld, R., Valensi, M., and Benhar, I. (2004) A Human Synthetic Combinatorial Library of Arrayable Single-chain Antibodies based on Shuffling in Vivo Formed CDRs into General Framework Regions. *J. Mol. Biol.* 335, 177-192
29. Hakim, R. and Benhar, I. (2009) "Inclonals": IgGs and IgG-enzyme fusion proteins produced in an *E. coli* expression-refolding system. *MAbs* 1, 281-287
30. Buchner, J., Pastan, I., and Brinkmann, U. (1992) A method for increasing the yield of properly folded recombinant fusion proteins: Single-chain immunotoxins from renaturation of bacterial inclusion bodies. *Anal. Biochem.* 205, 263-270
31. Benhar, I. and Pastan, I. (1994) Cloning, expression and characterization of the Fv fragments of the anti-carbohydrate mAbs Bland B5 as single-chain immunotoxins. "*Protein Eng. Des. Sel.* 7, 1509-1515

32. Mazor, Y., Barnea, I., Keydar, I., and Benhar, I. (2007) Antibody internalization studied using a novel IgG binding toxin fusion. *J. Immunol. Methods* 321, 41-59

33. Birnboim-Perach, R., Grinberg, Y., Vaks, L., Nahary, L., and Benhar, I. (2019) Production of Stabilized Antibody Fragments in the *E. coli* Bacterial Cytoplasm and in Transiently Transfected Mammalian Cells. pp. 455-480, Humana Press, New York, NY 34. Gibson, D. G., Young, L., Chuang, R.-Y., Venter, J. C., Hutchison, C. A., and Smith, H. O. (2009) Enzymatic assembly of DNA molecules up to several hundred kilobases. *Nat. Methods* 6, 343-345

35. Perlman, R K., Gehm, B. D., Kuo, W.-L., and Rich Rosner, M. (1993) Functional Analysis of Conserved Residues in the Active Site of Insulin-degrading Enzyme. *J. Biol. Chem.* 268, 21538-21544

36. Morrison, S. L. and Schlom, J. (1990) Recombinant chimeric monoclonal antibodies. *Important Adv. Oncol.* 3-18

37. Murphy, A. J., Macdonald, L. E., Stevens, S., Karow, M., Dore, A. T., Pobursky, K., Huang, T. T., Poueymirou, W. T., Esau, L., Meola, M., Mikulka, W., Krueger, P., Fairhurst, J., Valenzuela, D. M., Papadopoulos, N., and Yancopoulos, G. D. Mice with megabase humanization of their immunoglobulin genes generate antibodies as efficiently as normal mice.

38. Maianti, J. P., McFedries, A., Foda, Z. H., Kleiner, R. E., Du, X. Q., Leissring, M. a, Tang, W.-J., Charron, M. J., Seeliger, M. a, Saghatelian, A., and Liu, D. R. (2014) Anti-diabetic activity of insulin-degrading enzyme inhibitors mediated by multiple hormones. *Nature* 511, 94-98

39. Leissring, M. a., Malito, E., Hedouin, S., Reinstatler, L., Sahara, T., Abdul-Hay, S. O., Choudhry, S., Maharvi, G. M., Fauq, A. H., Huzarska, M., May, P. S., Choi, S., Logan, T. P., Turk, B. E., Cantley, L. C., Manolopoulou, M., Tang, W.-J., Stein, R. L., Cuny, G. D., and Selkoe, D. J. (2010) Designed Inhibitors of Insulin-Degrading Enzyme Regulate the Catabolism and Activity of Insulin. *PLoS One* 5, e10504

40. Shen, Y., Joachimiak, A., Rosner, M. R., and Tang, W.-J. (2006) Structures of human insulin-degrading enzyme reveal a new substrate recognition mechanism. *Nature* 443, 870-874

41. Shen, Y., Joachimiak, A., Rich Rosner, M., and Tang, W.-J. (2006) Structures of human insulin-degrading enzyme reveal a new substrate recognition mechanism. *Nature* 443, 870-874

42. Farris, W., Mansourian, S., Chang, Y., Lindsley, L., Eckman, E A., Frosch, M. P., Eckman, C. B., Tanzi, R. E., Selkoe, D. J., and Guenette, S. (2003) Insulin-degrading enzyme regulates the levels of insulin, amyloid beta-protein, and the beta-amyloid precursor protein intracellular domain in vivo. *Proc Natl Acad Sci USA* 100, 4162-4167

43. Backer, J. M., Kahn, R. C., and White, M. F. (1990) The Dissociation and Degradation of Internalized Insulin Occur in the Endosomes of Rat Hepatoma Cells. *J. Biol. Chem.* 265, 14828-14835

44. Fakhrai-Rad, H., Nikoshkov, A., Kamel, A., Fernstrom, M., Zierath, J. R., Norgren, S., Luthman, H., and Galli, J. (2000) Insulin-degrading enzyme identified as a candidate diabetes susceptibility gene in GK rats. *Hum. Mol. Genet.* 9, 2149-2158

45. Karamohamed, S., Demissie, S., Volcjak, J., Liu, C. Y., Heard-Costa, N., Liu, J., Shoemaker, C. M., Panhuysen, C. I., Meigs, J. B., Wilson, P., Atwood, L. D., Cupples, L. a, and Herbert, a. (2003) Polymorphisms in the insulin-degrading enzyme gene are associated with type 2 diabetes in men from the NHLBI Framingham Heart Study. *Diabetes* 52, 1562-1567

46. Vieira, P. and Rajewsky, K. (1988) The half-lives of serum immunoglobulins in adult mice. *Eur. J. Immunol.* 18, 313-316

What is claimed is:

1. An isolated antibody comprising an antigen recognition region, which specifically binds insulin-degrading enzyme (IDE), wherein said antigen recognition domain comprises complementarity determining region (CDR) amino acid sequences as set forth in SEQ ID NOs: 36 (CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody.

2. A pharmaceutical composition comprising as an active ingredient the antibody of claim 1 and a pharmaceutically acceptable carrier.

3. A method for treating a disease associated with an IDE activity selected from the group consisting of diabetes and Parkinson's disease in a subject in need thereof, the method comprising administering to the subject a therapeutically effective amount of the antibody of claim 1, thereby treating the disease in the subject.

4. The method of claim 3, further comprising administering to said subject a therapeutic agent for treating said disease.

5. The method of claim 3, wherein said subject has a level of IDE above a predetermined threshold in a biological sample as compared to a control biological sample.

6. The antibody of claim 1, being an intact IgG antibody.

7. An isolated polynucleotide comprising a nucleic acid sequence encoding an antibody comprising an antigen recognition region, which specifically binds insulin-degrading enzyme (IDE), wherein said antigen recognition domain comprises complementarity determining region (CDR) amino acid sequences as set forth in SEQ ID NOs: 36 (CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody.

8. The isolated polynucleotide of claim 7, wherein nucleic acid sequences encoding said CDR amino acid sequences are as set forth in SEQ ID NOs: 35, 37, 39, 43, 45 and 47.

9. A method of producing an anti-insulin-degrading enzyme (IDE) antibody, the method comprising expressing in a host cell the polynucleotide of claim 7.

10. The method of claim 9, comprising isolating the antibody.

11. A host cell expressing an antibody comprising an antigen recognition region, which specifically binds insulin-degrading enzyme (IDE), wherein said antigen recognition domain comprises complementarity determining region (CDR) amino acid sequences as set forth in SEQ ID NOs: 36

(CDR1), 38 (CDR2) and 40 (CDR3), being sequentially arranged from N to C on a heavy chain of said antibody; and 44 (CDR1), 46 (CDR2) and 48 (CDR3), being sequentially arranged from N to C on a light chain of said antibody.

* * * * *

SEQUENCE LISTING

```
<160> NUMBER OF SEQ ID NOS: 52

<210> SEQ ID NO 1
<211> LENGTH: 375
<212> TYPE: DNA
<213> ORGANISM: Artificial sequence
<220> FEATURE:
<223> OTHER INFORMATION: Anti human IDE clone A9 VH

<400> SEQUENCE: 1
gaggtgcagc tgttggagtc tggggggaggc ttggtacagc ctggggggtc cctgagactc      60
tcctgtgcag cctctggatt caccttcaga agttatggca tgcactgggt ccgccaggct     120
ccagggaggg ggctggagtg ggtttcagcc attaatagta atggtgatag cacctactat     180
ccagacactg tgaaggaccg attcaccatc tccagagaca attccaagaa cacgctgtat     240
ctgcaaatga acagcctgag agccgaggac acggccgtgt attactgtgc gagagctgat     300
tattatgata gtactggcta ttactaccac ggtttggacc tctggggcca gggcaccctg     360
gtcacggtct cttca                                                      375

<210> SEQ ID NO 2
<211> LENGTH: 125
<212> TYPE: PRT
<213> ORGANISM: Artificial sequence
```

<220> FEATURE:
<223> OTHER INFORMATION: Anti human IDE clone A9 VH

<400> SEQUENCE: 2

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Arg Ser Tyr
            20                  25                  30

Gly Met His Trp Val Arg Gln Ala Pro Gly Arg Gly Leu Glu Trp Val
        35                  40                  45

Ser Ala Ile Asn Ser Asn Gly Asp Ser Thr Tyr Tyr Pro Asp Thr Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asp Tyr Tyr Asp Ser Thr Gly Tyr Tyr Tyr His Gly Leu
            100                 105                 110

Asp Leu Trp Gly Gln Gly Thr Leu Val Thr Val Ser Ser
        115                 120                 125
```

<210> SEQ ID NO 3
<211> LENGTH: 24
<212> TYPE: DNA
<213> ORGANISM: Artificial sequence
<220> FEATURE:
<223> OTHER INFORMATION: Anti human IDE (clone A9 VH) - CDR1 DNA
      sequence

<400> SEQUENCE: 3

```
ggattcacct tcagaagtta tggc                                          24
```

<210> SEQ ID NO 4
<211> LENGTH: 8
<212> TYPE: PRT
<213> ORGANISM: Artificial sequence
<220> FEATURE:
<223> OTHER INFORMATION: Anti human IDE (clone A9 VH) - CDR1

<400> SEQUENCE: 4

```
Gly Phe Thr Phe Arg Ser Tyr Gly
1               5
```

<210> SEQ ID NO 5
<211> LENGTH: 24
<212> TYPE: DNA
<213> ORGANISM: Artificial sequence
<220> FEATURE:
<223> OTHER INFORMATION: Anti human IDE (clone A9 VH) - CDR2 DNA
      sequence

<400> SEQUENCE: 5

```
attaatagta atggtgatag cacc                                          24
```

<210> SEQ ID NO 6
<211> LENGTH: 8
<212> TYPE: PRT
<213> ORGANISM: Artificial sequence
<220> FEATURE:
<223> OTHER INFORMATION: Anti human IDE (clone A9 VH) - CDR2

<400> SEQUENCE: 6

```
Ile Asn Ser Asn Gly Asp Ser Thr
```

-continued 1              5

<210> SEQ ID NO 7
<211> LENGTH: 55
<212> TYPE: DNA
<213> ORGANISM: Artificial sequence
<220> FEATURE:
<223> OTHER INFORMATION: Anti human IDE (clone A9 VH) - CDR3 DNA
      sequence

<400> SEQUENCE: 7
gcgagaagct gattattatg atagtactgg ctattactac cacggtttgg acctc          55

<210> SEQ ID NO 8
<211> LENGTH: 18
<212> TYPE: PRT
<213> ORGANISM: Artificial sequence
<220> FEATURE:
<223> OTHER INFORMATION: Anti human IDE (clone A9 VH) - CDR3

<400> SEQUENCE: 8

Ala Arg Ala Asp Tyr Tyr Asp Ser Thr Gly Tyr Tyr Tyr His Gly Leu
1               5                   10                  15

Asp Leu

<210> SEQ ID NO 9
<211> LENGTH: 324
<212> TYPE: DNA
<213> ORGANISM: Artificial sequence
<220> FEATURE:
<223> OTHER INFORMATION: Anti human IDE clone A9 VL - DNA sequence

<400> SEQUENCE: 9
gatatcgtgc tgactcagcc accctcagcg tctgggaccc ccgggcagag ggtcaccatc      60
tcctgctctg gaagcaggga caacatcggg aagaattatg tgtcctggta ccagcagctc     120
ccaggaacgg ctcccaaact cctcatctat aggaataatc agcggccctc aggggtccct     180
gaccggttct ctggctccaa gtctggcacc tcagcctccc tggccatcag tgggctgcgg     240
tccgaggatg aggctgatta ttactgctcc tcatatgcag gcagctccgt gatattcggc     300
ggaggcacca aggtgaccgt ccta                                            324

<210> SEQ ID NO 10
<211> LENGTH: 108
<212> TYPE: PRT
<213> ORGANISM: Artificial sequence
<220> FEATURE:
<223> OTHER INFORMATION: Anti human IDE clone A9 VL

<400> SEQUENCE: 10

Asp Ile Val Leu Thr Gln Pro Pro Ser Ala Ser Gly Thr Pro Gly Gln
1               5                   10                  15

Arg Val Thr Ile Ser Cys Ser Gly Ser Arg Asp Asn Ile Gly Lys Asn
            20                  25                  30

Tyr Val Ser Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ser Ser Tyr Ala Gly Ser Ser
                85                  90                  95

```
Val Ile Phe Gly Gly Gly Thr Lys Val Thr Val Leu
            100                 105

<210> SEQ ID NO 11
<211> LENGTH: 24
<212> TYPE: DNA
<213> ORGANISM: Artificial sequence
<220> FEATURE:
<223> OTHER INFORMATION: Anti human IDE (clone A9 VL) - CDR1 DNA
      sequence

<400> SEQUENCE: 11
agggacaaca tcgggaagaa ttat                                            24

<210> SEQ ID NO 12
<211> LENGTH: 8
<212> TYPE: PRT
<213> ORGANISM: Artificial sequence
<220> FEATURE:
<223> OTHER INFORMATION: Anti human IDE (clone A9 VL) - CDR1

<400> SEQUENCE: 12

Arg Asp Asn Ile Gly Lys Asn Tyr
1               5

<210> SEQ ID NO 13
<211> LENGTH: 9
<212> TYPE: DNA
<213> ORGANISM: Artificial sequence
<220> FEATURE:
<223> OTHER INFORMATION: Anti human IDE (clone A9 VL) - CDR2 DNA
      sequence

<400> SEQUENCE: 13 aggaataat                                                             9

<210> SEQ ID NO 14
<211> LENGTH: 3
<212> TYPE: PRT
<213> ORGANISM: Artificial sequence
<220> FEATURE:
<223> OTHER INFORMATION: Anti human IDE (clone A9 VL) - CDR2

<400> SEQUENCE: 14

Arg Asn Asn
1

<210> SEQ ID NO 15
<211> LENGTH: 27
<212> TYPE: DNA
<213> ORGANISM: Artificial sequence
<220> FEATURE:
<223> OTHER INFORMATION: Anti human IDE (clone A9 VL) - CDR3 DNA
      sequence

<400> SEQUENCE: 15
tcctcatatg caggcagctc cgtgata                                         27

<210> SEQ ID NO 16
<211> LENGTH: 9
<212> TYPE: PRT
<213> ORGANISM: Artificial sequence
<220> FEATURE:
<223> OTHER INFORMATION: Anti human IDE (clone A9 VL) - CDR3

<400> SEQUENCE: 16
```

```
Ser Ser Tyr Ala Gly Ser Ser Val Ile
1               5
```

<210> SEQ ID NO 17
<211> LENGTH: 369
<212> TYPE: DNA
<213> ORGANISM: Artificial sequence
<220> FEATURE:
<223> OTHER INFORMATION: Anti human IDE clone B1 VH - DNA sequence

<400> SEQUENCE: 17

```
gaggtgcagc tgttggagtc tggggggaggc ttggtacagc ctggggggtc cctgagactc       60
tcctgtgcag cctctggatt caccttcggt tcctactgga tgcactgggt ccgccaggct      120
ccaggcaagg ggctggagtg ggtctcagga attagtggaa gtggacatac cacatactac      180
gcagacgccg tgaagggccg gttcaccatc tccagagaca attccaagaa cacgctgtat      240
ctgcaaatga acagcctgag agccgaggac acggccgtat attactgtgc gagacaaggg      300
gacttcgatc tctggagtgg ttatcctttt gactcctggg gccagggcac cctggtcacg      360
gtctcctca                                                             369
```

<210> SEQ ID NO 18
<211> LENGTH: 123
<212> TYPE: PRT
<213> ORGANISM: Artificial sequence
<220> FEATURE:
<223> OTHER INFORMATION: Anti human IDE clone B1 VH

<400> SEQUENCE: 18

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Trp Met His Trp Val Arg Gln Ala Pro Gly Lys Gly Leu Glu Trp Val
        35                  40                  45

Ser Gly Ile Ser Gly Ser Gly His Thr Thr Tyr Tyr Ala Asp Ala Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Phe Asp Leu Trp Ser Gly Tyr Pro Phe Asp Ser
            100                 105                 110

Trp Gly Gln Gly Thr Leu Val Thr Val Ser Ser
        115                 120
```

<210> SEQ ID NO 19
<211> LENGTH: 24
<212> TYPE: DNA
<213> ORGANISM: Artificial sequence
<220> FEATURE:
<223> OTHER INFORMATION: Anti human IDE (clone B1 VH) - CDR1 DNA
      sequence

<400> SEQUENCE: 19

```
ggattcacct tcggttccta ctgg                                            24
```

<210> SEQ ID NO 20
<211> LENGTH: 8
<212> TYPE: PRT
<213> ORGANISM: Artificial sequence -continued

```
<220> FEATURE:
<223> OTHER INFORMATION: Anti human IDE (clone B1 VH) - CDR1

<400> SEQUENCE: 20

Gly Phe Thr Phe Gly Ser Tyr Trp
1               5

<210> SEQ ID NO 21
<211> LENGTH: 24
<212> TYPE: DNA
<213> ORGANISM: Artificial sequence
<220> FEATURE:
<223> OTHER INFORMATION: Anti human IDE (clone B1 VH) - CDR2 DNA
      sequence

<400> SEQUENCE: 21
attagtggaa gtggacatac caca                                         24

<210> SEQ ID NO 22
<211> LENGTH: 8
<212> TYPE: PRT
<213> ORGANISM: Artificial sequence
<220> FEATURE:
<223> OTHER INFORMATION: Anti human IDE (clone B1 VH) - CDR2

<400> SEQUENCE: 22

Ile Ser Gly Ser Gly His Thr Thr
1               5

<210> SEQ ID NO 23
<211> LENGTH: 48
<212> TYPE: DNA
<213> ORGANISM: Artificial sequence
<220> FEATURE:
<223> OTHER INFORMATION: Anti human IDE (clone B1 VH) - CDR3 DNA
      sequence

<400> SEQUENCE: 23
gcgagacaag gggacttcga tctctggagt ggttatcctt ttgactcc               48

<210> SEQ ID NO 24
<211> LENGTH: 16
<212> TYPE: PRT
<213> ORGANISM: Artificial sequence
<220> FEATURE:
<223> OTHER INFORMATION: Anti human IDE (clone B1 VH) - CDR3

<400> SEQUENCE: 24

Ala Arg Gln Gly Asp Phe Asp Leu Trp Ser Gly Tyr Pro Phe Asp Ser
1               5                   10                  15

<210> SEQ ID NO 25
<211> LENGTH: 321
<212> TYPE: DNA
<213> ORGANISM: Artificial sequence
<220> FEATURE:
<223> OTHER INFORMATION: Anti human IDE clone B1 VL (Kappa) - DNA
      sequence

<400> SEQUENCE: 25
gatatcgtgt tgacgcagtc tccaggcacc ctgtctttgt ctccagggga aagagccacc    60
ctctcctgca gggccagtca gagtgttagc agtcacttgg cctggtacca gcagaaacct   120
ggccaggctc ccaggctcct catctatgat gcatccaaca gggccactgg catcccagac   180
aggttcagtg gcagtgggtc tgggacagac ttcactctca ccatcagcag actggagcct   240
```

-continued

```
gaagattttg cagtgtatta ctgtcaacag tatgatagtt atccgtacac ttttggccag    300
gggaccaaac tggacatcaa a                                              321
```

```
<210> SEQ ID NO 26
<211> LENGTH: 107
<212> TYPE: PRT
<213> ORGANISM: Artificial sequence
<220> FEATURE:
<223> OTHER INFORMATION: Anti human IDE clone B1 VL (Kappa)

<400> SEQUENCE: 26

Asp Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser His
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Asp Ser Tyr Pro Tyr
                85                  90                  95

Thr Phe Gly Gln Gly Thr Lys Leu Asp Ile Lys
            100                 105
```

```
<210> SEQ ID NO 27
<211> LENGTH: 18
<212> TYPE: DNA
<213> ORGANISM: Artificial sequence
<220> FEATURE:
<223> OTHER INFORMATION: Anti human IDE (clone B1 VL) - CDR1 DNA
      sequence

<400> SEQUENCE: 27
cagagtgtta gcagtcac                                                  18
```

```
<210> SEQ ID NO 28
<211> LENGTH: 6
<212> TYPE: PRT
<213> ORGANISM: Artificial sequence
<220> FEATURE:
<223> OTHER INFORMATION: Anti human IDE (clone B1 VL) - CDR1

<400> SEQUENCE: 28

Gln Ser Val Ser Ser His
1               5
```

```
<210> SEQ ID NO 29
<211> LENGTH: 9
<212> TYPE: DNA
<213> ORGANISM: Artificial sequence
<220> FEATURE:
<223> OTHER INFORMATION: Anti human IDE (clone B1 VL) - CDR2 DNA
      sequence

<400> SEQUENCE: 29 gatgcatcc                                                            9
```

```
<210> SEQ ID NO 30
<211> LENGTH: 3
<212> TYPE: PRT
<213> ORGANISM: Artificial sequence
```

<220> FEATURE:
<223> OTHER INFORMATION: Anti human IDE (clone B1 VL) - CDR2

<400> SEQUENCE: 30

Asp Ala Ser
1

<210> SEQ ID NO 31
<211> LENGTH: 27
<212> TYPE: DNA
<213> ORGANISM: Artificial sequence
<220> FEATURE:
<223> OTHER INFORMATION: Anti human IDE (clone B1 VL) - CDR3 DNA
      sequence

<400> SEQUENCE: 31
caacagtatg atagttatcc gtacact                                          27

<210> SEQ ID NO 32
<211> LENGTH: 9
<212> TYPE: PRT
<213> ORGANISM: Artificial sequence
<220> FEATURE:
<223> OTHER INFORMATION: Anti human IDE (clone B1 VL) - CDR3

<400> SEQUENCE: 32

Gln Gln Tyr Asp Ser Tyr Pro Tyr Thr
1               5

<210> SEQ ID NO 33
<211> LENGTH: 369
<212> TYPE: DNA
<213> ORGANISM: Artificial sequence
<220> FEATURE:
<223> OTHER INFORMATION: Anti human IDE clone H3 VH - DNA sequence

<400> SEQUENCE: 33
gaggtgcagc tgttggagtc tggggggaggc ttggtacagc ctgggggggtc cctgagactc     60 tcctgtgcag cctctggatt caccttcagt aactactgga tgcactgggt ccgccaggct    120
ccagggaagg ggctggagtg ggtttcaact attagtggtc gtggtagtgc cacacactac    180
acagactccg tgaagggccg gttcaccatc tccagagaca attccaagaa cacgctgtat    240
ctgcaaatga acagcctgag agccgaggac acggccgtat attactgtgc gagacaaggg    300
gacttcgatc tctggagtgg ttatcctttt gactcctggg gccagggcac cctggtcacg    360
gtctcctca                                                           369

<210> SEQ ID NO 34
<211> LENGTH: 123
<212> TYPE: PRT
<213> ORGANISM: Artificial sequence
<220> FEATURE:
<223> OTHER INFORMATION: Anti human IDE clone H3 VH

<400> SEQUENCE: 34

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met His Trp Val Arg Gln Ala Pro Gly Lys Gly Leu Glu Trp Val
        35                  40                  45

Ser Thr Ile Ser Gly Arg Gly Ser Ala Thr His Tyr Thr Asp Ser Val
    50                  55                  60

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gln Gly Asp Phe Asp Leu Trp Ser Gly Tyr Pro Phe Asp Ser
            100                 105                 110

Trp Gly Gln Gly Thr Leu Val Thr Val Ser Ser
        115                 120
```

```
<210> SEQ ID NO 35
<211> LENGTH: 24
<212> TYPE: DNA
<213> ORGANISM: Artificial sequence
<220> FEATURE:
<223> OTHER INFORMATION: Anti human IDE (clone H3 VH) - CDR1 DNA
      sequence

<400> SEQUENCE: 35
ggattcacct tcagtaacta ctgg                                        24

<210> SEQ ID NO 36
<211> LENGTH: 8
<212> TYPE: PRT
<213> ORGANISM: Artificial sequence
<220> FEATURE:
<223> OTHER INFORMATION: Anti human IDE (clone H3 VH) - CDR1

<400> SEQUENCE: 36

Gly Phe Thr Phe Ser Asn Tyr Trp
1               5

<210> SEQ ID NO 37
<211> LENGTH: 24
<212> TYPE: DNA
<213> ORGANISM: Artificial sequence
<220> FEATURE:
<223> OTHER INFORMATION: Anti human IDE (clone H3 VH) - CDR2 DNA
      sequence

<400> SEQUENCE: 37
attagtggtc gtggtagtgc caca                                        24

<210> SEQ ID NO 38
<211> LENGTH: 8
<212> TYPE: PRT
<213> ORGANISM: Artificial sequence
<220> FEATURE:
<223> OTHER INFORMATION: Anti human IDE (clone H3 VH) - CDR2

<400> SEQUENCE: 38

Ile Ser Gly Arg Gly Ser Ala Thr
1               5

<210> SEQ ID NO 39
<211> LENGTH: 48
<212> TYPE: DNA
<213> ORGANISM: Artificial sequence
<220> FEATURE:
<223> OTHER INFORMATION: Anti human IDE (clone H3 VH) - CDR3 DNA
      sequence

<400> SEQUENCE: 39
gcgagacaag gggacttcga tctctggagt ggttatcctt ttgactcc              48
```

```
<210> SEQ ID NO 40
<211> LENGTH: 16
<212> TYPE: PRT
<213> ORGANISM: Artificial sequence
<220> FEATURE:
<223> OTHER INFORMATION: Anti human IDE (clone H3 VH) - CDR3

<400> SEQUENCE: 40

Ala Arg Gln Gly Asp Phe Asp Leu Trp Ser Gly Tyr Pro Phe Asp Ser
1               5                   10                  15

<210> SEQ ID NO 41
<211> LENGTH: 330
<212> TYPE: DNA
<213> ORGANISM: Artificial sequence
<220> FEATURE:
<223> OTHER INFORMATION: Anti human IDE clone H3 VL (Lambda) - DNA
      sequence

<400> SEQUENCE: 41
gatatcgtgc tgactcagcc accctcagcg tctgggaccc ccgggcagag ggtcaccatc      60
tcttgcactg gaagcagctc caacattggg aatagttatg tagcctggta ccagcagctt     120
ccaggaacgg ctcccaaact cctcatttat gacaatgata gcgaccctc aggggtccct       180 gaccggttct ctggctccaa gtctggcacc tcagcctccc tggccatcag tgggctccgg     240
tccgaggatg aggctgatta ttactgccag tcctatgaca gcagcctgag tggttggatg     300
ttcggcggag ggaccaagct caccgtccta                                      330

<210> SEQ ID NO 42
<211> LENGTH: 110
<212> TYPE: PRT
<213> ORGANISM: Artificial sequence
<220> FEATURE:
<223> OTHER INFORMATION: Anti human IDE clone H3 VL (Lambda)

<400> SEQUENCE: 42

Asp Ile Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Asn Ser
                20                  25                  30

Tyr Val Ala Trp Tyr Gln Gln Leu Pro Gly Thr Ala Pro Lys Leu Leu
        35                  40                  45

Ile Tyr Asp Asn Asp Lys Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Ser Gly Trp Met Phe Gly Gly Gly Thr Lys Leu Thr Val Leu
            100                 105                 110

<210> SEQ ID NO 43
<211> LENGTH: 24
<212> TYPE: DNA
<213> ORGANISM: Artificial sequence
<220> FEATURE:
<223> OTHER INFORMATION: Anti human IDE (clone H3 VL) - CDR1 DNA
      sequence

<400> SEQUENCE: 43
agctccaaca ttgggaatag ttat                                             24
```

```
<210> SEQ ID NO 44
<211> LENGTH: 8
<212> TYPE: PRT
<213> ORGANISM: Artificial sequence
<220> FEATURE:
<223> OTHER INFORMATION: Anti human IDE (clone H3 VL) - CDR1

<400> SEQUENCE: 44

Ser Ser Asn Ile Gly Asn Ser Tyr
1               5

<210> SEQ ID NO 45
<211> LENGTH: 9
<212> TYPE: DNA
<213> ORGANISM: Artificial sequence
<220> FEATURE:
<223> OTHER INFORMATION: Anti human IDE (clone H3 VL) - CDR2 DNA
      sequence

<400> SEQUENCE: 45 gacaatgat                                                           9

<210> SEQ ID NO 46
<211> LENGTH: 3
<212> TYPE: PRT
<213> ORGANISM: Artificial sequence
<220> FEATURE:
<223> OTHER INFORMATION: Anti human IDE (clone H3 VL) - CDR2

<400> SEQUENCE: 46

Asp Asn Asp
1

<210> SEQ ID NO 47
<211> LENGTH: 33
<212> TYPE: DNA
<213> ORGANISM: Artificial sequence
<220> FEATURE:
<223> OTHER INFORMATION: Anti human IDE (clone H3 VL) - CDR3 DNA
      sequence

<400> SEQUENCE: 47
cagtcctatg acagcagcct gagtggttgg atg                                33

<210> SEQ ID NO 48
<211> LENGTH: 11
<212> TYPE: PRT
<213> ORGANISM: Artificial sequence
<220> FEATURE:
<223> OTHER INFORMATION: Anti human IDE (clone H3 VL) - CDR3

<400> SEQUENCE: 48

Gln Ser Tyr Asp Ser Ser Leu Ser Gly Trp Met
1               5                   10

<210> SEQ ID NO 49
<211> LENGTH: 2976
<212> TYPE: DNA
<213> ORGANISM: Artificial sequence
<220> FEATURE:
<223> OTHER INFORMATION: Wild type IDE coding sequence

<400> SEQUENCE: 49
atgaataatc ctgcaatcaa gcgtattggt aaccatatta ccaagagccc ggaggacaaa     60
cgtgagtatc gcggcctgga actggccaat ggcatcaagg ttctgctgat cagcgacccg    120
```

-continued

```
acaaccgaca agagtagtgc agccctggat gtgcatattg gcagcctgag tgatccgcct      180
aacattgccg gtctgagcca cttctgcgaa cacatgctgt tcctgggcac caaaaagtac      240
ccgaaagaaa acgagtatag tcagtttctg agcgagcacg caggtagtag caatgccttc      300
acaagcggtg agcacaccaa ttactacttc gacgtgagcc atgaacatct ggagggcgca      360
ctggatcgct ttgcccaatt ctttctgtgc ccgctgtttg acgaaagctg caaagaccgt      420
gaggtgaacg ccgttgatag cgagcacgag aaaaacgtta tgaacgacgc ctggcgctta      480
ttccagctgg agaaggcaac cggtaacccg aaacacccgt ttagtaagtt cggcacaggc      540
aacaagtaca ccttagaaac ccgccctaac caggagggca ttgacgtgcg ccaagagtta      600
ttaaaatttc acagcgcata ctacagcagc aacctgatgg cagtgtgtgt tctgggccgc      660
gaaagcctgg atgatctgac aaatctggtt gttaaattat tcagtgaggt ggagaacaag      720
aacgtgccgc tgcctgagtt tcctgagcac ccgttccagg aggaacattt aaagcaactg      780
tataaaattg tgccgatcaa agacattcgc aatctgtatg ttacattccc gatcccggac      840
ctgcaaaagt actacaagag caacccgggt cactacttag gccatctgat tggccacgag      900
ggtccgggca gtctgctgag tgaactgaag agcaagggtt gggtgaacac actggttggt      960
ggccagaagg agggcgcacg tggtttcatg ttctttatta tcaatgtgga cctgaccgaa     1020
gaaggtctgc tgcacgtgga ggacatcatc ttacacatgt ttcagtacat tcagaaatta     1080
cgcgcagaag gtccgcagga gtgggtgttc caagagtgca aggatctgaa cgcagtggcc     1140
ttccgcttta aagacaaaga gcgtccgcgc ggctatacca gtaaaattgc aggtatctta     1200
cactactacc cgctggagga ggtttttaaca gccgagtatc tgctggaaga attccgcccg     1260
gacttaatcg agatggtgct ggacaagtta cgcccggaga acgtgcgtgt tgccattgtg     1320
agcaagagct tcgagggcaa gaccgaccgt accgaagagt ggtacggtac acagtacaag     1380
caggaggcca tccctgatga ggttattaag aagtggcaaa atgccgacct gaatggtaag     1440
tttaagttac cgacaaagaa cgaattcatc ccgaccaact ttgaaatcct gccgctggaa     1500
aaggaagcca ccccgtatcc tgcactgatt aaggacaccg ccatgagcaa attatggttc     1560
aagcaggacg acaaattctt cctgccgaag gcctgcctga atttcgagtt cttcagcccg     1620
ttcgcctacg ttgatccgct gcactgtaat atggcctact tatacctgga gttactgaaa     1680
gacagcttaa atgagtatgc atacgccgca gagctggccg gtttaagcta cgacctgcaa     1740
aataccattt atggcatgta tttaagcgtg aagggctaca cgataaaca accgatctta     1800 ctgaagaaaa ttattgaaaa aatggccacc tttgaaatcg acgagaagcg ttttgaaatt     1860
attaaagagg catatatgcg tagcctgaac aattttcgcg ccgaacaacc gcaccagcac     1920
gcaatgtact acctgcgctt actgatgacc gaagttgcct ggaccaaaga cgagctgaag     1980
gaagccctgg acgatgtgac cttaccgcgt ttaaaggcct tcatcccgca attactgagt     2040
cgtctgcaca ttgaggccct gttacacggt aacatcacca agcaagccgc actgggcatt     2100
atgcagatgg ttgaggatac cctgatcgag cacgcccaca ccaaaccgtt actgccgagt     2160
caactggtgc gctatcgcga agtgcaactg cctgatcgtg gctggtttgt gtatcagcag     2220
cgtaatgagt gcacaacaa ctgtggtatc gaaatctact accaaaccga catgcaaagc     2280
accagcgaga acatgttcct ggagctgttt tgccagatca tcagcgaacc gtgcttcaac     2340
accctgcgca ccaaggagca attaggctac atcgtgttca gtggccctcg tcgcgcaaat     2400
ggtatccagg gcttacgctt catcatccag agtgaaaaac cgccgcacta cctggaaagt     2460
cgtgttgaag cattttttaat cacgatggaa aagagcatcg aggacatgac cgaggaggcc     2520
```

-continued

```
ttccagaagc acatccaagc cctggcaatc cgtcgcttag ataagccgaa gaagctgagt     2580
gccgagtgcg ccaagtactg gggtgagatc attagccagc agtacaattt cgaccgcgac     2640
aacaccgagg ttgcatacct gaaaaccctg accaaagaag acatcatcaa attttacaag     2700
gagatgttag cagtggatgc accgcgtcgc cataaagtta gcgttcatgt gctggcacgc     2760
gagatggata gttgtccggt ggttggtgaa ttcccgtgcc agaatgacat caacctgagc     2820
caagcacctg ccttaccgca accggaggtg atccagaaca tgacagaatt caagcgcggc     2880
ctgccgttat tcccgttagt gaagccgcac atcaacttca tggccgcaaa attaaagctt     2940
gcggccgcac tcgagcacca ccaccaccac cactga                               2976
```

```
<210> SEQ ID NO 50
<211> LENGTH: 991
<212> TYPE: PRT
<213> ORGANISM: Artificial sequence
<220> FEATURE:
<223> OTHER INFORMATION: Wild type IDE polypeptide sequence

<400> SEQUENCE: 50

Met Asn Asn Pro Ala Ile Lys Arg Ile Gly Asn His Ile Thr Lys Ser
1               5                   10                  15

Pro Glu Asp Lys Arg Glu Tyr Arg Gly Leu Glu Leu Ala Asn Gly Ile
                20                  25                  30

Lys Val Leu Leu Ile Ser Asp Pro Thr Thr Asp Lys Ser Ser Ala Ala
            35                  40                  45

Leu Asp Val His Ile Gly Ser Leu Ser Asp Pro Pro Asn Ile Ala Gly
        50                  55                  60

Leu Ser His Phe Cys Glu His Met Leu Phe Leu Gly Thr Lys Lys Tyr
65                  70                  75                  80

Pro Lys Glu Asn Glu Tyr Ser Gln Phe Leu Ser Glu His Ala Gly Ser
                85                  90                  95

Ser Asn Ala Phe Thr Ser Gly Glu His Thr Asn Tyr Tyr Phe Asp Val
            100                 105                 110

Ser His Glu His Leu Glu Gly Ala Leu Asp Arg Phe Ala Gln Phe Phe
        115                 120                 125

Leu Cys Pro Leu Phe Asp Glu Ser Cys Lys Asp Arg Glu Val Asn Ala
    130                 135                 140

Val Asp Ser Glu His Glu Lys Asn Val Met Asn Asp Ala Trp Arg Leu
145                 150                 155                 160

Phe Gln Leu Glu Lys Ala Thr Gly Asn Pro Lys His Pro Phe Ser Lys
                165                 170                 175

Phe Gly Thr Gly Asn Lys Tyr Thr Leu Glu Thr Arg Pro Asn Gln Glu
            180                 185                 190

Gly Ile Asp Val Arg Gln Glu Leu Leu Lys Phe His Ser Ala Tyr Tyr
        195                 200                 205

Ser Ser Asn Leu Met Ala Val Cys Val Leu Gly Arg Glu Ser Leu Asp
    210                 215                 220

Asp Leu Thr Asn Leu Val Val Lys Leu Phe Ser Glu Val Glu Asn Lys
225                 230                 235                 240

Asn Val Pro Leu Pro Glu Phe Pro Glu His Pro Phe Gln Glu Glu His
                245                 250                 255

Leu Lys Gln Leu Tyr Lys Ile Val Pro Ile Lys Asp Ile Arg Asn Leu
            260                 265                 270

Tyr Val Thr Phe Pro Ile Pro Asp Leu Gln Lys Tyr Tyr Lys Ser Asn
```

-continued

```
           275                 280                 285

Pro Gly His Tyr Leu Gly His Leu Ile Gly His Glu Gly Pro Gly Ser
    290                 295                 300

Leu Leu Ser Glu Leu Lys Ser Lys Gly Trp Val Asn Thr Leu Val Gly
305                 310                 315                 320

Gly Gln Lys Glu Gly Ala Arg Gly Phe Met Phe Ile Ile Asn Val
                325                 330                 335

Asp Leu Thr Glu Glu Gly Leu Leu His Val Glu Asp Ile Ile Leu His
                340                 345                 350

Met Phe Gln Tyr Ile Gln Lys Leu Arg Ala Glu Gly Pro Gln Glu Trp
                355                 360                 365

Val Phe Gln Glu Cys Lys Asp Leu Asn Ala Val Ala Phe Arg Phe Lys
    370                 375                 380

Asp Lys Glu Arg Pro Arg Gly Tyr Thr Ser Lys Ile Ala Gly Ile Leu
385                 390                 395                 400

His Tyr Tyr Pro Leu Glu Glu Val Leu Thr Ala Glu Tyr Leu Leu Glu
                405                 410                 415

Glu Phe Arg Pro Asp Leu Ile Glu Met Val Leu Asp Lys Leu Arg Pro
                420                 425                 430

Glu Asn Val Arg Val Ala Ile Val Ser Lys Ser Phe Glu Gly Lys Thr
                435                 440                 445

Asp Arg Thr Glu Glu Trp Tyr Gly Thr Gln Tyr Lys Gln Glu Ala Ile
    450                 455                 460

Pro Asp Glu Val Ile Lys Lys Trp Gln Asn Ala Asp Leu Asn Gly Lys
465                 470                 475                 480

Phe Lys Leu Pro Thr Lys Asn Glu Phe Ile Pro Thr Asn Phe Glu Ile
                485                 490                 495

Leu Pro Leu Glu Lys Glu Ala Thr Pro Tyr Pro Ala Leu Ile Lys Asp
                500                 505                 510

Thr Ala Met Ser Lys Leu Trp Phe Lys Gln Asp Asp Lys Phe Phe Leu
                515                 520                 525

Pro Lys Ala Cys Leu Asn Phe Glu Phe Phe Ser Pro Phe Ala Tyr Val
    530                 535                 540

Asp Pro Leu His Cys Asn Met Ala Tyr Leu Tyr Leu Glu Leu Leu Lys
545                 550                 555                 560

Asp Ser Leu Asn Glu Tyr Ala Tyr Ala Ala Glu Leu Ala Gly Leu Ser
                565                 570                 575

Tyr Asp Leu Gln Asn Thr Ile Tyr Gly Met Tyr Leu Ser Val Lys Gly
                580                 585                 590

Tyr Asn Asp Lys Gln Pro Ile Leu Leu Lys Lys Ile Ile Glu Lys Met
                595                 600                 605

Ala Thr Phe Glu Ile Asp Glu Lys Arg Phe Glu Ile Ile Lys Glu Ala
    610                 615                 620

Tyr Met Arg Ser Leu Asn Asn Phe Arg Ala Glu Gln Pro His Gln His
625                 630                 635                 640

Ala Met Tyr Tyr Leu Arg Leu Leu Met Thr Glu Val Ala Trp Thr Lys
                645                 650                 655

Asp Glu Leu Lys Glu Ala Leu Asp Asp Val Thr Leu Pro Arg Leu Lys
                660                 665                 670

Ala Phe Ile Pro Gln Leu Leu Ser Arg Leu His Ile Glu Ala Leu Leu
    675                 680                 685

His Gly Asn Ile Thr Lys Gln Ala Ala Leu Gly Ile Met Gln Met Val
    690                 695                 700
```

-continued

```
Glu Asp Thr Leu Ile Glu His Ala His Thr Lys Pro Leu Leu Pro Ser
705                 710                 715                 720

Gln Leu Val Arg Tyr Arg Glu Val Gln Leu Pro Asp Arg Gly Trp Phe
                725                 730                 735

Val Tyr Gln Gln Arg Asn Glu Val His Asn Asn Cys Gly Ile Glu Ile
            740                 745                 750

Tyr Tyr Gln Thr Asp Met Gln Ser Thr Ser Glu Asn Met Phe Leu Glu
        755                 760                 765

Leu Phe Cys Gln Ile Ile Ser Glu Pro Cys Phe Asn Thr Leu Arg Thr
    770                 775                 780

Lys Glu Gln Leu Gly Tyr Ile Val Phe Ser Gly Pro Arg Arg Ala Asn
785                 790                 795                 800

Gly Ile Gln Gly Leu Arg Phe Ile Ile Gln Ser Glu Lys Pro Pro His
                805                 810                 815

Tyr Leu Glu Ser Arg Val Glu Ala Phe Leu Ile Thr Met Glu Lys Ser
            820                 825                 830

Ile Glu Asp Met Thr Glu Glu Ala Phe Gln Lys His Ile Gln Ala Leu
        835                 840                 845

Ala Ile Arg Arg Leu Asp Lys Pro Lys Lys Leu Ser Ala Glu Cys Ala
    850                 855                 860

Lys Tyr Trp Gly Glu Ile Ile Ser Gln Gln Tyr Asn Phe Asp Arg Asp
865                 870                 875                 880

Asn Thr Glu Val Ala Tyr Leu Lys Thr Leu Thr Lys Glu Asp Ile Ile
                885                 890                 895

Lys Phe Tyr Lys Glu Met Leu Ala Val Asp Ala Pro Arg Arg His Lys
                900                 905                 910

Val Ser Val His Val Leu Ala Arg Glu Met Asp Ser Cys Pro Val Val
            915                 920                 925

Gly Glu Phe Pro Cys Gln Asn Asp Ile Asn Leu Ser Gln Ala Pro Ala
        930                 935                 940

Leu Pro Gln Pro Glu Val Ile Gln Asn Met Thr Glu Phe Lys Arg Gly
945                 950                 955                 960

Leu Pro Leu Phe Pro Leu Val Lys Pro His Ile Asn Phe Met Ala Ala
                965                 970                 975

Lys Leu Lys Leu Ala Ala Ala Leu Glu His His His His His His
            980                 985                 990
```

```
<210> SEQ ID NO 51
<211> LENGTH: 2976
<212> TYPE: DNA
<213> ORGANISM: Artificial sequence
<220> FEATURE:
<223> OTHER INFORMATION: IDE - E111Q mutated, coding sequence

<400> SEQUENCE: 51
atgaataatc ctgcaatcaa gcgtattggt aaccatatta ccaagagccc ggaggacaaa      60
cgtgagtatc gcggcctgga actggccaat ggcatcaagg ttctgctgat cagcgacccg     120
acaaccgaca agagtagtgc agccctggat gtgcatattg gcagcctgag tgatccgcct     180
aacattgccg gtctgagcca cttctgccaa cacatgctgt tcctgggcac caaaaagtac     240
ccgaaagaaa cgagtatag tcagtttctg agcgagcacg caggtagtag caatgccttc     300
acaagcggtg agcacaccaa ttactacttc gacgtgagcc atgaacatct ggagggcgca     360
ctggatcgct ttgcccaatt ctttctgtgc ccgctgtttg acgaaagctg caaagaccgt     420
```

```
gaggtgaacg ccgttgatag cgagcacgag aaaaacgtta tgaacgacgc ctggcgctta   480
ttccagctgg agaaggcaac cggtaacccg aaacacccgt ttagtaagtt cggcacaggc   540
aacaagtaca ccttagaaac ccgccctaac caggagggca ttgacgtgcg ccaagagtta   600
ttaaaatttc acagcgcata ctacagcagc aacctgatgg cagtgtgtgt tctgggccgc   660
gaaagcctgg atgatctgac aaatctggtt gttaaattat tcagtgaggt ggagaacaag   720
aacgtgccgc tgcctgagtt tcctgagcac ccgttccagg aggaacattt aaagcaactg   780
tataaaattg tgccgatcaa agacattcgc aatctgtatg ttacattccc gatcccggac   840
ctgcaaaagt actacaagag caacccgggt cactacttag gccatctgat ggccacgag   900 ggtccgggca gtctgctgag tgaactgaag agcaagggtt gggtgaacac actggttggt   960
ggccagaagg agggcgcacg tggtttcatg ttctttatta tcaatgtgga cctgaccgaa   1020
gaaggtctgc tgcacgtgga ggacatcatc ttacacatgt ttcagtacat tcagaaatta   1080
cgcgcagaag tccgcagga gtgggtgttc caagagtgca aggatctgaa cgcagtggcc   1140
ttccgcttta aagacaaaga gcgtccgcgc ggctatacca gtaaaattgc aggtatctta   1200
cactactacc cgctggagga ggttttaaca gccgagtatc tgctggaaga attccgcccg   1260
gacttaatcg agatggtgct ggacaagtta cgcccggaga cgtgcgtgt tgccattgtg   1320 agcaagagct tcgagggcaa gaccgaccgt accgaagagt ggtacggtac acagtacaag   1380
caggaggcca tccctgatga ggttattaag aagtggcaaa atgccgacct gaatggtaag   1440
tttaagttac cgacaaagaa cgaattcatc ccgaccaact ttgaaatcct gccgctggaa   1500
aaggaagcca ccccgtatcc tgcactgatt aaggacaccg ccatgagcaa attatggttc   1560
aagcaggacg acaaattctt cctgccgaag gcctgcctga atttcgagtt cttcagcccg   1620
ttcgcctacg ttgatccgct gcactgtaat atggcctact tatacctgga gttactgaaa   1680
gacagcttaa atgagtatgc atacgccgca gagctggccg gtttaagcta cgacctgcaa   1740
aataccattt atggcatgta tttaagcgtg aagggctaca cgataaaca accgatctta   1800 ctgaagaaaa ttattgaaaa aatggccacc tttgaaatcg acgagaagcg ttttgaaatt   1860
attaaagagg catatatgcg tagcctgaac aattttcgcg ccgaacaacc gcaccagcac   1920
gcaatgtact acctgcgctt actgatgacc gaagttgcct ggaccaaaga cgagctgaag   1980
gaagccctgg acgatgtgac cttaccgcgt ttaaaggcct tcatcccgca attactgagt   2040
cgtctgcaca ttgaggccct gttacacggt aacatcacca agcaagccgc actgggcatt   2100
atgcagatgt ttgaggatac cctgatcgag cacgcccaca ccaaaccgtt actgccgagt   2160
caactggtgc gctatcgcga agtgcaactg cctgatcgtg gctggtttgt gtatcagcag   2220
cgtaatgagg tgcacaacaa ctgtggtatc gaaatctact accaaaccga catgcaaagc   2280
accagcgaga acatgttcct ggagctgttt tgccagatca tcagcgaacc gtgcttcaac   2340
accctgcgca ccaaggagca attaggctac atcgtgttca gtggccctcg tcgcgcaaat   2400
ggtatccagg gcttacgctt catcatccag agtgaaaaac cgccgcacta cctggaaagt   2460
cgtgttgaag catttttaat cacgatggaa aagagcatcg aggacatgac cgaggaggcc   2520
ttccagaagc acatccaagc cctggcaatc cgtcgcttag ataagccgaa gaagctgagt   2580
gccgagtgcg ccaagtactg gggtgagatc attagccagc agtacaattt cgaccgcgac   2640
aacaccgagg ttgcatacct gaaaaaccctg accaaagaag acatcatcaa attttacaag   2700
gagatgttag cagtggatgc accgcgtcgc cataaagtta cgttcatgt gctggcacgc   2760 gagatggata gttgtccggt ggttggtgaa ttcccgtgcc agaatgacat caacctgagc   2820
```
caagcacctg ccttaccgca accggaggtg atccagaaca tgacagaatt caagcgcggc          2880
ctgccgttat tcccgttagt gaagccgcac atcaacttca tggccgcaaa attaaagctt          2940
gcggccgcac tcgagcacca ccaccaccac cactga                                    2976

<210> SEQ ID NO 52
<211> LENGTH: 991
<212> TYPE: PRT
<213> ORGANISM: Artificial sequence
<220> FEATURE:
<223> OTHER INFORMATION: IDE - E111Q mutated, polypeptide sequence

<400> SEQUENCE: 52

Met Asn Asn Pro Ala Ile Lys Arg Ile Gly Asn His Ile Thr Lys Ser
1               5                   10                  15

Pro Glu Asp Lys Arg Glu Tyr Arg Gly Leu Glu Leu Ala Asn Gly Ile
                20                  25                  30

Lys Val Leu Leu Ile Ser Asp Pro Thr Thr Asp Lys Ser Ser Ala Ala
        35                  40                  45

Leu Asp Val His Ile Gly Ser Leu Ser Asp Pro Pro Asn Ile Ala Gly
    50                  55                  60

Leu Ser His Phe Cys Gln His Met Leu Phe Leu Gly Thr Lys Lys Tyr
65                  70                  75                  80

Pro Lys Glu Asn Glu Tyr Ser Gln Phe Leu Ser Glu His Ala Gly Ser
                85                  90                  95

Ser Asn Ala Phe Thr Ser Gly Glu His Thr Asn Tyr Tyr Phe Asp Val
                100                 105                 110

Ser His Glu His Leu Glu Gly Ala Leu Asp Arg Phe Ala Gln Phe Phe
        115                 120                 125

Leu Cys Pro Leu Phe Asp Glu Ser Cys Lys Asp Arg Glu Val Asn Ala
    130                 135                 140

Val Asp Ser Glu His Glu Lys Asn Val Met Asn Asp Ala Trp Arg Leu
145                 150                 155                 160

Phe Gln Leu Glu Lys Ala Thr Gly Asn Pro Lys His Pro Phe Ser Lys
                165                 170                 175

Phe Gly Thr Gly Asn Lys Tyr Thr Leu Glu Thr Arg Pro Asn Gln Glu
                180                 185                 190

Gly Ile Asp Val Arg Gln Glu Leu Leu Lys Phe His Ser Ala Tyr Tyr
        195                 200                 205

Ser Ser Asn Leu Met Ala Val Cys Val Leu Gly Arg Glu Ser Leu Asp
    210                 215                 220

Asp Leu Thr Asn Leu Val Val Lys Leu Phe Ser Glu Val Glu Asn Lys
225                 230                 235                 240

Asn Val Pro Leu Pro Glu Phe Pro Glu His Pro Phe Gln Glu Glu His
                245                 250                 255

Leu Lys Gln Leu Tyr Lys Ile Val Pro Ile Lys Asp Ile Arg Asn Leu
                260                 265                 270

Tyr Val Thr Phe Pro Ile Pro Asp Leu Gln Lys Tyr Tyr Lys Ser Asn
        275                 280                 285

Pro Gly His Tyr Leu Gly His Leu Ile Gly His Glu Gly Pro Gly Ser
    290                 295                 300

Leu Leu Ser Glu Leu Lys Ser Lys Gly Trp Val Asn Thr Leu Val Gly
305                 310                 315                 320

Gly Gln Lys Glu Gly Ala Arg Gly Phe Met Phe Phe Ile Ile Asn Val
                325                 330                 335

-continued

```
Asp Leu Thr Glu Glu Gly Leu Leu His Val Glu Asp Ile Ile Leu His
        340                 345                 350

Met Phe Gln Tyr Ile Gln Lys Leu Arg Ala Glu Gly Pro Gln Glu Trp
        355                 360                 365

Val Phe Gln Glu Cys Lys Asp Leu Asn Ala Val Ala Phe Arg Phe Lys
        370                 375                 380

Asp Lys Glu Arg Pro Arg Gly Tyr Thr Ser Lys Ile Ala Gly Ile Leu
385                 390                 395                 400

His Tyr Tyr Pro Leu Glu Glu Val Leu Thr Ala Glu Tyr Leu Leu Glu
                405                 410                 415

Glu Phe Arg Pro Asp Leu Ile Glu Met Val Leu Asp Lys Leu Arg Pro
                420                 425                 430

Glu Asn Val Arg Val Ala Ile Val Ser Lys Ser Phe Glu Gly Lys Thr
        435                 440                 445

Asp Arg Thr Glu Glu Trp Tyr Gly Thr Gln Tyr Lys Gln Glu Ala Ile
        450                 455                 460

Pro Asp Glu Val Ile Lys Lys Trp Gln Asn Ala Asp Leu Asn Gly Lys
465                 470                 475                 480

Phe Lys Leu Pro Thr Lys Asn Glu Phe Ile Pro Thr Asn Phe Glu Ile
                485                 490                 495

Leu Pro Leu Glu Lys Glu Ala Thr Pro Tyr Pro Ala Leu Ile Lys Asp
                500                 505                 510

Thr Ala Met Ser Lys Leu Trp Phe Lys Gln Asp Asp Lys Phe Phe Leu
        515                 520                 525

Pro Lys Ala Cys Leu Asn Phe Glu Phe Phe Ser Pro Phe Ala Tyr Val
        530                 535                 540

Asp Pro Leu His Cys Asn Met Ala Tyr Leu Tyr Leu Glu Leu Leu Lys
545                 550                 555                 560

Asp Ser Leu Asn Glu Tyr Ala Tyr Ala Ala Glu Leu Ala Gly Leu Ser
                565                 570                 575

Tyr Asp Leu Gln Asn Thr Ile Tyr Gly Met Tyr Leu Ser Val Lys Gly
        580                 585                 590

Tyr Asn Asp Lys Gln Pro Ile Leu Leu Lys Lys Ile Ile Glu Lys Met
        595                 600                 605

Ala Thr Phe Glu Ile Asp Glu Lys Arg Phe Glu Ile Ile Lys Glu Ala
        610                 615                 620

Tyr Met Arg Ser Leu Asn Asn Phe Arg Ala Glu Gln Pro His Gln His
625                 630                 635                 640

Ala Met Tyr Tyr Leu Arg Leu Leu Met Thr Glu Val Ala Trp Thr Lys
                645                 650                 655

Asp Glu Leu Lys Glu Ala Leu Asp Asp Val Thr Leu Pro Arg Leu Lys
        660                 665                 670

Ala Phe Ile Pro Gln Leu Leu Ser Arg Leu His Ile Glu Ala Leu Leu
        675                 680                 685

His Gly Asn Ile Thr Lys Gln Ala Ala Leu Gly Ile Met Gln Met Val
        690                 695                 700

Glu Asp Thr Leu Ile Glu His Ala His Thr Lys Pro Leu Leu Pro Ser
705                 710                 715                 720

Gln Leu Val Arg Tyr Arg Glu Val Gln Leu Pro Asp Arg Gly Trp Phe
                725                 730                 735

Val Tyr Gln Gln Arg Asn Glu Val His Asn Asn Cys Gly Ile Glu Ile
        740                 745                 750
```

-continued

```
Tyr Tyr Gln Thr Asp Met Gln Ser Thr Ser Glu Asn Met Phe Leu Glu
        755             760             765

Leu Phe Cys Gln Ile Ile Ser Glu Pro Cys Phe Asn Thr Leu Arg Thr
    770             775             780

Lys Glu Gln Leu Gly Tyr Ile Val Phe Ser Gly Pro Arg Arg Ala Asn
785             790             795             800

Gly Ile Gln Gly Leu Arg Phe Ile Ile Gln Ser Glu Lys Pro Pro His
            805             810             815

Tyr Leu Glu Ser Arg Val Glu Ala Phe Leu Ile Thr Met Glu Lys Ser
            820             825             830

Ile Glu Asp Met Thr Glu Glu Ala Phe Gln Lys His Ile Gln Ala Leu
        835             840             845

Ala Ile Arg Arg Leu Asp Lys Pro Lys Lys Leu Ser Ala Glu Cys Ala
    850             855             860

Lys Tyr Trp Gly Glu Ile Ile Ser Gln Gln Tyr Asn Phe Asp Arg Asp
865             870             875             880

Asn Thr Glu Val Ala Tyr Leu Lys Thr Leu Thr Lys Glu Asp Ile Ile
            885             890             895

Lys Phe Tyr Lys Glu Met Leu Ala Val Asp Ala Pro Arg Arg His Lys
            900             905             910

Val Ser Val His Val Leu Ala Arg Glu Met Asp Ser Cys Pro Val Val
            915             920             925

Gly Glu Phe Pro Cys Gln Asn Asp Ile Asn Leu Ser Gln Ala Pro Ala
    930             935             940

Leu Pro Gln Pro Glu Val Ile Gln Asn Met Thr Glu Phe Lys Arg Gly
945             950             955             960

Leu Pro Leu Phe Pro Leu Val Lys Pro His Ile Asn Phe Met Ala Ala
            965             970             975

Lys Leu Lys Leu Ala Ala Ala Leu Glu His His His His His His
            980             985             990
```